US012691671B2

(12) United States Patent
Hall et al.

(10) Patent No.: US 12,691,671 B2
(45) Date of Patent: *Jul. 28, 2026

(54) ROTATIONAL SPUN MATERIAL COVERED MEDICAL APPLIANCES AND METHODS OF MANUFACTURE

(71) Applicant: Merit Medical Systems, Inc., South Jordan, UT (US)

(72) Inventors: John William Hall, North Salt Lake, UT (US); Zeke Eller, Plano, TX (US); Robert S. Kellar, Flagstaff, AZ (US); Rachel Lynn Oberg, Bountiful, UT (US); Bart Dolmatch, Palo Alto, CA (US); Wayne Mower, Bountiful, UT (US); Robert J. Radford, Freemont, CA (US)

(73) Assignee: Merit Medical Systems, Inc., South Jordan, UT (US)

( * ) Notice: Subject to any disclaimer, the term of this patent is extended or adjusted under 35 U.S.C. 154(b) by 1271 days.

This patent is subject to a terminal disclaimer.

(21) Appl. No.: 16/896,013

(22) Filed: Jun. 8, 2020

(65) Prior Publication Data

US 2020/0369017 A1 Nov. 26, 2020

Related U.S. Application Data

(60) Continuation of application No. 14/832,422, filed on Aug. 21, 2015, now Pat. No. 10,675,850, which is a
(Continued)

(51) Int. Cl.
*D01D 5/18* (2006.01)
*A61F 2/00* (2006.01)
(Continued)

(52) U.S. Cl.
CPC ............ *B32B 38/0036* (2013.01); *A61F 2/06* (2013.01); *A61F 2/07* (2013.01); *A61F 2/82* (2013.01);
(Continued)

(58) Field of Classification Search
CPC .. A61F 2/82; A61F 2/88; A61F 2/0077; A61F 2002/009; A61F 2002/0091;
(Continued)

(56) References Cited

U.S. PATENT DOCUMENTS 2,772,444 A 12/1956 Burrows et al.
3,047,444 A 7/1962 Harwood
(Continued)

FOREIGN PATENT DOCUMENTS

AT 366546 6/1976
CN 1823687 8/2006
(Continued)

OTHER PUBLICATIONS

Office Action dated Jun. 20, 2023 for U.S. Appl. No. 17/068,627.
(Continued)

*Primary Examiner* — Leslie A Lopez
(74) *Attorney, Agent, or Firm* — Dorsey & Whitney LLP

(57) ABSTRACT

A medical appliance or prosthesis may comprise one or more layers of rotational spun nanofibers, including rotational spun polymers. The rotational spun material may comprise layers including layers of polytetrafluoroethylene (PTFE). Rotational spun nanofiber mats of certain porosities may permit tissue ingrowth into or attachment to the prosthesis. Additionally, one or more cuffs may be configured to allow tissue ingrowth to anchor the prosthesis.

26 Claims, 23 Drawing Sheets
(1 of 23 Drawing Sheet(s) Filed in Color)

Related U.S. Application Data division of application No. 13/742,025, filed on Jan. 15, 2013, now Pat. No. 9,987,833.

(60) Provisional application No. 61/672,633, filed on Jul. 17, 2012, provisional application No. 61/637,693, filed on Apr. 24, 2012, provisional application No. 61/587,088, filed on Jan. 16, 2012.

(51) Int. Cl.

| | |
|---|---|
| *A61F 2/06* | (2013.01) |
| *A61F 2/07* | (2013.01) |
| *A61F 2/82* | (2013.01) |
| *A61F 2/852* | (2013.01) |
| *A61F 2/88* | (2006.01) |
| *A61L 27/34* | (2006.01) |
| *A61L 27/56* | (2006.01) |
| *A61L 31/10* | (2006.01) |
| *A61L 31/14* | (2006.01) |
| *B05D 1/00* | (2006.01) |
| *B32B 38/00* | (2006.01) |
| *C09D 127/18* | (2006.01) |
| *D01F 6/12* | (2006.01) |
| *A61F 2/89* | (2013.01) |

(52) U.S. Cl.
CPC ............... *A61F 2/852* (2013.01); *A61F 2/88* (2013.01); *A61L 27/34* (2013.01); *A61L 27/56* (2013.01); *A61L 31/10* (2013.01); *A61L 31/146* (2013.01); *B05D 1/005* (2013.01); *C09D 127/18* (2013.01); *D01D 5/18* (2013.01); *D01F 6/12* (2013.01); *A61F 2/0077* (2013.01); *A61F 2002/065* (2013.01); *A61F 2002/072* (2013.01); *A61F 2002/075* (2013.01); *A61F 2/89* (2013.01); *A61F 2210/0076* (2013.01); *A61F 2230/005* (2013.01); *A61L 2420/02* (2013.01); *A61L 2420/08* (2013.01); *B32B 2255/10* (2013.01)

(58) Field of Classification Search
CPC ........ A61F 2/06; A61F 2/07; A61F 2002/072; A61F 2002/0075; A61F 2/89; A61F 2210/0076; B32B 38/00; A61L 27/56
See application file for complete search history.

(56) References Cited

U.S. PATENT DOCUMENTS

| | | | |
|---|---|---|---|
| 3,203,365 | A | 8/1965 | Bowe et al. |
| 4,043,331 | A | 8/1977 | Martin et al. |
| 4,044,404 | A | 8/1977 | Martin et al. |
| 4,096,227 | A | 6/1978 | Gore |
| 4,127,706 | A | 11/1978 | Martin et al. |
| 4,223,101 | A | 9/1980 | Fine et al. |
| 4,323,525 | A | 4/1982 | Bornat |
| 4,345,414 | A | 8/1982 | Bornat et al. |
| 4,552,707 | A | 11/1985 | How |
| 4,689,186 | A | 8/1987 | Bornat |
| 4,758,223 | A | 7/1988 | Rydell |
| 5,167,890 | A | 12/1992 | Sasshofer et al. |
| 5,172,702 | A | 12/1992 | Leigh |
| 5,236,447 | A | 8/1993 | Kubo |
| 5,328,946 | A | 7/1994 | Tuminello et al. |
| 5,344,297 | A | 9/1994 | Hills |
| 5,509,902 | A | 4/1996 | Raulerson |
| 5,512,051 | A | 4/1996 | Wang et al. |
| 5,552,100 | A | 9/1996 | Shannon et al. |
| 5,562,986 | A | 10/1996 | Yamamoto et al. |
| 5,601,572 | A | 2/1997 | Middleman et al. |
| 5,620,763 | A | 4/1997 | House et al. |
| 5,655,542 | A | 8/1997 | Weilandt |
| 5,665,428 | A | 9/1997 | Cha et al. |
| 5,700,572 | A | 12/1997 | Klatt et al. |
| 5,702,658 | A | 12/1997 | Pellegrin et al. |
| 5,741,333 | A | 4/1998 | Frid |
| 5,776,609 | A | 7/1998 | Mccullough |
| 5,788,651 | A | 8/1998 | Weilandt |
| 5,800,389 | A | 9/1998 | Burney et al. |
| 5,810,870 | A | 9/1998 | Myers et al. |
| 5,842,999 | A | 12/1998 | Pruitt et al. |
| 5,922,021 | A | 7/1999 | Jang |
| 5,941,910 | A | 8/1999 | Schindler et al. |
| D418,223 | S | 12/1999 | Phipps et al. |
| 6,010,529 | A | 1/2000 | Herweck et al. |
| 6,015,431 | A | 1/2000 | Thornton et al. |
| 6,045,567 | A | 4/2000 | Taylor et al. |
| 6,053,943 | A | 4/2000 | Edwin et al. |
| 6,075,180 | A | 6/2000 | Sharber et al. |
| D428,150 | S | 7/2000 | Ruf et al. |
| 6,106,913 | A | 8/2000 | Scardino |
| 6,126,617 | A | 10/2000 | Weilandt et al. |
| 6,156,064 | A | 12/2000 | Chouinard |
| 6,165,212 | A | 12/2000 | Dereume et al. |
| 6,165,215 | A | 12/2000 | Rottenberg et al. |
| 6,176,875 | B1 | 1/2001 | Lenker et al. |
| 6,196,978 | B1 | 3/2001 | Weilandt et al. |
| 6,238,430 | B1 | 5/2001 | Klumb |
| 6,273,861 | B1 | 8/2001 | Bates et al. |
| 6,306,424 | B1 | 10/2001 | Vyakarnam |
| 6,312,454 | B1 | 11/2001 | Stockel et al. |
| 6,322,523 | B2 | 11/2001 | Weilandt et al. |
| D457,955 | S | 5/2002 | Bilitz |
| 6,383,214 | B1 | 5/2002 | Banas et al. |
| 6,419,641 | B1 | 7/2002 | Mark et al. |
| 6,436,135 | B1 | 8/2002 | Goldfarb |
| D463,555 | S | 9/2002 | Etter et al. |
| 6,488,662 | B2 | 12/2002 | Sirimanne |
| 6,497,687 | B1 | 12/2002 | Blanco |
| 6,498,207 | B1 | 12/2002 | Hoshikawa et al. |
| 6,517,571 | B1 | 2/2003 | Brauker et al. |
| 6,673,105 | B1 | 1/2004 | Chen |
| 6,679,913 | B2 | 1/2004 | Homsy |
| 6,685,736 | B1 | 2/2004 | White et al. |
| 6,719,783 | B2 | 4/2004 | Lentz et al. |
| D490,152 | S | 5/2004 | Myall et al. |
| 6,752,826 | B2 | 6/2004 | Holloway et al. |
| 7,001,556 | B1 | 2/2006 | Shambaugh |
| 7,041,065 | B2 | 5/2006 | Weilandt et al. |
| 7,115,220 | B2 | 10/2006 | Dubson et al. |
| 7,118,698 | B2 | 10/2006 | Armantrout et al. |
| 7,244,272 | B2 | 7/2007 | Dubson et al. |
| 7,247,160 | B2 | 7/2007 | Seiler et al. |
| 7,316,754 | B2 | 1/2008 | Ide et al. |
| D571,009 | S | 6/2008 | Smith et al. |
| 7,413,575 | B2 | 8/2008 | Phaneuf et al. |
| 7,416,559 | B2 | 8/2008 | Shalaby |
| D586,916 | S | 2/2009 | Faulkner et al. |
| 7,485,141 | B2 | 2/2009 | Majercak et al. |
| 7,498,079 | B1 | 3/2009 | Donckers |
| 7,524,527 | B2 | 4/2009 | Stenzel |
| 7,556,634 | B2 | 7/2009 | Lee et al. |
| D598,543 | S | 8/2009 | Vogel et al. |
| 7,582,240 | B2 | 9/2009 | Marin et al. |
| 7,608,048 | B2 | 10/2009 | Goldenberg |
| 7,655,175 | B2 | 2/2010 | Michael et al. |
| D612,044 | S | 3/2010 | Scheibe |
| D612,051 | S | 3/2010 | Ruf |
| D619,251 | S | 7/2010 | Justiniano-Garcia et al. |
| 7,799,261 | B2 | 9/2010 | Orr et al. |
| 7,857,608 | B2 | 12/2010 | Fabbricante et al. |
| 7,914,568 | B2 | 3/2011 | Cully et al. |
| 7,947,069 | B2 | 5/2011 | Sanders |
| 7,981,353 | B2 | 7/2011 | Mitchell et al. |
| 8,052,743 | B2 | 11/2011 | Weber et al. |
| 8,052,744 | B2 | 11/2011 | Girton |
| 8,092,768 | B2 | 1/2012 | Miller et al. |
| 8,137,317 | B2 | 3/2012 | Osypka |
| 8,178,030 | B2 | 5/2012 | Anneaux et al. |
| 8,257,640 | B2 | 9/2012 | Anneaux et al. |
| 8,262,979 | B2 | 9/2012 | Anneaux et al. |

(56)  References Cited

U.S. PATENT DOCUMENTS

| | | | |
|---|---|---|---|
| 8,637,109 B2 | 1/2014 | Grewe et al. | |
| 8,691,543 B2 | 4/2014 | Gaudette et al. | |
| 8,771,582 B2 | 7/2014 | Phaneuf et al. | |
| 9,034,031 B2 | 5/2015 | Anneaux | |
| 9,198,999 B2 | 12/2015 | Hall | |
| 9,392,998 B2 | 7/2016 | Snow | |
| 9,572,693 B2 | 2/2017 | Cottone et al. | |
| 9,655,710 B2 | 5/2017 | Eller | |
| 9,775,933 B2 | 10/2017 | Knisley et al. | |
| 9,856,588 B2 | 1/2018 | Anneaux | |
| 10,010,395 B2 | 7/2018 | Puckett | |
| 10,028,852 B2 | 7/2018 | Hall | |
| 10,154,918 B2 | 12/2018 | Haselby et al. | |
| 10,405,963 B2 | 9/2019 | Mcalpine | |
| 10,653,512 B2 | 5/2020 | Eller et al. | |
| 10,675,850 B2 | 6/2020 | Hall et al. | |
| 11,541,154 B2 | 1/2023 | Hall et al. | |
| 2001/0009979 A1 | 7/2001 | Weilandt et al. | |
| 2001/0034549 A1 | 10/2001 | Bartholf et al. | |
| 2001/0039446 A1 | 11/2001 | Edwin et al. | |
| 2001/0049551 A1 | 12/2001 | Tseng et al. | |
| 2001/0053929 A1 | 12/2001 | Vonesh et al. | |
| 2002/0049489 A1 | 4/2002 | Herweck et al. | |
| 2002/0077693 A1 | 6/2002 | Barclay | |
| 2002/0082675 A1 | 6/2002 | Myers | |
| 2002/0084178 A1 | 7/2002 | Dubson | |
| 2002/0090725 A1 | 7/2002 | Simpson et al. | |
| 2002/0107565 A1 | 8/2002 | Greenhalgh | |
| 2002/0198588 A1 | 12/2002 | Armstrong et al. | |
| 2003/0040772 A1 | 2/2003 | Hyodoh et al. | |
| 2003/0050711 A1 | 3/2003 | Laurencin | |
| 2003/0060871 A1 | 3/2003 | Hill et al. | |
| 2003/0074049 A1 | 4/2003 | Hoganson | |
| 2003/0100944 A1 | 5/2003 | Laksin et al. | |
| 2003/0114917 A1 | 6/2003 | Holloway et al. | |
| 2003/0139797 A1 | 7/2003 | Johnson | |
| 2003/0195611 A1 | 10/2003 | Greenhalgh et al. | |
| 2003/0211135 A1 | 11/2003 | Greenhalgh et al. | |
| 2004/0016260 A1 | 1/2004 | Kobayashi et al. | |
| 2004/0030377 A1 | 2/2004 | Dubson et al. | |
| 2004/0033364 A1 | 2/2004 | Spiridigliozzi et al. | |
| 2004/0038038 A1 | 2/2004 | Yeung | |
| 2004/0051201 A1 | 3/2004 | Greenhalgh et al. | |
| 2004/0054397 A1 | 3/2004 | Smith et al. | |
| 2004/0107004 A1 | 6/2004 | Levine et al. | |
| 2004/0133124 A1 | 7/2004 | Bates et al. | |
| 2004/0167606 A1 | 8/2004 | Chouinard | |
| 2004/0215103 A1 | 10/2004 | Mueller et al. | |
| 2004/0219345 A1 | 11/2004 | Armantrout et al. | |
| 2005/0053782 A1 | 3/2005 | Sen et al. | |
| 2005/0054947 A1 | 3/2005 | Goldenberg | |
| 2005/0125017 A1 | 6/2005 | Kudrna et al. | |
| 2005/0137675 A1 | 6/2005 | Dubson et al. | |
| 2005/0171593 A1 | 8/2005 | Whirley et al. | |
| 2005/0187605 A1 | 8/2005 | Greenhalgh et al. | |
| 2005/0244453 A1 | 11/2005 | Stucke et al. | |
| 2005/0244639 A1 | 11/2005 | Marin et al. | |
| 2005/0278018 A1 | 12/2005 | Jensen | |
| 2006/0015138 A1 | 1/2006 | Gertner | |
| 2006/0085019 A1 | 4/2006 | Cote et al. | |
| 2006/0142852 A1 | 6/2006 | Sowinski et al. | |
| 2006/0155210 A1 | 7/2006 | Beckman et al. | |
| 2006/0200232 A1 | 9/2006 | Phaneuf et al. | |
| 2006/0228435 A1 | 10/2006 | Andrady et al. | |
| 2006/0233990 A1 | 10/2006 | Humphrey et al. | |
| 2006/0259131 A1 | 11/2006 | Molaei et al. | |
| 2006/0259137 A1 | 11/2006 | Artof et al. | |
| 2006/0276874 A1 | 12/2006 | Wilson et al. | |
| 2007/0023131 A1 | 2/2007 | Farnsworth et al. | |
| 2007/0026036 A1 | 2/2007 | Falotico et al. | |
| 2007/0027407 A1 | 2/2007 | Miller | |
| 2007/0031607 A1 | 2/2007 | Dubson et al. | |
| 2007/0043428 A1 | 2/2007 | Jennings et al. | |
| 2007/0078472 A1 | 4/2007 | Singh | |
| 2007/0087027 A1 | 4/2007 | Greenhalgh et al. | |
| 2007/0123973 A1 | 5/2007 | Roth | |
| 2007/0142744 A1 | 6/2007 | Provencher | |
| 2007/0142771 A1 | 6/2007 | Durcan | |
| 2007/0179403 A1 | 8/2007 | Heske et al. | |
| 2007/0198097 A1 | 8/2007 | Zegdi | |
| 2007/0207179 A1 | 9/2007 | Andersen et al. | |
| 2007/0207186 A1 | 9/2007 | Scanlon et al. | |
| 2007/0244569 A1 | 10/2007 | Weber et al. | |
| 2007/0250037 A1 | 10/2007 | Brimhall et al. | |
| 2007/0269481 A1 | 11/2007 | Li et al. | |
| 2007/0276477 A1 | 11/2007 | Lee et al. | |
| 2008/0021545 A1 | 1/2008 | Reneker et al. | |
| 2008/0029617 A1 | 2/2008 | Marshall et al. | |
| 2008/0118541 A1 | 5/2008 | Pacetti | |
| 2008/0119943 A1 | 5/2008 | Armstrong et al. | |
| 2008/0188923 A1 | 8/2008 | Chu | |
| 2008/0199506 A1 | 8/2008 | Horres et al. | |
| 2008/0200833 A1 | 8/2008 | Hardin et al. | |
| 2008/0200835 A1 | 8/2008 | Monson et al. | |
| 2008/0208323 A1 | 8/2008 | El-Kurdi et al. | |
| 2008/0208325 A1* | 8/2008 | Helmus | A61F 2/06 623/1.13 |
| 2008/0228104 A1 | 9/2008 | Uber et al. | |
| 2008/0234812 A1 | 9/2008 | Pacetti | |
| 2008/0242171 A1 | 10/2008 | Huang et al. | |
| 2008/0281223 A1 | 11/2008 | Goldenberg | |
| 2008/0281406 A1 | 11/2008 | Addonizio et al. | |
| 2008/0286321 A1 | 11/2008 | Reneker et al. | |
| 2008/0288044 A1 | 11/2008 | Osborne | |
| 2008/0300507 A1 | 12/2008 | Figueredo et al. | |
| 2008/0305143 A1 | 12/2008 | Chen et al. | |
| 2008/0319535 A1 | 12/2008 | Craven et al. | |
| 2009/0012607 A1 | 1/2009 | Kim et al. | |
| 2009/0018643 A1 | 1/2009 | Hashi et al. | |
| 2009/0030499 A1 | 1/2009 | Bebb et al. | |
| 2009/0041978 A1 | 2/2009 | Sogard et al. | |
| 2009/0082846 A1 | 3/2009 | Chobotov | |
| 2009/0088828 A1 | 4/2009 | Shalev et al. | |
| 2009/0127748 A1 | 5/2009 | Takahashi | |
| 2009/0136651 A1 | 5/2009 | Larsen et al. | |
| 2009/0143698 A1 | 6/2009 | Janssens | |
| 2009/0160099 A1 | 6/2009 | Huang | |
| 2009/0163994 A1 | 6/2009 | Quigley et al. | |
| 2009/0171456 A1 | 7/2009 | Kveen et al. | |
| 2009/0227944 A1 | 9/2009 | Weber | |
| 2009/0232920 A1 | 9/2009 | Lozano et al. | |
| 2009/0237920 A1 | 9/2009 | Dallas et al. | |
| 2009/0248131 A1 | 10/2009 | Greenan | |
| 2009/0248144 A1 | 10/2009 | Bahler et al. | |
| 2009/0259200 A1 | 10/2009 | Lampropoulos et al. | |
| 2009/0269429 A1 | 10/2009 | Lozano et al. | |
| 2009/0280325 A1* | 11/2009 | Lozano | D01D 5/06 977/788 |
| 2009/0299220 A1 | 12/2009 | Field et al. | |
| 2009/0319034 A1 | 12/2009 | Sowinski | |
| 2010/0013126 A1 | 1/2010 | Ishaque et al. | |
| 2010/0036479 A1 | 2/2010 | Hill et al. | |
| 2010/0042198 A1 | 2/2010 | Burton | |
| 2010/0042199 A1 | 2/2010 | Burton | |
| 2010/0063574 A1 | 3/2010 | Bogert | |
| 2010/0076401 A1 | 3/2010 | Von Oepen et al. | |
| 2010/0076543 A1 | 3/2010 | Melsheimer et al. | |
| 2010/0093093 A1 | 4/2010 | Leong et al. | |
| 2010/0119578 A1 | 5/2010 | To et al. | |
| 2010/0129628 A1 | 5/2010 | Young | |
| 2010/0130887 A1 | 5/2010 | Selis | |
| 2010/0168773 A1 | 7/2010 | Funderburk et al. | |
| 2010/0185156 A1 | 7/2010 | Kanner et al. | |
| 2010/0190254 A1 | 7/2010 | Chian et al. | |
| 2010/0193999 A1 | 8/2010 | Anneaux et al. | |
| 2010/0233115 A1 | 9/2010 | Patel et al. | |
| 2010/0280590 A1 | 11/2010 | Sun et al. | |
| 2010/0304205 A1 | 12/2010 | Jo et al. | |
| 2010/0323052 A1 | 12/2010 | Orr et al. | |
| 2010/0331965 A1 | 12/2010 | Dugas et al. | |
| 2011/0030885 A1* | 2/2011 | Anneaux | A61F 2/07 156/187 |
| 2011/0031656 A1 | 2/2011 | Anneaux et al. | |
| 2011/0060276 A1 | 3/2011 | Schaeffer et al. | |

(56) References Cited

U.S. PATENT DOCUMENTS

| | | |
|---|---|---|
| 2011/0087318 A1 | 4/2011 | Daugherty et al. |
| 2011/0089603 A1 | 4/2011 | Fabbricante et al. |
| 2011/0135806 A1 | 6/2011 | Grewe et al. |
| 2011/0142804 A1 | 6/2011 | Gaudette et al. |
| 2011/0152715 A1 | 6/2011 | Delap et al. |
| 2011/0156319 A1 | 6/2011 | Kurokawa et al. |
| 2011/0224715 A1 | 9/2011 | Chin et al. |
| 2011/0251631 A1 | 10/2011 | Trees et al. |
| 2011/0263456 A1 | 10/2011 | Harttig |
| 2011/0295200 A1 | 12/2011 | Speck et al. |
| 2011/0301696 A1 | 12/2011 | Mangiardi |
| 2012/0114722 A1 | 5/2012 | Ballard et al. |
| 2012/0191176 A1 | 7/2012 | Nagl et al. |
| 2012/0201988 A1 | 8/2012 | Hansen et al. |
| 2012/0220894 A1 | 8/2012 | Melsheimer |
| 2012/0225602 A1 | 9/2012 | Qi et al. |
| 2012/0271396 A1 | 10/2012 | Zheng |
| 2012/0292810 A1 | 11/2012 | Peno et al. |
| 2012/0316633 A1 | 12/2012 | Flanagan et al. |
| 2013/0018220 A1 | 1/2013 | Vad |
| 2013/0023175 A1 | 1/2013 | Anneaux et al. |
| 2013/0053948 A1 | 2/2013 | Anneaux et al. |
| 2013/0059497 A1 | 3/2013 | Anneaux et al. |
| 2013/0079700 A1 | 3/2013 | Ballard et al. |
| 2013/0085565 A1 | 4/2013 | Eller et al. |
| 2013/0131548 A1 | 5/2013 | Mcghie et al. |
| 2013/0150795 A1 | 6/2013 | Snow |
| 2013/0184808 A1 | 7/2013 | Hall et al. |
| 2013/0184810 A1 | 7/2013 | Hall et al. |
| 2013/0231733 A1 | 9/2013 | Knisley et al. |
| 2013/0238086 A1 | 9/2013 | Ballard et al. |
| 2013/0268062 A1 | 10/2013 | Puckett et al. |
| 2013/0316103 A1 | 11/2013 | Anneaux et al. |
| 2013/0324910 A1 | 12/2013 | Ohri et al. |
| 2014/0012304 A1 | 1/2014 | Lampropoulos et al. |
| 2014/0079758 A1 | 3/2014 | Hall et al. |
| 2014/0081386 A1 | 3/2014 | Haselby et al. |
| 2014/0081414 A1 | 3/2014 | Hall et al. |
| 2014/0086971 A1 | 3/2014 | Hall et al. |
| 2014/0100479 A1 | 4/2014 | Tripp et al. |
| 2014/0171826 A1 | 6/2014 | Lampropoulos et al. |
| 2014/0207021 A1 | 7/2014 | Snow |
| 2014/0265061 A1 | 9/2014 | Hall et al. |
| 2014/0273703 A1 | 9/2014 | Mower et al. |
| 2015/0045828 A1 | 2/2015 | Mcarthur et al. |
| 2015/0081000 A1 | 3/2015 | Hossainy |
| 2015/0094751 A1 | 4/2015 | Chen et al. |
| 2015/0134051 A1 | 5/2015 | Donadio et al. |
| 2015/0148459 A1 | 5/2015 | Pawloski et al. |
| 2015/0201917 A1 | 7/2015 | Snow |
| 2015/0201963 A1 | 7/2015 | Snow |
| 2015/0320542 A1 | 11/2015 | Gabriele et al. |
| 2016/0060797 A1 | 3/2016 | Anneaux et al. |
| 2016/0250048 A1 | 9/2016 | Hall et al. |
| 2016/0331528 A1 | 11/2016 | Parker |
| 2017/0360993 A1 | 12/2017 | Argentine et al. |
| 2018/0064565 A1 | 3/2018 | Mactaggart |
| 2019/0008665 A1 | 1/2019 | Hall et al. |
| 2019/0060528 A1 | 2/2019 | Skender et al. |
| 2019/0076276 A1 | 3/2019 | Longo |
| 2019/0110911 A1 | 4/2019 | Nae |
| 2020/0015987 A1 | 1/2020 | Einav |
| 2020/0369016 A1 | 11/2020 | Hall et al. |
| 2020/0369017 A1 | 11/2020 | Hall et al. |
| 2020/0375725 A1 | 12/2020 | Chobotov et al. |
| 2020/0383767 A1 | 12/2020 | Eller et al. |
| 2021/0162098 A1 | 6/2021 | Mower et al. |
| 2021/0290416 A1 | 9/2021 | Hall et al. |
| 2022/0047783 A1 | 2/2022 | Hall et al. |
| 2022/0048285 A1 | 2/2022 | Hall et al. |
| 2022/0273708 A1 | 9/2022 | Hall et al. |
| 2023/0157804 A1 | 5/2023 | Eller et al. |
| 2023/0191005 A1 | 6/2023 | Hall et al. |
| 2023/0311472 A1 | 10/2023 | Hall et al. |
| 2025/0235304 A1 | 7/2025 | Hall et al. |
| 2025/0236104 A1 | 7/2025 | Hall et al. |
| 2025/0375476 A1 | 12/2025 | Hall et al. |

FOREIGN PATENT DOCUMENTS

| | | |
|---|---|---|
| CN | 1264571 | 9/2007 |
| CN | 101584612 | 11/2009 |
| CN | 102560896 A | 7/2012 |
| CN | 109157928 A | 1/2019 |
| DE | 102011012501 A1 | 8/2012 |
| EP | 0457456 | 11/1991 |
| EP | 0966920 | 4/2004 |
| EP | 1605014 | 12/2005 |
| EP | 1679039 | 7/2006 |
| EP | 2363516 | 7/2011 |
| EP | 2363516 A1 | 9/2011 |
| EP | 2944711 B1 | 12/2017 |
| GB | 1577221 | 10/1980 |
| JP | 5140476 | 5/1975 |
| JP | 2005511242 A | 4/2005 |
| JP | 2007519491 | 7/2007 |
| JP | 2007531833 | 11/2007 |
| JP | 2009232882 | 10/2009 |
| JP | 2010517625 | 5/2010 |
| JP | 2010540190 | 12/2010 |
| JP | 2013501539 A | 1/2013 |
| JP | 2015504739 | 2/2015 |
| KR | 20100077913 | 7/2010 |
| KR | 20100108382 | 10/2010 |
| KR | 1020100108382 | 10/2010 |
| WO | 199622733 | 8/1996 |
| WO | 199800090 | 1/1998 |
| WO | 199944505 | 9/1999 |
| WO | 2002049536 | 6/2002 |
| WO | 2003051233 | 6/2003 |
| WO | 2004090206 | 10/2004 |
| WO | 2005018600 | 3/2005 |
| WO | 2005074547 | 8/2005 |
| WO | 2005098100 | 10/2005 |
| WO | 2006013389 | 2/2006 |
| WO | 2006123340 | 11/2006 |
| WO | 2007075256 | 7/2007 |
| WO | 2008097592 | 8/2008 |
| WO | 2009046372 | 4/2009 |
| WO | 2009127170 | 10/2009 |
| WO | 2009146280 | 12/2009 |
| WO | 2010083530 | 7/2010 |
| WO | 2010132636 | 11/2010 |
| WO | 2011017698 | 2/2011 |
| WO | 2012103501 | 8/2012 |
| WO | 2012122485 | 9/2012 |
| WO | 2012167216 | 12/2012 |
| WO | 2013109528 | 7/2013 |
| WO | 2013151778 | 7/2013 |
| WO | 2014007979 | 1/2014 |
| WO | 2014066297 A1 | 5/2014 |

OTHER PUBLICATIONS

International Preliminary Report dated Mar. 24, 2015 for PCT/US2013/060812.

International Preliminary Report dated Jul. 30, 2013 for PCT/US2012/023006.

International Search Report and Written Opinion dated Jun. 14, 2022 for PCT/US2022/070844.

Notice of Allowance dated Mar. 13, 2020 for U.S. Appl. No. 14/832,422.

Office Action dated May 22, 2023 for U.S. Appl. No. 16/877,259.

Takmakov , et al., "Carbon Microelectrodes with a Renewable Surface", NIH Public Access, available in PMC, Anal Chem. 82(5), Mar. 1, 2010, 2020-2028.

Cho , et al., "Self-Healing Polymer Coatings", Advanced Materials, 21, Jan. 1, 2009, 645-649.

European Examination Report dated May 10, 2023 for EP20191283.9.

(56) References Cited

OTHER PUBLICATIONS

Notice of Allowance dated Feb. 24, 2022 for U.S. Appl. No. 16/035,334.
Office Action dated Dec. 24, 2021 for U.S. Appl. No. 16/877,259.
Office Action dated Sep. 8, 2023 for U.S. Appl. No. 17/652,552.
Office Action dated Aug. 6, 2018 for U.S. Appl. No. 13/360,444.
Office Action dated Aug. 7, 2019 for U.S. Appl. No. 15/806,020.
Office Action dated Aug. 10, 2015 for U.S. Appl. No. 14/044,050.
Office Action dated Aug. 22, 2019 for U.S. Appl. No. 14/207,344.
Office Action dated Aug. 29, 2014 for U.S. Appl. No. 14/152,590.
Office Action dated Sep. 9, 2016 for U.S. Appl. No. 14/081,504.
Office Action dated Sep. 9, 2016 for U.S. Appl. No. 14/207,344.
Office Action dated Sep. 11, 2017 for U.S. Appl. No. 14/832,422.
Office Action dated Sep. 23, 2016 for U.S. Appl. No. 14/152,590.
Office Action dated Sep. 24, 2014 for U.S. Appl. No. 14/031,746.
Office Action dated Sep. 27, 2016 for U.S. Appl. No. 13/827,790.
Office Action dated Sep. 28, 2017 for U.S. Appl. No. 14/207,344.
Office Action dated Oct. 6, 2016 for U.S. Appl. No. 13/360,444.
Office Action dated Oct. 6, 2016 for U.S. Appl. No. 13/742,025.
Office Action dated Oct. 7, 2019 for U.S. Appl. No. 13/360,444.
Office Action dated Oct. 7, 2019 for U.S. Appl. No. 14/152,590.
Office Action dated Oct. 10, 2014 for U.S. Appl. No. 13/742,025.
Office Action dated Oct. 15, 2015 for U.S. Appl. No. 13/827,790.
Office Action dated Oct. 20, 2017 for U.S. Appl. No. 13/826,618.
Office Action dated Oct. 26, 2016 for U.S. Appl. No. 13/742,077.
Office Action dated Nov. 2, 2015 for U.S. Appl. No. 13/742,077.
Office Action dated Nov. 17, 2016 for U.S. Appl. No. 13/829,493.
Office Action dated Nov. 17, 2017 for U.S. Appl. No. 13/360,444.
Office Action dated Nov. 18, 2016 for U.S. Appl. No. 13/826,618.
Office Action dated Nov. 20, 2015 for U.S. Appl. No. 13/826,618.
Office Action dated Nov. 21, 2017 for U.S. Appl. No. 14/152,590.
Office Action dated Dec. 18, 2015 for U.S. Appl. No. 14/081,504.
Office Action dated Dec. 28, 2017 for U.S. Appl. No. 13/827,790.
Office Action dated Dec. 29, 2017 for U.S. Appl. No. 14/081,504.
Shuttle® and CT-Core® Semi-Automatic Devices Updated to the website between Nov. 8, 2012-Jan. 24, 2013. Accessed website on Jun. 27, 2014 at http://www.healthcare.com/qb/int_radiplogy.html.
European Examination Report dated Sep. 1, 2023 for EP20190128.7.
European Examination Report dated Oct. 20, 2023 for EP21189728.5.
Office Action dated Aug. 5, 2021 for U.S. Appl. No. 13/827,790.
Arras, et al., Electrospinning of Aligned Fibers with Adjustable Orientation Using Auxiliary Electrodes, Sci. Technol. Adv. Mater., 13, 2012.
European Search Report dated Nov. 29, 2021 for EP21165437.1.
Extended European Search Report dated Jan. 7, 2022 for EP21181412.4.
Notice of Allowance dated Sep. 7, 2022 for U.S. Appl. No. 13/827,790.
Notice of Allowance dated Dec. 15, 2022 for U.S. Appl. No. 13/742,077.
Office Action dated May 12, 2022 for U.S. Appl. No. 13/827,790.
Office Action dated Nov. 9, 2022 for U.S. Appl. No. 16/877,259.
Patent Board Decision—Reversed dated Dec. 6, 2022 for U.S. Appl. No. 13/742,077.
International Search Report and Written Opinion dated Jun. 8, 2016 for PCT/US2016/019487.
International Search Report and Written Opinion dated Jun. 23, 2015 for PCT/US2013/076418.
International Search Report and Written Opinion dated Jun. 26, 2014 for PCT/US2014/024868.
International Search Report and Written Opinion dated Jul. 1, 2014 for PCT/US2014/023416.
International Search Report and Written Opinion dated Jul. 1, 2016 for PCT/US2016/020165.
International Search Report and Written Opinion dated Sep. 6, 2013 for PCT/US2013/046245.
International Search Report and Written Opinion dated Sep. 17, 2013 for PCT/US2013/060172.

International Search Report and Written Opinion dated Dec. 3, 2013 for PCT/US2013/060172.
International Search Report and Written Opinion dated Dec. 5, 2013 for PCT/US2013/060812.
Notice of Allowance dated Jan. 25, 2017 for U.S. Appl. No. 14/152,626.
Office Action dated Jan. 22, 2016 for U.S. Appl. No. 14/152,626.
Office Action dated Jan. 23, 2017 for U.S. Appl. No. 14/081,715.
Office Action dated Jan. 25, 2019 for U.S. Appl. No. 14/207,344.
Office Action dated Feb. 4, 2015 for U.S. Appl. No. 13/360,444.
Office Action dated Feb. 7, 2017 for U.S. Appl. No. 13/827,790.
Office Action dated Feb. 8, 2019 for U.S. Appl. No. 14/081,715.
Office Action dated Feb. 16, 2018 for U.S. Appl. No. 13/742,077.
Office Action dated Feb. 20, 2015 for U.S. Appl. No. 14/044,050.
Office Action dated Feb. 20, 2020 for U.S. Appl. No. 15/806,020.
Office Action dated Feb. 22, 2016 for U.S. Appl. No. 13/742,077.
Office Action dated Mar. 3, 2014 for U.S. Appl. No. 13/742,025.
Office Action dated Mar. 15, 2017 for U.S. Appl. No. 14/207,344.
Office Action dated Mar. 25, 2020 for U.S. Appl. No. 14/081,715.
Office Action dated Mar. 28, 2016 for U.S. Appl. No. 13/827,790.
Office Action dated Mar. 31, 2017 for U.S. Appl. No. 14/204,466.
Office Action dated Apr. 6, 2020 for U.S. Appl. No. 13/827,790.
Office Action dated Apr. 7, 2017 for U.S. Appl. No. 13/826,618.
Office Action dated Apr. 27, 2017 for U.S. Appl. No. 13/742,077.
Office Action dated Apr. 29, 2020 for U.S. Appl. No. 14/207,344.
Office Action dated May 1, 2020 for U.S. Appl. No. 16/035,334.
Office Action dated May 9, 2014 for U.S. Appl. No. 13/360,444.
Office Action dated May 11, 2018 for U.S. Appl. No. 13/826,618.
Office Action dated May 11, 2018 for U.S. Appl. No. 14/832,422.
Office Action dated May 19, 2017 for U.S. Appl. No. 13/742,025.
Office Action dated Jun. 1, 2016 for U.S. Appl. No. 14/134,280.
Office Action dated Jun. 9, 2016 for U.S. Appl. No. 14/152,626.
Office Action dated Jun. 15, 2018 for U.S. Appl. No. 14/207,344.
Office Action dated Jun. 19, 2017 for U.S. Appl. No. 14/081,504.
Office Action dated Jun. 23, 2017 for U.S. Appl. No. 13/829,493.
Office Action dated Jun. 28, 2018 for U.S. Appl. No. 14/081,715.
Office Action dated Jun. 29, 2017 for U.S. Appl. No. 14/081,715.
Office Action dated Jun. 30, 2016 for U.S. Appl. No. 14/081,715.
Office Action dated Jul. 2, 2014 for U.S. Appl. No. 14/044,050.
Office Action dated Jul. 11, 2019 for U.S. Appl. No. 14/081,715.
Office Action dated Jul. 12, 2017 for U.S. Appl. No. 15/053,232.
Office Action dated Jul. 13, 2018 for U.S. Appl. No. 13/827,790.
Office Action dated Jul. 26, 2017 for U.S. Appl. No. 13/827,790.
Office Action dated Jul. 26, 2018 for U.S. Appl. No. 14/152,590.
Office Action dated Jul. 29, 2015 for U.S. Appl. No. 14/152,626.
Office Action dated Jul. 30, 2020 for U.S. Appl. No. 15/806,020.
EP Examination Report dated May 28, 2019 for EP12755426.9.
European Examination Report dated Jun. 24, 2022 for EP19193202.9.
European Search Report dated Jan. 28, 2021 for EP20190128.7.
European Search Report dated Feb. 3, 2021 for EP20191283.9.
Office Action dated Feb. 26, 2015 for U.S. Appl. No. 14/152,590.
Office Action dated Apr. 26, 2020 for U.S. Appl. No. 14/207,344.
Office Action dated Jun. 8, 2016 for U.S. Appl. No. 14/044,050.
Board Decision on Appeal dated Nov. 23, 2018 for U.S. Appl. No. 14/044,050.
European Search Report dated Feb. 12, 2016 for EP13813055.4.
European Search Report dated Feb. 21, 2020 for EP19193202.9.
European Search Report dated Mar. 30, 2016 for EP13838784.0.
European Search Report dated Jun. 16, 2014 for EP14160501.4.
European Search Report dated Aug. 19, 2014 for EP12755426.9.
European Search Report dated Aug. 20, 2019 for EP14774594.7.
European Search Report dated Sep. 6, 2016 for EP14774594.7.
European Search Report dated Oct. 17, 2018 for EP16756335.2.
European Search Report dated Dec. 6, 2018 for EP13813055.4.
Extended European Search Report dated Mar. 30, 2016 for EP13838578.6.
Extended European Search Report dated Jun. 25, 2015 for EP12739348.6.
Extended European Search Report dated Jul. 26, 2016 for EP14741114.4.
International Report on Patentability dated Jul. 22, 2014 for PCT/US2013/021554.

(56)          References Cited

OTHER PUBLICATIONS

International Search Report and Written Opinion dated Apr. 3, 2014 for PCT/US2013/076418.
International Search Report and Written Opinion dated Apr. 26, 2013 for PCT/US2013/021554.
International Search Report and Written Opinion dated Apr. 27, 2015 for PCT/US2015/011746.
International Search Report and Written Opinion dated Apr. 30, 2015 for PCT/US2015/012002.
International Search Report and Written Opinion dated May 1, 2014 for PCT/US2014/012043.
International Search Report and Written Opinion dated May 23, 2012 for PCT/US2012/023006.
Notice of Allowance dated Jan. 30, 2020 for U.S. Appl. No. 14/152,590.
Notice of Allowance dated Feb. 6, 2020 for U.S. Appl. No. 13/360,444.
Notice of Allowance dated Apr. 3, 2018 for U.S. Appl. No. 14/081,504.
Notice of Allowance dated Apr. 14, 2015 for U.S. Appl. No. 14/031,746.
Notice of Allowance dated May 9, 2018 for U.S. Appl. No. 15/053,232.
Notice of Allowance dated Jul. 11, 2016 for U.S. Appl. No. 13/826,618.
Notice of Allowance dated Aug. 7, 2020 for U.S. Appl. No. 14/207,344.
Notice of Allowance dated Sep. 3, 2015 for U.S. Appl. No. 13/787,327.
Notice of Allowance dated Oct. 4, 2017 for U.S. Appl. No. 14/204,466.
Notice of Allowance dated Oct. 9, 2019 for U.S. Appl. No. 13/826,618.
Office Action dated Jan. 2, 2019 for U.S. Appl. No. 13/360,444.
Office Action dated Jan. 2, 2019 for U.S. Appl. No. 14/152,590.
Office Action dated Jan. 10, 2019 for U.S. Appl. No. 13/826,618.
Office Action dated Jan. 12, 2016 for U.S. Appl. No. 14/152,590.
Office Action dated Jan. 13, 2015 for U.S. Appl. No. 13/827,790.
Office Action dated Jan. 14, 2019 for U.S. Appl. No. 13/827,790.
Office Action dated Jan. 16, 2018 for U.S. Appl. No. 14/081,715.
Office Action dated Jan. 17, 2019 for U.S. Appl. No. 14/832,422.
European Search Report dated Dec. 23, 2020 for EP20199088.4.
Notice of Allowance dated Feb. 24, 2021 for U.S. Appl. No. 16/035,334.
Notice of Allowance dated Dec. 14, 2020 for U.S. Appl. No. 14/081,715.
Notice of Allowance dated Dec. 15, 2020 for U.S. Appl. No. 15/806,020.
Office Action dated Dec. 23, 2020 for U.S. Appl. No. 13/827,790.
Yasuda, et al., Contact Angle of Water on Polymer Surfaces, Am Chem, Langmuir, vol. 10 No. 7 ,1994.
Office Action dated Nov. 29, 2023 for U.S. Appl. No. 16/895,975.
Office Action dated Dec. 19, 2023 for U.S. Appl. No. 16/877,259.
Office Action dated Dec. 29, 2023 for U.S. Appl. No. 17/068,627.
European Examination Report dated Mar. 15, 2024 for EP21181412.4.
Office Action dated Apr. 3, 2024 for U.S. Appl. No. 16/877,259.
Office Action dated May 7, 2024 for U.S. Appl. No. 17/652,552.
European Examination Report dated Jan. 2, 2024 for EP21165437.1.
European Examination Report fated Oct. 20, 2023 for EP21189728.5.
Office Action dated Jan. 24, 2024 for U.S. Appl. No. 17/652,552.

European Examination Report dated Jun. 4, 2024 for EP20199088.4.
Office Action dated Jun. 14, 2024 for U.S. Appl. No. 16/895,975.
Office Action dated Jul. 2, 2024 for U.S. Appl. No. 17/341,038.
Office Action dated Jul. 12, 2024 for U.S. Appl. No. 18/170,364.
Office Action dated Jul. 16, 2024 for U.S. Appl. No. 17/068,627.
European Search Report dated Nov. 5, 2024 for EP19193202.9.
European Search Report dated Oct. 11, 2024 for EP24173827.7.
European Search Report dated Dec. 13, 2024 for EP22760630.8.
Office Action dated Jan. 16, 2025 for U.S. Appl. No. 18/170,364.
Office Action dated Feb. 7, 2025 for U.S. Appl. No. 17/516,530.
Office Action dated Feb. 14, 2025 for U.S. Appl. No. 17/068,627.
European Examination Report dated Mar. 24, 2025 for EP21189728.5.
European Examination Report dated Apr. 8, 2025 for EP21181412.4.
Notice of Allowance dated Feb. 26, 2025 for U.S. Appl. No. 17/652,552.
Notice of Allowance dated Feb. 27, 2025 for U.S. Appl. No. 16/877,259.
Notice of Allowance dated Apr. 10, 2025 for U.S. Appl. No. 16/877,259.
Office Action dated Mar. 5, 2025 for U.S. Appl. No. 17/341,038.
Office Action dated Apr. 10, 2025 for U.S. Appl. No. 17/515,236.
European Search Report dated Apr. 16, 2025 for EP21165437.1.
Office Action dated Oct. 24, 2024 for U.S. Appl. No. 17/652,552.
Final Office Action dated Nov. 5, 2024 for U.S. Appl. No. 16/877,259.
Office Action dated Oct. 22, 2024 for U.S. Appl. No. 16/895,975.
European Examination Report dated Aug. 21, 2025 for EP21165437.1.
Notice of Allowance dated May 28, 2025 for U.S. Appl. No. 17/068,627.
Notice of Allowance dated Jun. 24, 2025 for U.S. Appl. No. 17/341,038.
Notice of Allowance dated Jul. 1, 2025 for U.S. Appl. No. 17/068,627.
Notice of Allowance dated Jul. 22, 2025 for U.S. Appl. No. 17/341,038.
Office Action dated Jun. 11, 2025 for U.S. Appl. No. 17/516,530.
Office Action dated Jul. 7, 2025 for U.S. Appl. No. 16/895,975.
Office Action dated Aug. 12, 2025 for U.S. Appl. No. 17/516,069.
Office Action dated Aug. 27, 2025 for U.S. Appl. No. 18/151,885.
Office Action dated Aug. 28, 2025 for U.S. Appl. No. 18/170,364.
Notice of Allowance dated Sep. 3, 2025 for U.S. Appl. No. 17/068,627.
European Search Report dated Aug. 26, 2025 for EP19193202.9.
Office Action dated Sep. 17, 2025 for U.S. Appl. No. 17/515,236.
Notice of Allowance dated Jan. 22, 2026 for U.S. Appl. No. 17/515,236.
Office Action dated Dec. 4, 2025 for U.S. Appl. No. 17/516,530.
European Examination Report dated Oct. 13, 2025 for EP22760630.8.
European Search Report dated Oct. 17, 2025 for EP25175405.7.
Office Action dated Oct. 21, 2025 for U.S. Appl. No. 16/895,975.
Office Action dated Oct. 28, 2025 for U.S. Appl. No. 18/068,181.
Notice of Allowance dated Feb. 4, 2026 for U.S. Appl. No. 17/515,236.
Office Action dated Feb. 11, 2026 for U.S. Appl. No. 18/170,364.
Notice of Allowance dated Mar. 6, 2026 for U.S. Appl. No. 17/516,069.
Notice of Allowance dated Mar. 19, 2026 for U.S. Appl. No. 16/895,975.
Office Action dated Mar. 24, 2026 for U.S. Appl. No. 18/151,885.

* cited by examiner

ROTATIONAL SPUN MATERIAL COVERED MEDICAL APPLIANCES AND METHODS OF MANUFACTURE

RELATED APPLICATIONS

This application is a continuation of U.S. patent application Ser. No. 14/832,422, filed on Aug. 21, 2015 and titled, "Rotational Spun Material Covered Medical Appliances and Methods of Manufacture," which is a divisional application of U.S. patent application Ser. No. 13/742,025, filed on Jan. 15, 2013 and titled "Rotational Spun Material Covered Medical Appliances and Methods of Manufacture," now issued as U.S. Pat. No. 9,987,833. U.S. patent application Ser. No. 13/742,025, in turn, claims priority to the following applications: U.S. Provisional Application No. 61/587,088 filed on Jan. 16, 2012 titled Force Spun Fibers and Medical Appliances; U.S. Provisional Application No. 61/637,693 filed on Apr. 24, 2012 titled Rotational Spun Material Coated Medical Appliances and Method of Manufacture; and U.S. Provisional Application No. 61/672,633 filed on Jul. 17, 2012 titled Rotational Spun Material Coated Medical Appliances and Method of Manufacture. Each priority document listed above is hereby incorporated by reference in its entirety.

TECHNICAL FIELD

The present disclosure relates generally to medical devices. More specifically, the present disclosure relates to medical appliances or other prostheses, particularly those made of, constructed from, covered or coated with rotational spun materials including polymers such as polytetrafluoroethylene (PTFE).

BRIEF DESCRIPTION OF THE DRAWINGS

The patent or application file contains at least one drawing executed in color. Copies of this patent or patent application publication with color drawings will be provided by the Office upon request and payment of the necessary fee.

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 21A is an SEM (at 170×) of a rotational spun material spun at 4500 RPM.

FIG. 21B is an SEM (at 170×) of a rotational spun material spun at 5000 RPM.

FIG. 21C is an SEM (at 170×) of a rotational spun material spun at 5500 RPM.

FIG. 21D is an SEM (at 170×) of a rotational spun material spun at 6000 RPM.

DETAILED DESCRIPTION

Figure 1A:
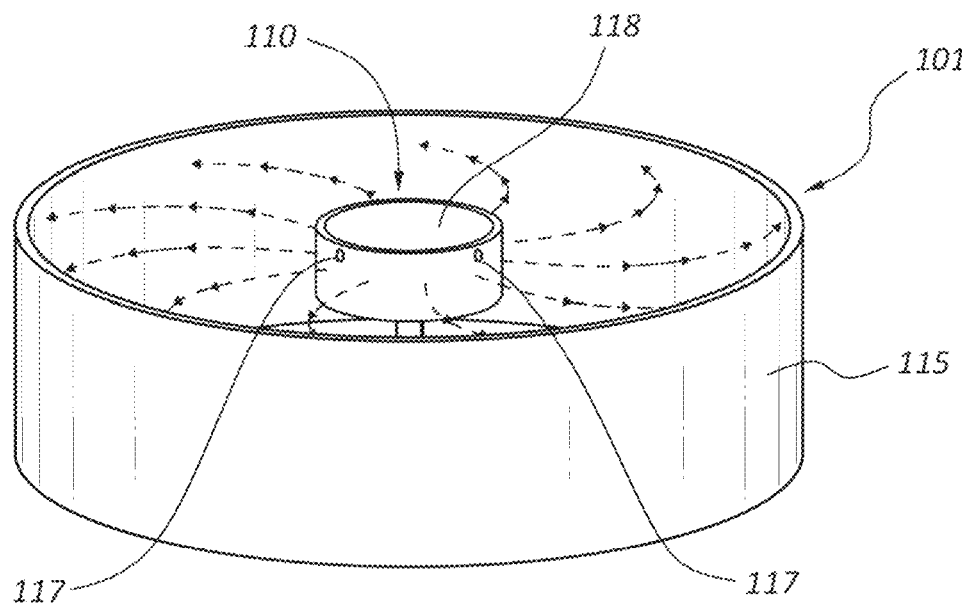
FIG. 1A is a perspective view of a rotational spinning apparatus.

Medical appliances may be deployed in various body lumens for a variety of purposes. Stents may be deployed, for example, in the central venous system for a variety of therapeutic purposes including the treatment of occlusions within the lumens of that system. The current disclosure may be applicable to stents or other medical appliances designed for the central venous ("CV") system, peripheral vascular ("PV") stents, abdominal aortic aneurism ("AAA") stents, bronchial stents, esophageal stents, biliary stents, coronary stents, gastrointestinal stents, neuro stents, thoracic aortic endographs, or any other stent or stent graft. Further, the present disclosure may be equally applicable to other prosthesis such as grafts. Any medical appliance comprised of materials herein described may be configured for use or implantation within various areas of the body, including vascular, cranial, thoracic, pulmonary, esophageal, abdominal, or ocular application. Examples of medical appliances within the scope of this disclosure include, but are not limited to, stents, vascular grafts, stent grafts, cardiovascular patches, reconstructive tissue patches, hernia patches, general surgical patches, heart valves, sutures, dental reconstructive tissues, medical device coverings and coatings, gastrointestinal devices, blood filters, artificial organs, ocular implants, and pulmonary devices, including pulmonary stents. For convenience, many of the specific examples included below reference stents. Notwithstanding any of the particular medical appliances referenced in the examples or disclosure below, the disclosure and examples may apply analogously to any prostheses or other medical appliance.

As used herein, the term stent refers to a medical appliance configured for use within a bodily structure, such as within a body lumen. A stent may comprise a scaffolding or support structure, such as a frame, and/or a covering. Thus, as used herein, "stent" refers to both covered and uncovered scaffolding structures.

It will be readily understood that the components of the embodiments as generally described and illustrated in the Figures herein could be arranged and designed in a wide variety of different configurations. Thus, the following more detailed description of various embodiments, as represented in the Figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "proximal" and "distal" are used herein to refer to opposite locations on a stent or another medical appliance. The proximal end of an appliance is defined as the end closest to the practitioner when the appliance is disposed within a deployment device which is being used by the practitioner. The distal end is the end opposite the proximal end, along the longitudinal direction of the appliance, or the end furthest from the practitioner. It is understood that, as used in the art, these terms may have different meanings once the appliance is deployed (i.e., the "proximal" end may refer to the end closest to the head or heart of the patient depending on application). For consistency, as used herein, the ends labeled "proximal" and "distal" prior to deployment remain the same regardless of whether the appliance is deployed. The longitudinal direction of a stent is the direction along the axis of a generally tubular stent. In embodiments where a stent or another appliance is composed of a metal wire structure coupled to one or more layers of a film or sheet like components, such as a polymer layer, the metal structure is referred to as the "scaffolding" or "frame," and the polymer layer as the "covering" or "coating." The terms "covering" or "coating" may refer to a single layer of polymer, multiple layers of the same polymer, or layers comprising distinct polymers used in combination. Furthermore, as used herein, the terms "covering" and "coating" refer only to a layer or layers which are coupled to a portion of the scaffold; neither term requires that the entire scaffold be "covered" or "coated." In other words, medical appliances wherein portion of the scaffold may be covered and a portion remain bare, are within the scope of this disclosure. Finally, any disclosure recited in connection with coverings or coatings may analogously be applied to medical devices comprising one or more "covering" layers with no associated frame or other structure. For example, a hernia patch comprising any of the materials described herein as "coatings" or "coverings" is within the scope of this disclosure regardless of whether the patch further comprising a frame or other structure.

Medical device coverings may comprise multilayered constructs, comprised of two or more layers which may be serially applied. Further, multilayered constructs may comprise nonhomogeneous layers, meaning adjacent layers have differing properties. Thus, as used herein, each layer of a multilayered construct may comprise a distinct layer, either due to the distinct application of the layers or due to differing properties between layers.

Additionally, as used herein, "tissue ingrowth" or "cellular penetration" refer to any presence or penetration of a biological or bodily material into a component of a medical appliance. For example, the presence of body tissues (e.g. collagen, cells, and so on) within a opening or pore of a layer or component of a medical appliance comprises tissue ingrowth into that component. Further, as used herein, "attachment" of tissue to a component of a medical appliance refers to any bonding or adherence of a tissue to the appliance, including indirect bonds. For example, tissue of some kind (e.g. collagen) may become attached to a stent covering (including attachment via tissue ingrowth) and another layer of biologic material (such as endothelial cells) may, in turn, adhere to the first tissue. In such instances, the second biologic material (endothelial cells in the example), and the tissue (collagen in the example) are "attached" to the stent covering.

Furthermore, through the present disclosure, certain fibrous materials (such as rotational spun materials) may be referred to as inhibiting or promoting certain biological responses. These relative terms are intended to reference the characteristics of the fibrous materials with respect to non-fibrous materials or coatings. Examples of non-fibrous coatings include non-fibrous PTFE sheets, other similarly formed polymers, and the like. Examples of fibrous coatings include rotational spun PTFE, electrospun PTFE, expanded PTFE, and other similarly formed polymers or materials. Examples of spun fibrous coatings include rotational spun PTFE, electrospun PTFE, and other similarly formed polymers or materials, and exclude expanded PTFE.

Lumens within the circulatory system are generally lined with a single layer (monolayer) of endothelial cells. This lining of endothelial cells makes up the endothelium. The endothelium acts as an interface between blood flowing through the lumens of the circulatory system and the inner walls of the lumens. The endothelium, among other functions, reduces or prevents turbulent blood flow within the lumen. The endothelium plays a role in many aspects of vascular biology, including atherosclerosis, creating a selective barrier around the lumen, blood clotting, inflammation, angiogenesis, vasoconstriction, and vasodilation.

A therapeutic medical appliance which includes a covering of porous or semi-porous material may permit the formation of an endothelial layer onto the porous surface of the blood contact side of the medical device. Formation of an endothelial layer on a surface, or endothelialization, may increase the biocompatibility of an implanted device. For example, a stent which permits the formation of the endothelium on the inside diameter (blood contacting surface) of the stent may further promote healing at the therapeutic region and/or have longer term viability. For example, a stent coated with endothelial cells may be more consistent with the surrounding body lumens, thereby resulting in less turbulent blood flow or a decreased risk of thrombosis, or the formation of blood clots. A stent which permits the formation of an endothelial layer on the inside surface of the stent may therefore be particularly biocompatible, resulting in less trauma at the point of application, fewer side effects, and/or longer term device viability. Medical appliances including a covering of porous or semi-porous material may be configured to inhibit or reduce inflammatory responses by the body toward the tissue contacting side of the medical appliance, for example. Mechanisms such as an inflammatory response by the body toward the medical appliance may stimulate, aggravate, or encourage negative outcomes, such as neointimal hyperplasia. For example, a device configured to permit tissue ingrowth and/or the growth or attachment of endothelial cells onto the blood contacting side of the device may reduce the likelihood of negative flow characteristics and blood clotting. Similarly, a device so configured may mitigate the body's inflammatory response toward the material on, for example, the tissue or non-blood contacting side of the device. By modulating the evoked inflammatory response, negative outcomes such as the presence of bioactive inflammatory macrophages and foreign body giant cells may be reduced. This may aid in minimizing the chemical chain of responses that may encourage fibrous capsule formation surrounding the device and events stimulating neointimal hyperplasia.

Rotational spun materials, such as those described herein, may be used to comprise portions of medical appliances, such as stents, patches, grafts, and so forth. The present disclosure is applicable to any implantable medical appliance, notwithstanding any specific examples included below. In other words, though particular medical appliances, such as stents or patches, may be referenced in the disclosure and examples below, the disclosure is also analogously applicable to other medical appliances, such as those which comprise a covering or layer of polymeric material.

In some embodiments, rotational spun nanofibers (and/or microfibers) may be configured to permit interaction with nano-scale (and/or micro-scale) body structures, such as endothelial cells. Rotational spinning refers generally to processes involving the expulsion of flowable material from one or more orifices, the material forming fibers which are subsequently deposited on a collector. Examples of flowable materials include dispersions, solutions, suspensions, liquids, molten or semi-molten material, and other fluid or semi-fluid materials. In some embodiments, the rotational spinning processes are completed in the absence of an electric field.

For example, one embodiment of a rotational spinning process comprises loading a polymer solution or dispersion into a cup or spinneret configured with orifices on the outside circumference of the spinneret. The spinneret is then rotated, causing (through a combination of centrifugal and hydrostatic forces, for example) the flowable material to be expelled from the orifices. The material may then form a "jet" or "stream" extending from the orifice, with drag forces tending to cause the stream of material to elongate into a small diameter fiber. The fibers may then be deposited on a collection apparatus. Exemplary methods and systems for rotational spinning can be found in U.S. Patent Publication No. US2009/0280325, titled "Methods and Apparatuses for Making Superfine Fibers," which is herein incorporated by reference in its entirety.

Rotational spinning may be configured to create mats, tubes, or other structures comprised of elongate fibers, including nanofibers (i.e. fibers which are smaller than one micron in diameter) or microfibers (i.e. fibers which are between one micron and one millimeter in diameter). In some instances the fibers may be randomly disposed, while in other embodiments the alignment or orientation of the fibers may be somewhat controlled or follow a general trend or pattern. Regardless of any pattern or degree of fiber alignment, as the fibers are deposited on a collector or on previously deposited fibers; the fibers are not woven, but rather serially deposited on the collector or other fibers. Because rotational spinning may be configured to create a variety of structures, as used herein, the terms "mat" or "non-woven mat or material" is intended to be broadly construed as referring to any such rotational spun structure, including tubes, spheres, and so on.

The present disclosure relates to medical appliances which may have, in certain embodiments, metal scaffolding covered with at least one layer of rotational spun material, such as rotational spun polytetrafluoroethylene (PTFE). Additionally, the present disclosure relates to medical appliances formed of rotational spun materials which may not have scaffolding structures or have scaffolding structures which are not made of metal. It will be appreciated that, though particular structures and coverings are described below, any feature of the scaffolding or covering described below may be combined with any other disclosed feature without departing from the scope of the current disclosure.

FIGS. 1A, 1B, 2A, and 2B schematically illustrate certain embodiments of rotational spinning apparatuses. FIGS. 3A and 3B illustrate an embodiment of a covered medical appliance. FIGS. 4A-4E illustrate certain steps in a process of manufacturing a multi-layered construct of rotational spun materials. FIG. 5 illustrates an embodiment of a medical appliance which includes cuffs at each end of a stent. FIGS. 6-10 illustrate aspects of frames configured for use in connection with medical appliances. Finally, FIGS. 11A-19 are scanning electron micrographs (SEMs) of exemplary rotational spun materials. Again, regardless of whether a medical appliance illustrated in any particular figure is illustrated with a particular covering or coating, or without any covering or coating at all, any embodiment of a medical appliance may be configured with any of the combinations of coverings or coatings shown or described herein.

FIG. 1A illustrates a rotational spinning apparatus 101. This Figure, as well as FIGS. 1B, 2A, and 2B, discussed below, are intended to schematically illustrate the operation of a rotational spinning apparatus, and not meant to limit the particular structure, shape, or arrangement of rotational spinning apparatus components within the scope of this disclosure. The illustrated apparatus 101 comprises a spinneret 110 disposed near the center of a generally circular collector 115. In the illustrated embodiment the collector 115 forms a ring around the spinneret 110. The spinneret 110 further comprises orifices 117 located around the circumference of the spinneret 110 and a reservoir 118.

The apparatus 101 may be utilized to create a mat of rotational spun fibers deposited on the collector 115. In some embodiments, the collector 115 may be configured such that structures such as rods, tubes, or spheres of rotational spun fibers are created.

In some embodiments, the apparatus 101 may be utilized to create a mat of rotational spun fibers by first filling the reservoir 118 with a flowable material. In some instances polymer dispersions, including aqueous dispersions or polymer solutions may be used. The spinneret 110 may then be rotated such that the dispersion, or other flowable material, is forced out of the orifices 117 as illustrated by the arrows in FIG. 1A. Molecules, including polymer chains, may tend to disentangle and/or align as the material is forced through the orifice. Additionally, in some embodiments the orifice 117 comprises a needle or nozzle that extends from the outside circumference of the spinneret 110. Still further, in some embodiments the orifice 117 may comprise a cannula configured with a quick connection, such as a luer connection, allowing for rapid exchange of various cannula sizes.

As the dispersion is expelled from the reservoir 118, drag or other aerodynamic forces acting on the stream or jet of material may cause the stream of dispersion to elongate and bend, forming a relatively small diameter fiber of material. In some instances drag may be a shear force with respect to the stream. Additionally, certain components of the dispersion, such as the dispersion medium or solvent, may partially or fully evaporate as the material is drawn into fibers. In embodiments utilizing flowable materials which have no solvent, such as molten material, there may be no evaporation as the material is drawn into fibers.

The fibers eventually contact, and are deposited on, the collector 115. The combination of forces described above may interact as the fibers are deposited, causing the fibers to be disposed in random patterns on the collector 115. In some embodiments, air currents may be introduced (for example through the use of fans) to partially control the deposition of the fibers on the collector 115.

In embodiments utilizing certain flowable materials, the fibers may then be removed from the collector 115 and sintered, or sintered then removed. For example, sintering may be applicable to PTFE fibers, including PTFE fibers spun from a dispersion. The sintering process may set or bond the structure of the mat and remove any remaining water or other dispersion medium or solvent.

In some embodiments, the mat may be treated at a first temperature to remove solvents and a second temperature to sinter the mat. For example, a PTFE mat spun from an aqueous dispersion may be first treated at a temperature below the sintering temperature of PTFE in order to remove any remaining water. For example, the mat may be heated to about 200 degrees C. to remove any remaining water in the mat. Further, other materials such as solvents or fiberizing agents may be evaporated or otherwise driven off at this stage. In some embodiments—as further detailed below—a PTFE dispersion may be mixed with polyethylene oxide (PEO) prior to rotational spinning the mat. As also discussed in the examples below, concentrations of PEO to 60 wt % PTFE dispersion from about 0.04 g/ml to about 0.12 g/ml, including from about 0.06 g/ml to about 0.08 g/ml may be used in some embodiments. In some instances, very high or very low concentrations of PEO may lead to shrinkage during sintering or sputtering during rotational spinning of the material.

Treating the spun mat at temperatures such as 200 degrees C. may force off remaining PEO as well as water. In some embodiments the PTFE mat may then be sintered at about 385 degrees C. In other embodiments, PTFE sintering may be completed at temperatures from about 360 degrees C. to about 400 degrees C., and/or at temperatures in excess of the crystalline melt point of the PTFE (about 342 degrees C.). In other instances the mat may only be heated to the sintering temperature, removing the remaining water and/or PEO while simultaneously sintering the PTFE. Additionally or alternatively, in some embodiments solvents or other materials may be removed by rinsing the mat.

Sintering may set the structure of the mat even if the temperature at which the material is sintered is not sufficient to cause cross linking of the polymer chains. PTFE sintering may create solid, void free, PTFE fibers.

Figure 1B:
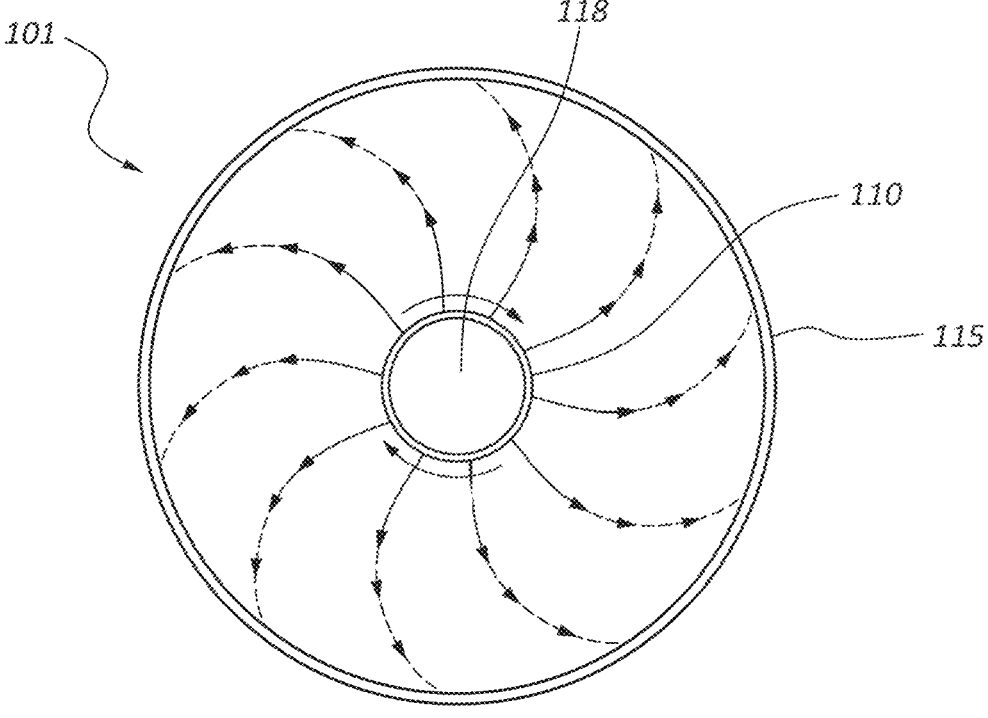
FIG. 1B is a top view of the rotational spinning apparatus of FIG. 1A.

FIG. 1B is a top view of the rotational spinning apparatus 101 of FIG. 1A, illustrating the spinneret 110, the collector 115, and the reservoir 118. In the illustration of FIG. 1B potential arced paths of the streams of material interacting with drag forces are illustrated by arrows and dotted lines. These lines are exemplary and not intended to show the precise path of the fibers. In many embodiments, the fibers may loop completely around the spinneret 110 before contacting the collector 115, including embodiments where the fiber path encircles the spinneret 110 more than one time before contacting the collector 115.

The distance between the spinneret 110 and the collector 115 may impact the diameter of the fibers. In some embodiments, the longer the fibers are drawn out before contacting the collector 115, the smaller the resulting fiber diameters. Similarly, smaller distances may be configured to produce larger diameter fibers.

Processes such as the exemplary process described above may be utilized to create structures comprised of small diameter fibers, including nanofibers. The fiber mat may then be incorporated into a medical appliance configured for implantation in the human body. Some such structures, including nanofiber structures, may be configured to permit tissue ingrowth and/or endothelial growth or attachment on the mat. For example the mat may be configured with openings within the fibers or similar structures configured to permit interaction with tissue and/or cells. As further detailed below, the percent porosity of a fiber mat, the thickness of the mat, and the diameter of the fibers comprising the mat may each be configured to create a fiber mat with desired properties, including mats that tend to permit or resist tissue ingrowth and/or endothelial growth or attachment.

A number of variables may be controlled to affect the properties of a rotational spun mat. Some of these variables include: the rotational speed of the spinneret; the viscosity of the solution, dispersion, or other flowable material; the temperature of the spinneret; introduced air currents; the thickness of the mat; and so on. In the case of fibers spun from molten material, the melt flow index (MFI) of the material may also impact the nature of the spun mat. In some embodiments, materials with an MFI of from about 1 g/10 min to about 5000 g/10 min, including from about 200 g/10 min to about 1500 g/10 min and from about 10 g/10 min to about 30 g/10 min, will tend to form fibers when spun.

In other embodiments a rotational spun mat may be configured to resist tissue ingrowth into or through the mat. In such embodiments, the mat may be configured with very small pores, or essentially no pores at all, thus preventing tissue ingrowth into or through the mat. Certain medical appliances may be constructed partially of rotational spun materials configured to permit tissue ingrowth and/or endothelial growth or attachment and partially of rotational spun materials configured to resist tissue ingrowth and/or attachment. Characteristics of the rotational spun fiber mat, such as porosity and average pore size, may be controlled during the rotational spinning process to create certain mats which permit tissue ingrowth and/or endothelial growth or attachment and other mats which resist or are impermeable to tissue ingrowth and/or attachment.

In some embodiments, a PTFE dispersion may be used to rotational spin a mat or another structure comprised of PTFE nanofibers. Furthermore, in some exemplary embodiments PEO may be added to the PTFE dispersion prior to rotational spinning the material. The PEO may be added as a fiberizing agent, to aid in the formation of PTFE fibers within the dispersion or during the process of rotational spinning the material. In some instances the PEO may more readily dissolve in the PTFE dispersion if the PEO is first mixed with water. In some examples this increased solubility may reduce the time needed to dissolve PEO in a PTFE dispersion from as long as multiple days to as little as 30 minutes. After the material is rotational spun onto a collector, the material may then be sintered as further described below. In some instances the sintering process will tend to set or harden the structure of the PTFE. Furthermore, as described above, sintering may also eliminate the water and PEO, resulting in a mat of substantially pure PTFE. Additionally, as also described above, the mat may first be heat treated at a temperature below the sintering temperature of the PTFE, in order to remove water and/or PEO from the mat. In some embodiments this step may be completed at about 200 degrees C.

The water, PEO, and PTFE amounts may be controlled to optimize the viscosity, PEO/PTFE ratio, or other properties of the mixture. In some instances adding water to the PEO before mixing with the PTFE dispersion may aid in reducing the number of solid chunks in the mixture, lower the preparation time for the mixtures, and reduce the time needed for the combined mixture to solubilize.

A variety of materials may be rotational spun to form structures for use in medical appliances. Exemplary materials which may be rotational spun for use in implantable appliances include PTFE, fluorinated ethylene propylene (FEP), Dacron or Polyethylene terephthalate (PET), polyurethanes, polycarbonate polyurethanes, polypropylene, Pebax, polyethylene, biological polymers (such as collagen, fibrin, and elastin), and ceramics.

Furthermore, additives or active agents may be integrated with the rotational spun materials, including instances where the additives are directly rotational spun with other materials. Such additives may include radiopaque materials such as bismuth oxide, antimicrobial agents such as silver sulfadiazine, antiseptics such as chlorhexidine or silver and anticoagulants such as heparin. Organic additives or components may include fibrin and/or collagen. In some embodiments, a layer of drugs or other additives may be added to a rotational spun appliance during manufacture. Additionally, some appliances may be constructed with a combination of synthetic components, organic components, and/or active ingredients including drugs, including embodiments wherein an appliance is comprised of alternating layers of these materials. Moreover, in some embodiments a medical appliance may consist of layers of rotational spun materials configured to control the release of a drug or another active layer disposed between such layers. Active layers or ingredients such as drugs or other active agents may be configured to reduce or otherwise modify or influence the biological response of the body to the implantation of the medical appliance.

Additionally, in some embodiments the material supplied to the reservoir 118 may be continuously supplied (for example by a feed line), including embodiments where the reservoir is pressurized or supplied by a pressurized source. Further, in some embodiments the material may be heated near or above its melting point prior to rotational spinning, including embodiments wherein the material is melted and not dispersed in a solvent. Thus, in some embodiments, rotational spinning molten material does not include the use of solvents; therefore there is no need to remove solvents from the mat at a later step in the process. In some instances the material may be supplied to the reservoir as pellets which are heated and melted within the reservoir.

Still further, in some instances the collector 115 may have an electrostatic charge. Additionally, in some embodiments rotational spun structures may be combined with electrospun structures, including embodiments where some layers of material are rotational spun and some electrospun, but both deposited on the same substrate or construct. Electrospinning, and its use in connection with medical appliances, is described in U.S. patent application Ser. No. 13/360,444, filed on Jan. 27, 2012 and titled "Electrospun PTFE Coated Stent and Method of Use," which is hereby incorporated by reference in its entirety.

Figure 2A:
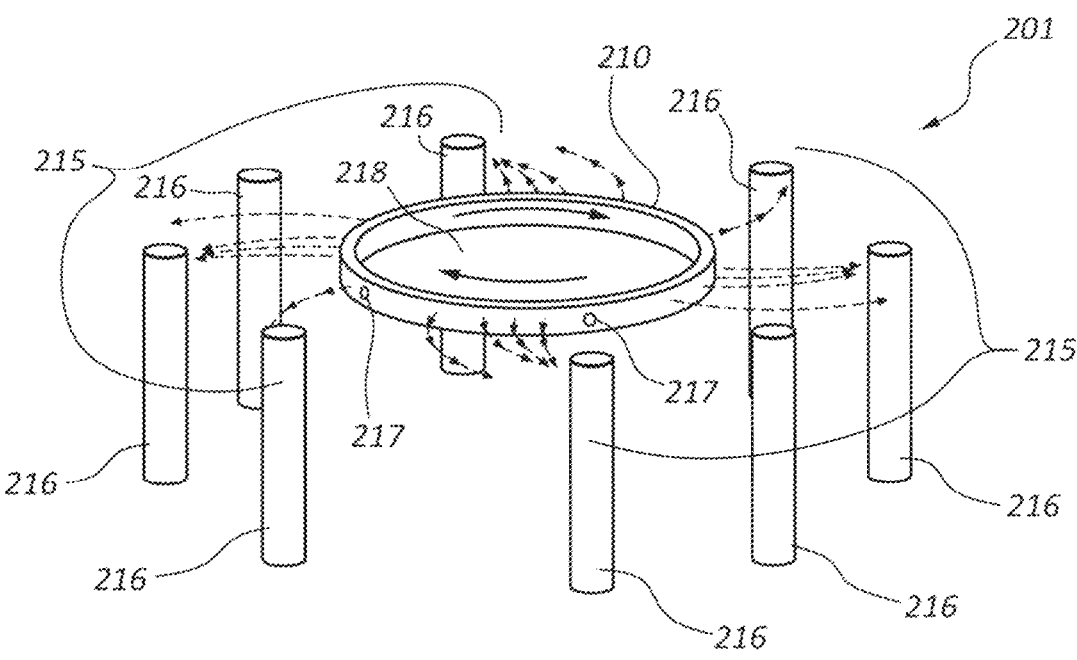
FIG. 2A is a perspective view of another embodiment of a rotational spinning apparatus.
Figure 2B:
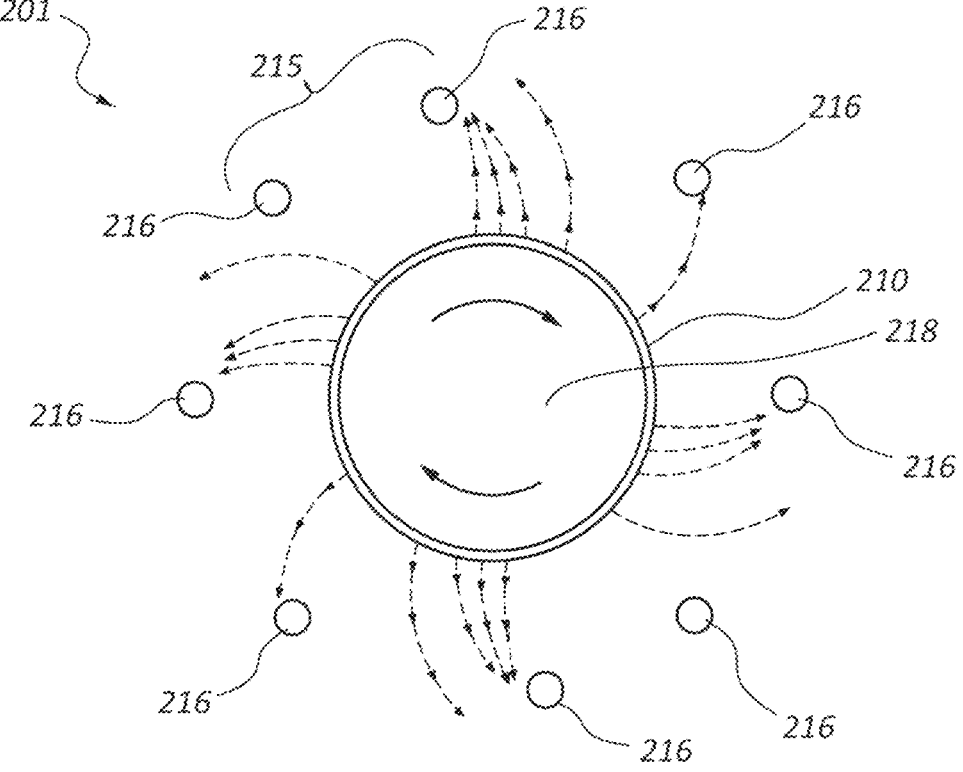
FIG. 2B is a top view of the rotational spinning apparatus of FIG. 2A.
Figure 3A:
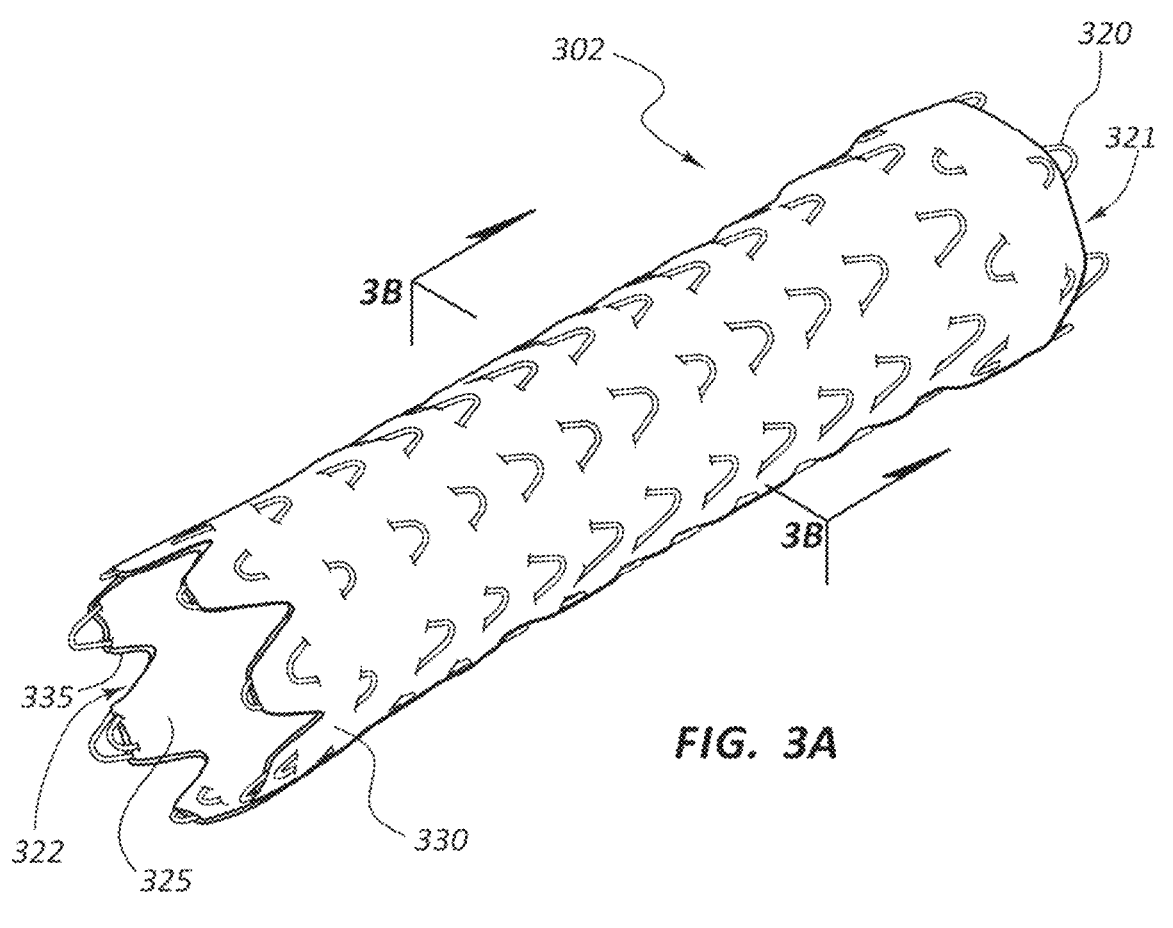
FIG. 3A is a perspective view of a covered stent.
Figure 3B:
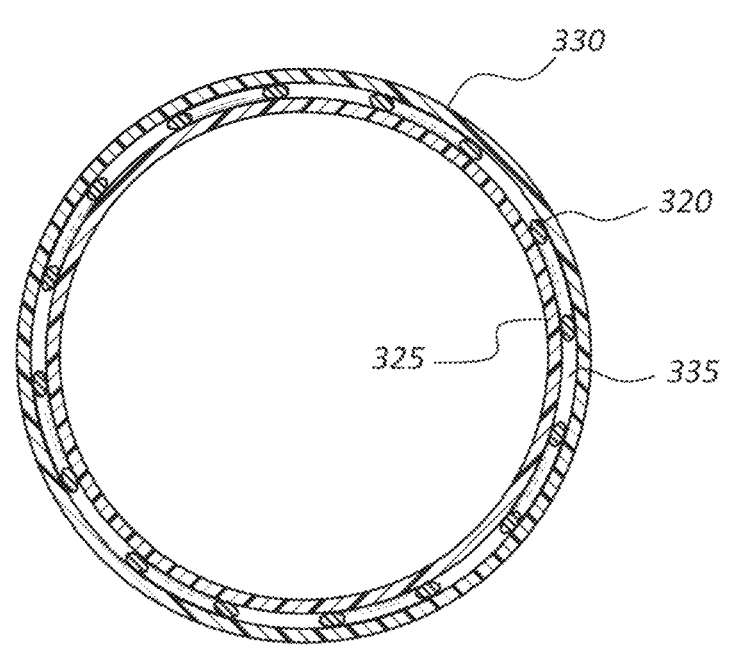
FIG. 3B is a cross sectional view of the covered stent of FIG. 3A taken through line 3B-3B.

Referring specifically to FIGS. 2A and 2B, another schematic embodiment of a rotational spinning apparatus 201 is illustrated. FIGS. 2A and 2B illustrate an apparatus analogous to that shown in FIGS. 1A and 1B. It will be appreciated by one of skill in the art having the benefit of this disclosure that analogous components of the two apparatuses may be interchangeable and that disclosure provided in connection with each embodiment may be applicable to the other and vice versa.

FIG. 2A is a perspective view of the rotational spinning apparatus 201 while FIG. 2B is a top view of the same. The rotational spinning apparatus 201 includes a spinneret 210 comprising a reservoir 218 and orifices 217. As compared to the apparatus 101 of FIGS. 1A and 1B, in the embodiment of FIGS. 2A and 2B the collector 115 is configured as a plurality of cylindrical mandrels 216. Thus in FIGS. 2A and 2B the plurality of mandrels 216 are collectively designated as a collector 215, but individually designated by the numeral 216. The term "collector" as used in connection with FIGS. 1A-2B, and indicated by numerals 115 and 215, is intended to broadly refer to any collection device or apparatus without defining a particular size, shape, or orientation. For example, in some embodiments the collector may be configured as a ring, such as the collector 115 illustrated in FIGS. 1A and 1B. In other embodiments the collector 215 may be a plurality of cylinders as shown in FIGS. 2A and 2B. In still other embodiments, the collector may comprise a rotating belt (not shown), configured to facilitate rotational spinning of a continuous sheet of material.

Embodiments configured to form a continuous sheet of rotational spun material may be configured to produce mats, including mats from about one meter to about 9 meters in width, such as mats of about 3 meters in width. Also mats from about one foot wide to about one meter wide (as well as larger or smaller mats) may be formed. In some instances, a sintering oven may be positioned such that as the mat moves away from the spinneret (on the belt) the mat enters the oven and is sintered. The sintered mat may then be collected onto a spool. Further, in some embodiments, the entire spool may then be cut into smaller widths, forming strips of material. For example, strips from about 0.1 inch wide to about 2 inches wide may be formed. Such strips may be utilized for the construction of tubular appliances by wrapping the strips around a mandrel. The strips may overlap and/or may be wound such that the tube formed does not have a distinct seam along the length of the tube. In some instances, the mat may be wound in multiple layers around the mandrel. Further, the mat formed may be relatively thin, or film-like. The thickness of the covering formed on the mandrel (and other characteristics such as porosity) may be controlled by the number of layers of film wound onto the mandrel.

In some embodiments, rotational spun tubular medical devices, such as stents, may comprise one or multiple bifurcations or branches. Thus, medical devices which comprise a single lumen which splits or bifurcates into two or more lumens are within the scope of this disclosure. Likewise, medical appliances comprising a main lumen with one or multiple branch lumens extending from the wall of the main lumen are within the scope of this disclosure. For example, a thoracic stent—configured for deployment within the aorta—may comprise a main lumen configured to be disposed in the aorta and branch lumens configured to extend into side branch vessels originating at the aorta. Similarly, in some embodiments such stents may alternately be configured with access holes in the main lumen configured to allow access (possibly for additional stent placement) and flow from the main vessel to any branch vessels extending there from.

In some embodiments, a bifurcated medical appliance may be manufactured by first creating a bifurcated mandrel in which the bifurcated mandrel portions are removable from the portion of the mandrel coinciding with the main lumen. The leg or branch portions of the mandrel may be splayed 180 degrees apart with a common axis of rotation. Thus, in some embodiments, the entire mandrel may form a T-shape. The entire mandrel may then be rotated about the axis of the leg portions and rotational spun fibers collected on the leg portions of the mandrel. The mandrel may then be oriented to rotate about the axis of the main lumen portion of the mandrel, and any unwanted fibers disposed while spinning on the bifurcated leg portions may be wiped off. The mandrel may then be rotated about the axis of the main lumen portion and fibers collected on the main lumen portion of the mandrel. The entire mandrel may then be placed in an oven and sintered. The mandrel portions associated with the bifurcated legs may then be removed from the leg or branch portions of the appliance, and the single lumen mandrel portion subsequently removed from the spun appliance. The appliance may then be placed on or within a frame structure, such as a stent frame. A dip or film coating (such as of FEP or PTFE) may then be applied over the construct to create an impervious outside layer and/or to further bond the frame to the spun portion of the appliance.

In any of the exemplary embodiments or methods disclosed herein, in instances where the nanofibers are formed of PTFE, the sintering temperature may be from about 360 degrees C. to about 400 degrees C., including at temperatures of about 385 degrees C. or at temperatures above the crystalline melting temperature of the PTFE, or about 342 degrees C. Similarly, for other materials, sintering may be done at or above the crystalline melting temperature of other spun polymers. Again, either prior to or as part of the sintering process, heat treating may be configured to remove PEO and/or water, in instances where the PTFE or other polymer was combined with such elements prior to spinning the mat.

In the embodiment of FIGS. 2A and 2B, the mandrels 216 may be disposed about the spinneret 210 in a generally circular configuration. In some embodiments, the mandrels 216 may be stationary while in other embodiments the mandrels 216 may be configured to rotate about their axes. In some such embodiments the mandrels 216 may each be driven by the same belt, allowing each to maintain the same rotational speed. In other embodiments some or all of the mandrels 216 may be independently driven.

In the illustrated embodiment, the mandrels 216 are disposed vertically, or such that the axis of each mandrel is substantially parallel to the axis of rotation of the spinneret. In another exemplary embodiment, one or more of the mandrels 216 may be disposed horizontally, or such that the axis of those mandrels is substantially orthogonal to the axis of rotation of the spinneret. In some embodiments, the axis of the mandrel 216 may be generally parallel to the axes of fibers being spun. Horizontally disposed mandrels 216 may be configured to produce mats having generally less fiber alignment than vertical mandrels. Horizontal mandrels may further be configured to produce mats with relatively uniform thickness around the mandrel.

In addition to horizontal mandrels, further embodiments may comprise mandrels disposed in any relative position with respect to the axis of the spinneret. Mandrels mounted in any disposition may be configured as stationary collection devices or configured to rotate. Additionally, combinations of mandrels in a variety of positions may be used simultaneously. Furthermore, in some embodiments one or more mandrels 216 may be configured for use in connection with a vacuum system. For example, openings in the surface of the mandrel, such a micro-porous mandrels 216, may tend to draw fibers toward the mandrel in instances where the interior of the mandrel 216 has lower pressure than the exterior of the mandrel 216.

In embodiments wherein the mandrels 216 rotate, the spinning motion of each mandrel 216 may tend to deposit the fibers around the entire surface of the mandrel. Thus, as the fibers are deposited on each mandrel 216, a seamless tube of nanofiber material may form on each mandrel 216. The density of the fibers, the thickness of the mat, and other characteristics may be controlled by such variables as the distance from the spinneret 210 to the mandrels 216, the rotational speed of the spinneret 210, the rotational speed of the mandrels 216, the orientation of the mandrels 216, the characteristics of the solution being spun, and so forth. In some instances, mats of rotational spun material formed on a spinning mandrel 216 may thus comprise a tubular membrane having no seam and substantially isotropic properties. In some instances the collection mandrel 216 may rotate at rates between about 1 RPM and about 2000 RPM during the rotational spinning process, including rates from about 1000 RPM to about 1500 RPM, including about 1500 RPM, or about 50 RPM to about 300 RPM, including about 150 RPM. In some instances, the rotational speed of one or more collection mandrels may be related to the rate at which the apparatus produces fibers. For example, in some embodiments, faster mandrel rotational speed may be correlated with higher total fiber production rates for the apparatus.

Furthermore, controlling the rotational speed of the mandrels 216 may influence both the density of the mat formed on the mandrels 216 and the general alignment of fibers in the mat. For instance, in some embodiments utilizing vertical mandrels, the faster the mandrel 216 is spinning the more the fibers may tend to be deposited in-line with other fibers. Further, the relative density of the fibers, for example, as measured by percent porosity, may be controlled in part by the rotational speed of the mandrels 216. FIGS. 13A-14B, discussed below, are SEMs of exemplary mats rotational spun onto rotating mandrels.

As further detailed in connection with FIGS. 4A-4E, once the fibers are rotational spun onto the mandrels 216 the fibers may be sintered. In some embodiments a scaffolding structure, such as a stent wire, may also be on the mandrel 216, and the nanofibers rotational spun directly onto the mandrel 216 and scaffolding structure.

FIGS. 3A and 3B illustrate an exemplary medical appliance: a stent 302. The stent 302 comprises a scaffolding structure 320 and a covering comprising an inner layer 325, an outer layer 330, and a tie layer 335. In other embodiments, a stent covering may have more or fewer layers than the illustrated embodiment, including embodiments with only one covering layer. Again, disclosure recited herein with respect to specific medical appliances, such as stents, may also be applicable to other medical appliances.

The cover of the stent 302 of FIG. 3A comprises a flat end 321 and a scalloped end 322. At the flat end 321 of the illustrated embodiment, the cover of the stent 302 is cut substantially perpendicular to the longitudinal axis of the stent 302. At the scalloped end 322, the cover of the stent 302 comprises cut away, or scalloped, portions at the end of the stent 302. Scalloped ends may be configured to reduce infolding of the stent cover at the ends. For example, in some instances, a stent may have a larger diameter than a vessel in which it is deployed. Thus, the vessel may partially compress the stent radially. In some instances this radial compression may create folds or wrinkles in flat cut stent covers. These folds may then impede blood flow or lead to clotting within the vessel. Scalloped ends may reduce the occurrence of infolding at the end of a radially compressed stent. It is within the scope of this disclosure to use either type of end on any end of any stent.

Membranes composed of rotational spun mats may have a microstructure composed of many fibers crossing each other at various and random points. The rotational spinning process may control the thickness of this structure and thereby, the relative permeability of the mat. As more and more fibers are rotational spun onto a mat, the mat may both increase in thickness and decrease in permeability (due to successive layers of strands occluding the pores and openings of layers below). Certain details of this microstructure are shown in FIGS. 11A-19, which are discussed in more detail below.

Mats produced in connection with the present disclosure may be described by three general parameters: percent porosity, mat thickness, and fiber diameter. Each of these parameters may impact the nature of the mat, including the tendency of the mat to permit tissue ingrowth and/or endothelial attachment or the tendency of the mat to resist tissue ingrowth or endothelial attachment. Each of these parameters may be optimized with respect to each other to create a mat having particular characteristics.

Percent porosity refers to the percent of open space to closed space (or space filled by fibers) in a fiber mat. Thus, the more open the mat is, the higher the percent porosity measurement. In some instances, percent porosity may be determined by first obtaining an image, such as an SEM, of a rotational spun material. The image may then be converted to a "binary image," or an image showing only black and white portions, for example. The binary image may then be analyzed and the percent porosity determined by comparing the relative numbers of each type of binary pixel. For example, an image may be converted to a black and white image wherein black portions represent gaps or holes in the rotational spun mat while white portions represent the fibers of the mat. Percent porosity may then be determined by dividing the number of black pixels by the number of total pixels in the image. In some instances, a code or script may be configured to make these analyses and calculations.

In some embodiments, percent porosities from about 30% to about 80% may be configured to permit tissue ingrowth into the layer and/or permit endothelial growth or attachment on the layer, including mats of about 40% to about 60%, mats of about 45% to about 50%, or mats of about 50% porosity. Less open layers may be configured to resist such ingrowth and/or attachment. Because the fibers comprising the mat are deposited in successive layers, the second parameter, mat thickness, may be related to porosity. In other words, the thicker the mat, the more layers of fibers, and the less porous the mat may be. In some embodiments, mats from about 20 micrometers to about 100 micrometers may be configured for use in connection with the present disclosure, including mats from about 40 micrometers to about 80 micrometers. Finally, the third parameter, fiber diameter, may be a measurement of the average fiber diameter of a sample in some instances. In some embodiments fiber diameters from about 50 nanometers to about 3 micrometers may be used in connection with the present disclosure. Notwithstanding these or other specific ranges included herein, it is within the scope of this disclosure to configure a mat with any combination of values for the given parameters.

In some embodiments the "average pore size" of the mat may be used as an alternate or additional measurement of the properties of the mat. The complex and random microstructure of rotational spun mats presents a challenge to the direct measurement of the average pore size of the mat. Average pore size can be indirectly determined by measuring the permeability of the mat to fluids using known testing techniques and instruments. Once the permeability is determined, that measurement may be used to determine an "effective" pore size of the rotational spun mat. As used herein, the "pore size" of a rotational spun mat refers to the pore size of a membrane which corresponds to the permeability of the rotational spun mat when measured using ASTM standard F316 for the permeability measurement. This standard is described in ASTM publication F316 "Standard Test Methods for Pore Size Characteristics of Membrane Filters by Bubble Point and Mean Flow Pore Test," which is incorporated herein by reference. In some instances this test can be used as a quality control after configuring a mat based on the three parameters (percent porosity, thickness, and fiber diameter) discussed above.

In some applications it may be desirable to create a medical appliance such as stent 302 with an outer layer 330 which is substantially impermeable. Such a layer may decrease the incidence of lumen tissue surrounding the stent growing into or attaching to the stent. This may be desirable in applications where the stent is used to treat stenosis or other occlusions; an impermeable outer layer may prevent tissue from growing into or through the material toward or into the lumen of the stent and reblocking or restricting the body lumen. In some embodiments a substantially impermeable outer layer may be produced by using rotational spun mats with a percent porosity from about 0% to about 50%, including about 25%; a thickness from about 20 micrometers to about 100 micrometers, including from about 40 micrometers to about 80 micrometers; and fiber diameters from about 50 nanometers to about 3 micrometers.

Additionally, or alternatively, a substantially impermeable mat may have an average pore size of about 0 microns to about 1.5 microns. In other embodiments, the impermeable layer may have an average pore size of less than about 0.5 micron. In yet other embodiments, the impermeable layer may have an average pore size of less than about 1 micron. In some embodiments, the impermeable layer may be a layer other than the outer layer, such as a tie layer, an intermediate layer, or an inner layer.

In one example, a medical appliance such as stent 302 may be covered with a rotational spun PTFE inner layer 325 and a rotational spun PTFE outer layer 330. The outer layer 330 may be configured to be substantially impermeable to tissue ingrowth and/or attachment. In other embodiments the impermeability of the stent may be provided by a tie layer 335 disposed between the outer layer 330 and the inner layer 325. For example, a substantially impermeable layer may be formed of FEP which is applied, for example, as a film or dip coating between rotational spun layers of PTFE. Furthermore, FEP may be rotational spun with a small average pore size to create a substantially impermeable layer. In some embodiments both the outer layer 330 and the tie layer 335 may be configured to be substantially impermeable.

Dip coatings may be applied by dipping a portion of a layer or construct in a polymer dispersion. For example, a PTFE layer may be dip coated on a construct by adding 20 ml of water to 50 ml of a 60 wt % PTFE dispersion to thin the dispersion. A fiber mat may then dipped in the solution to coat the mat. The dip coat may then sintered at 385 degrees C. for 15 minutes. Other concentrations of PTFE dispersions for dip coatings are also within the scope of this disclosure.

Further, an FEP layer may be dip coated on a construct by adding 20 ml of water to 50 ml of a 55 wt % dispersion to thin the dispersion. A fiber mat may then dipped in the solution to coat the mat. The dip coat may then cooked, for example, at 325 degrees C. for 15 minutes. Other concentrations of FEP dispersions for dip coatings are also within the scope of this disclosure. Additionally, polymer dispersions may be sprayed or otherwise applied onto a surface (such as a fiber mat) to coat the surface. Such coatings may be heat treated after application.

In some embodiments, more or less water, for example from about 10 ml to about 50 ml, may be added to similar amounts and concentrations of the dip dispersions above to thin the dispersions. Additionally, substances other than, or in addition to, water may be used to thin a dispersion for dip coating. For example, a surfactant or a solvent may be used. In some such cases the surfactant or solvent may later be removed from the construct, including embodiments where it is allowed to evaporate when the coat is sintered or cooked. Alcohols, glycols, ethers, and so forth may be so utilized.

In some embodiments it may be desirable to create a medical appliance such as stent 302 with an outer layer 330 which is more porous. A porous outer layer 330 may permit healing and the integration of the prosthesis into the body. For instance, tissue of the surrounding lumen may grow into the porous outer diameter or attach to the outer diameter layer. This tissue ingrowth may permit, modulate, and/or influence healing at the therapy site. In some embodiments a porous outer layer 330 may be formed of rotational spun PTFE.

In certain embodiments a relatively porous inner layer 325 may be desirable. This layer may or may not be used in conjunction with a substantially impermeable outer layer 330. A relatively porous inner layer may permit tissue ingrowth and/or endothelial attachment or growth on the inside diameter of the stent 302 which may be desirable for any combination of the following: healing, biocompatibility, prevention of thrombosis, and/or reducing turbulent blood flow within the stent. In some embodiments the inner layer may be comprised of a mat, such as a rotational spun PTFE mat, having a percent porosity of about 40% to about 80%, including about 50%; a thickness of about 20 micrometers to about 100 micrometers, including from about 40 micrometers to about 80 micrometers; and fiber diameters from about 50 nanometers to about 3 micrometers.

Additionally or alternatively the mat may be comprised of a rotational spun mat, such as PTFE, with an average pore size of about 1 micron to about 12 microns, such as from about 2 microns to about 8 microns, or from about 3 microns to about 5 microns, or alternatively from about 3.5 microns to about 4.5 microns.

FIG. 3B illustrates a cross sectional view of the stent 302 of FIG. 3A, again comprising a scaffolding structure 320 and covering comprising an inner layer 325, an outer layer 330, and a tie layer 335. Though in the illustration of FIG. 3B the tie layer 335 is shown at the same "level" as the scaffolding structure 320, the tie layer may be above or below the scaffolding in some embodiments. Further, as shown in FIG. 3B, each layer of the covering may be disposed so that there are no voids between layers.

In some embodiments the tie layer 335 may be configured to promote bonding between the outer layer 330 and the inner layer 325. In other embodiments the tie layer 335 may further be configured to provide certain properties to the stent 302 as a whole, such as stiffness or tensile strength. The tie layer 335 may thus be configured as a reinforcing layer. In some embodiments, expanded PTFE (ePTFE) may be configured as a reinforcing layer. ePTFE may be anisotropic, having differing properties in differing directions. For example, ePTFE may tend to resist creep in the direction the ePTFE membrane was expanded. A reinforcing layer of ePTFE may be oriented to increase strength, resist creep, or impart other properties in a particular direction. ePTFE may be oriented such that the expanded direction is aligned with an axial direction of a medical device, a transverse direction, a radial direction, at any angle to any of these directions, and so forth. Similarly, multiple layers of ePTFE may be disposed to increase strength, resist creep, or impart other properties in multiple directions. The reinforcing layer may or may not be impermeable.

Additionally, in embodiments where both the inner layer 325 and the outer layer 330 are porous in nature, the tie layer 335 may be configured to create an impermeable layer between the two porous layers. In such embodiments the stent may permit tissue ingrowth, tissue attachment and/or healing on both the inner and outer surfaces of the stent while still preventing tissue outside of the stent from growing into the lumen and occluding the lumen. Thus, tie layers may be configured to create a mid-layer portion of a construct, the tie-layer configured to inhibit tissue ingrowth into the layer or to be impervious to tissue migration into or through the layer or to substantially inhibit tissue migration.

Furthermore, the tie layer 335 may be configured to be impervious or substantially impervious to fluid migration across the tie layer 335. Specifically, constructions comprising one or more porous layers may allow fluid to cross the porous layer. In the case of a medical appliance configured to control blood flow, such as a graft, a porous layer may allow blood to leak across the layer or may allow certain smaller components of the blood to cross the layer while containing larger components, effectively filtering the blood. In some instances this filtration or ultrafiltration may allow components such as plasma to cross the barrier while containing red blood cells, leading to seroma. Thus, a fluid impermeable tie layer may be configured to contain fluid within a medical device also comprised of porous layers. In some devices, a tie layer may be both fluid impermeable and impervious to tissue ingrowth, or may be configured with either of these properties independent of the other. Constructs wherein any layer (other than, or in addition to a tie layer) is configured to be fluid impermeable and/or impervious to tissue ingrowth are also within the scope of this disclosure. Thus, disclosure recited herein in connection with fluid impermeable and/or tissue impervious tie layers may be analogously applied to impermeable layers at various locations within a construct.

The tie layer (or any impermeable/impervious layer) may include any thermoplastic and may or may not be rotational spun. In one embodiment, the tie layer may be expanded PTFE. In another it may be rotational spun PTFE. In other embodiments it may be FEP, including rotational spun FEP and FEP applied as a film or dip coating. Furthermore, the tie layer may include any of the following polymers or any other thermoplastic: dextran, alginates, chitosan, guar gum compounds, starch, polyvinylpyridine compounds, cellulosic compounds, cellulose ether, hydrolyzed polyacrylamides, polyacrylates, polycarboxylates, polyvinyl alcohol, polyethylene oxide, polyethylene glycol, polyethylene imine, polyvinylpyrrolidone, polyacrylic acid, poly(methacrylic acid), poly(itaconic acid), poly(2-hydroxyethyl acrylate), poly(2-(dimethylamino)ethyl methacrylate-co-acrylamide), poly(N-isopropylacrylamide), poly(2-acrylamido-2-methyl-1-propanesulfonic acid), poly (methoxyethylene), poly(vinyl alcohol), poly(vinyl alcohol) 12% acetyl, poly(2, 4-dimethyl-6-triazinylethylene), poly(3morpholinylethylene), poly(N-1,2,4-triazolyethylene), poly (vinyl sulfoxide), poly(vinyl amine), poly(N-vinyl pyrrolidone-co-vinyl acetate), poly(g-glutamic acid), poly(Npropanoyliminoethylene), poly(4-amino-sulfo-aniline), poly [N-(p-sulphophenyl)amino-3-hydroxymethyl-1,4phenyleneimino-1,4-phenylene], isopropyl cellulose, hydroxyethyl, hydroxylpropyl cellulose, cellulose acetate, cellulose nitrate, alginic ammonium salts, i-carrageenan, N-[(3'-hydroxy-2',3'-dicarboxy) ethyl]chitosan, konjac glocomannan, pullulan, xanthan gum, poly(allyammonium chloride), poly(allyammonium phosphate), poly(diallydimethylammonium chloride), poly(benzyltrimethylammonium chloride), poly(dimethyldodecyl(2-acrylamidoethyly) ammonium bromide), poly(4-N-butylpyridiniumethylene iodine), poly(2-N-methylpridinium methylene iodine), poly(N methylpryidinium-2,5-diylethenylene), polyethylene glycol polymers and copolymers, cellulose ethyl ether, cellulose ethyl hydroxyethyl ether, cellulose methyl hydroxyethyl ether, poly(l-glycerol methacrylate), poly(2-ethyl-2-oxazoline), poly(2-hydroxyethyl methacrylate/methacrylic acid) 90:10, poly(2-hydroxypropyl methacrylate), poly(2-methacryloxyethyltrimethylammonium bromide), poly(2-vinyl1-methylpyridinium bromide), poly(2-vinylpyridine N-oxide), poly(2-vinylpyridine), poly(3-chloro-2-hydroxypropyl 2-methacryloxyethyldimethylammonium chloride), poly (4vinylpyridine N-oxide), poly(4-vinylpyridine), poly (acrylamide/2-methacryloxyethyltrimethylammonium bromide) 80:20, poly(acrylamide/acrylic acid), poly(allylamine hydrochloride), poly(butadiene/maleic acid), poly(diallyldimethylammonium chloride), poly(ethyl acrylate/acrylic acid), poly(ethylene glycol) bis(2-aminoethyl), poly (ethylene glycol) monomethyl ether, poly(ethylene glycol)bisphenol A diglycidyl ether adduct, poly(ethylene oxide-bpropylene oxide), poly(ethylene/acrylic acid) 92:8, poly(llysine hydrobromide), poly(1-lysine hydrobromide), poly (maleic acid), poly(n-butyl acrylate/2methacryloxyethyltrimethylammonium bromide), poly(Niso-propylacrylamide), poly (N-vinylpyrrolidone/2dimethylaminoethyl methacrylate), dimethyl sulfatequaternary, poly(N-vinylpyrrolidone/vinyl acetate), poly(oxyethylene) sorbitan monolaurate (Tween 20®), poly (styrenesulfonic acid), poly(vinyl alcohol), N-methyl-4(4'formylstyryl)pyridinium, methosulfate acetal, poly(vinyl methyl ether), poly(vinylamine) hydrochloride, poly(vinylphosphonic acid), poly(vinylsulfonic acid) sodium salt, and polyaniline.

Regardless of the material, the tie layer 335 may or may not be rotational spun. Further, in certain embodiments the stent 302 may include two or more tie layers. The tie layer 335 may be formed in any manner known in the art and attached to the inner 325 and outer 330 layers in any manner known in the art. For example, the tie layer 335 may comprise a sheet of material which is wrapped around the inner layer 325 or a tube of material which is slipped over the inner layer 325 which is then heat shrunk or otherwise bonded to the inner 325 and outer 330 layers. Further, in embodiments where the tie layer is rotational spun, it may be rotational spun directly onto the inner layer 325, the scaffolding, or both. In some instances the tie layer 335 may be melted after the stent 302 is constructed to bond the tie layer 335 to adjacent layers of the stent covering.

Furthermore, tie layers may be configured to change the overall properties of the medical appliance. For example, in some instances a cover or construct comprised solely of rotational spun PTFE (of the desired pore size) may not have desired tensile or burst strength. A tie layer comprised of a relatively stronger material may be used to reinforce the PTFE inner layer, the PTFE outer layer, or both. For example, in some instances FEP layers may be used to increase the material strength of the cover. Again, as discussed above, the tie layer may also be configured as a portion of the construct configured to be impervious to tissue ingrowth or migration.

Further, one or more layers of rotational spun PTFE may be used in connection with a scaffolding structure other than that shown herein. In other words, the disclosure above relating to covers, layers, tie layers, and related components is applicable to any type of scaffolding structure as well as to stents or grafts with no separate scaffolding structure at all.

FIGS. 4A-4E illustrate certain steps in a process of manufacturing a multilayer construct for use in connection with a medical appliance. More specifically, these figures illustrate a process of creating a stent covered with rotational spun material. Again, this disclosure is equally relevant to all medical appliances which may comprise a cover or multi-layered construct, including grafts, patches, stents, and so on. Additionally, as suggested in the additional examples disclosed below, the illustrated steps may be optional in some instances or augmented by additional steps in others.

Figures 4A, 4B:
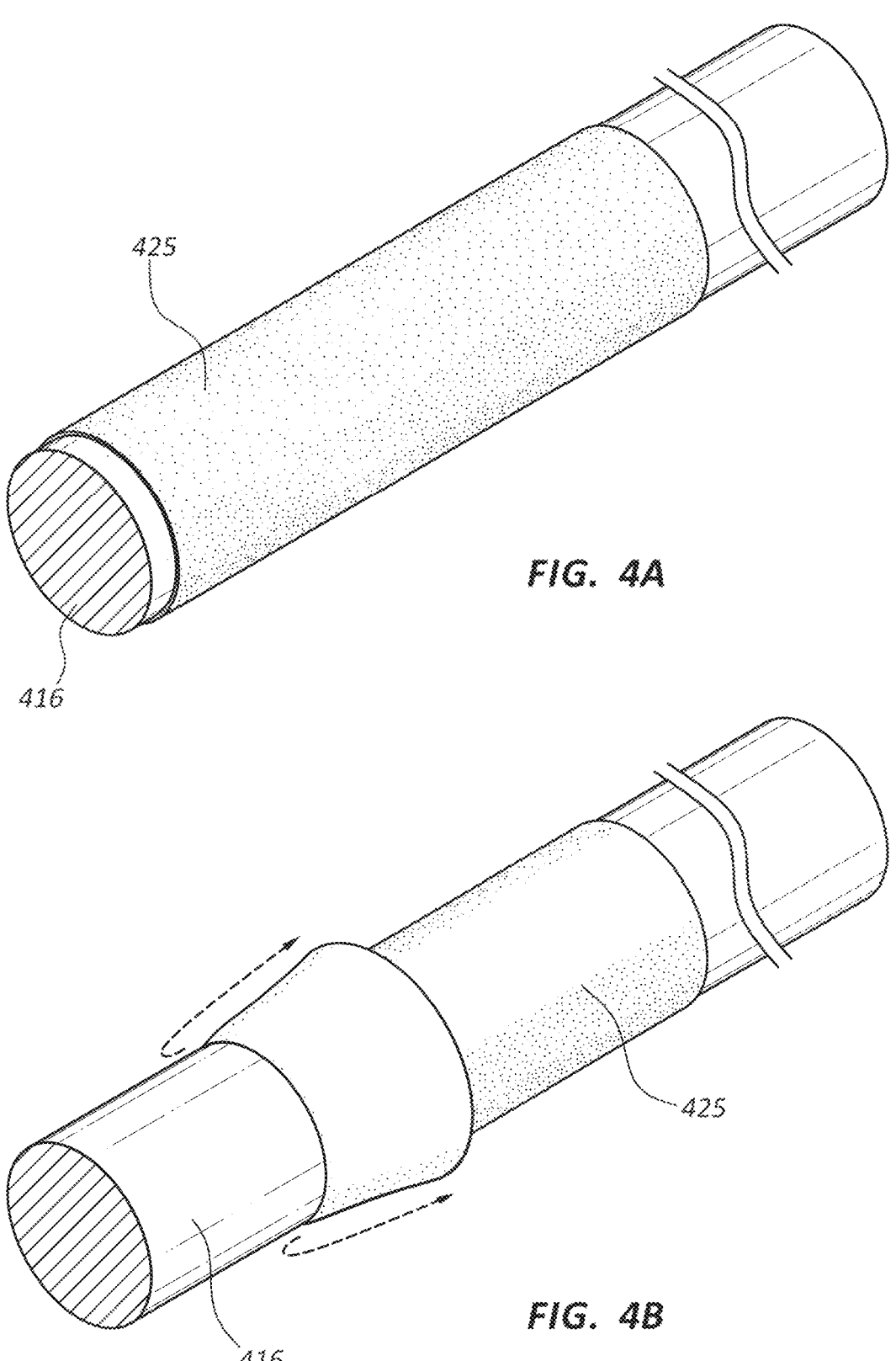
FIG. 4A is a perspective view of a rotational spun covering on a mandrel.
FIG. 4B is a perspective view of the covering of FIG. 4A partially removed from the mandrel.
Figure 5:
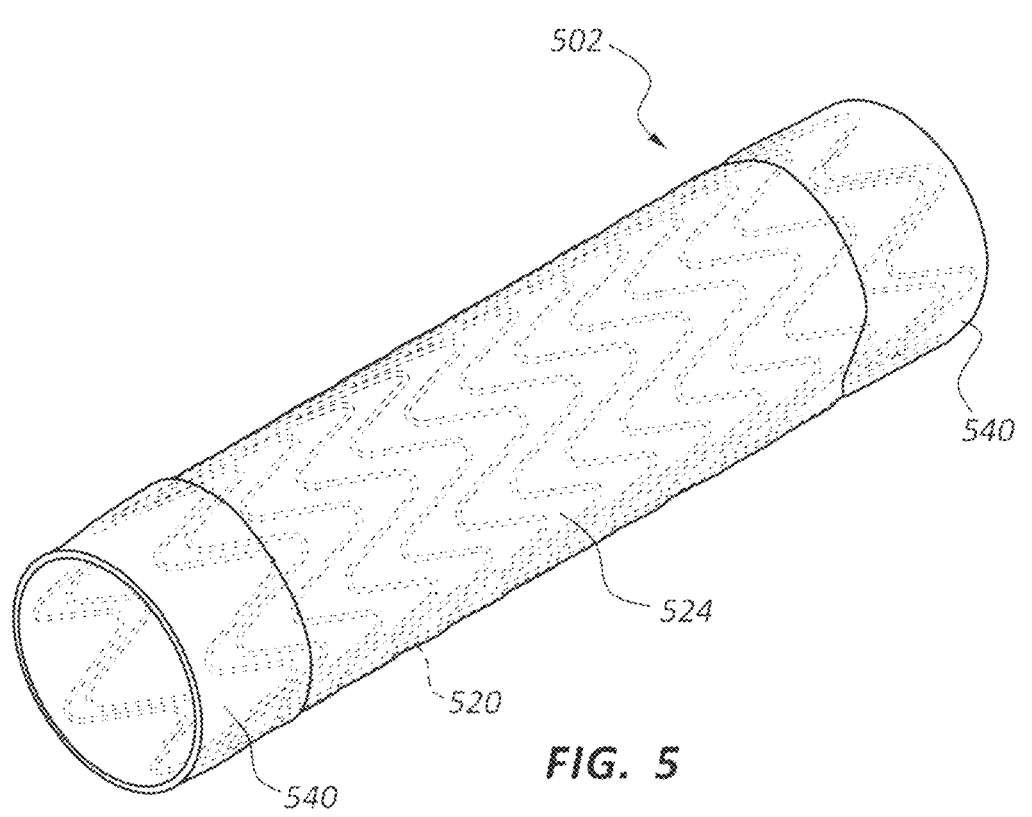
FIG. 5 is a perspective view of a covered stent including cuffs.

FIG. 4A illustrates a covering inner layer 425 disposed around a mandrel 416. As described above, the inner layer 425 may be rotational spun directly onto the mandrel 416, including instances wherein the mandrel 416 was rotating during the process. In the illustrated embodiment, the inner layer 425 was rotational spun onto a rotating mandrel 416 such that the resultant tube of material has no seam. After the inner layer 425 is rotational spun onto the mandrel 416, the inner layer 425 may then be sintered. In the case of PTFE, the membrane may be sintered at temperatures of about 385 degrees C., including temperatures from about 360 degrees C. to about 400 degrees C. Sintering may tend to set the structure of the PTFE, meaning sintering reduces the softness or flowability of the PTFE. Furthermore, as discussed above, sintering or otherwise heat treating the mat may evaporate any water or PEO mixed with the PTFE, resulting in a material comprised substantially of pure PTFE.

Once the inner layer 425 is sintered, the tube of material may be removed from the mandrel 416, as illustrated in FIG. 4B. As shown in the illustrated embodiment, the inner layer 425 may be "peeled" from the mandrel 416 to initially break any adherence of the inner layer 425 to the mandrel 416. The inner layer 425 may also be removed by pushing the covering with respect to the mandrel 416, causing the material to bunch as it is removed from the mandrel 416. In some embodiments, low friction coatings may alternatively or additionally be applied to the mandrel 416 before the inner layer 425 is rotational spun. The inner layer 425 may then be reapplied to the mandrel 416, by slipping the inner layer 425 over the mandrel 416, as illustrated in FIG. 4C.

Figures 4C, 4D:
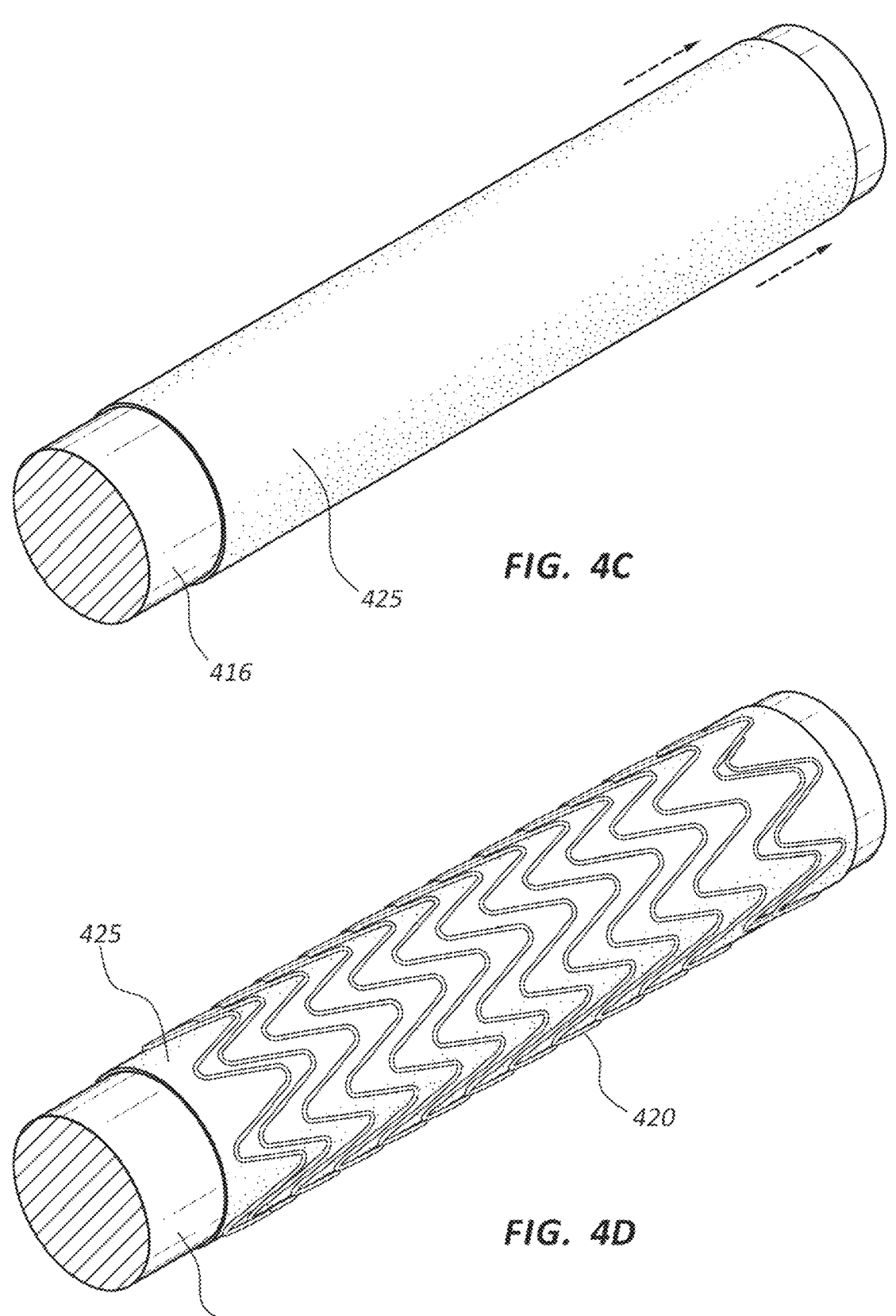
FIG. 4C is a perspective view of the covering of FIG. 4A repositioned on the mandrel.
FIG. 4D is a perspective view of a scaffolding structure wound around the covering and mandrel of FIG. 4C.
Figure 4E:
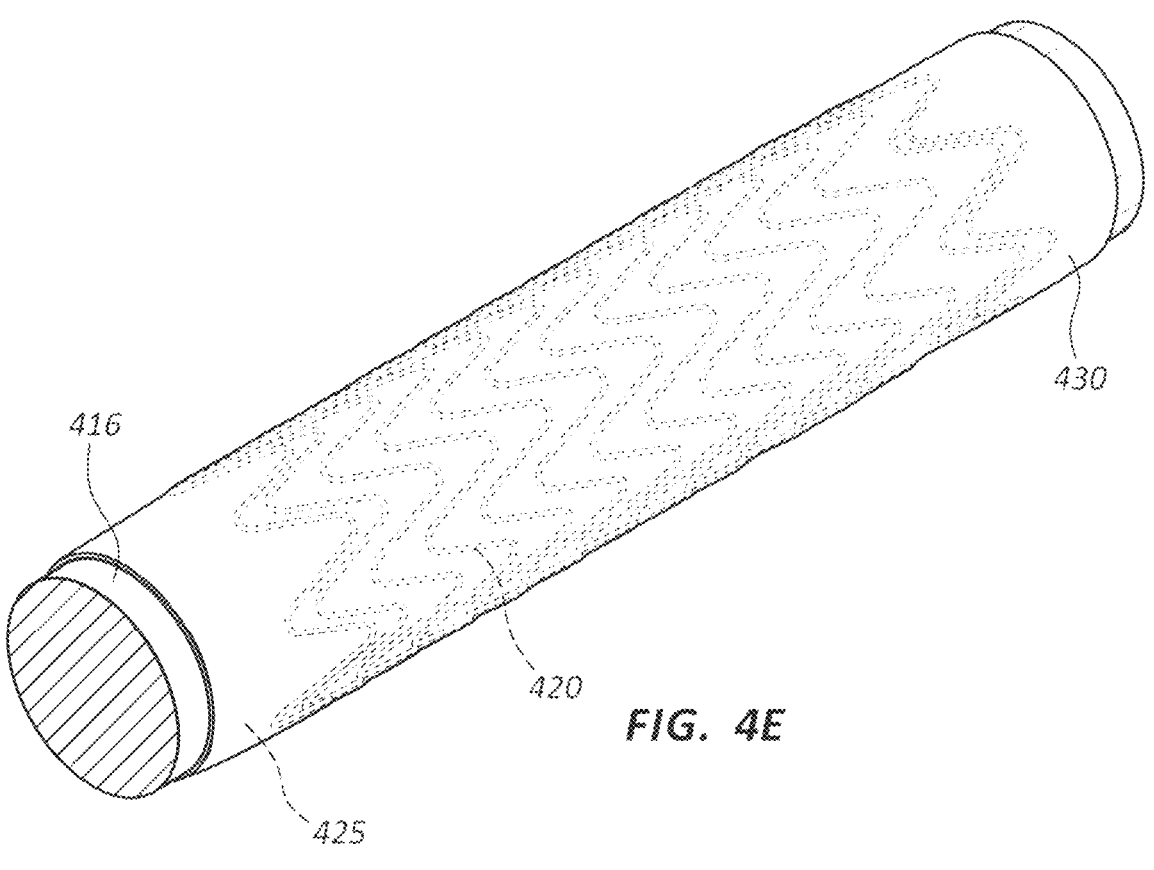
FIG. 4E is a perspective view of the scaffolding structure of FIG. 4D with a second rotational spun covering.

Once the inner layer 425 is reapplied to the mandrel 416, a wire scaffolding 420 can be formed over the mandrel 416 and the inner layer 425, as shown in FIG. 4D. FIG. 4E illustrates an outer layer 430 of material which may then be rotational spun onto the scaffolding 420 and the inner layer 425. The entire construct may then be sintered. Additional layers may also be added through similar processes.

Many variations to the above-described process are within the scope of the present disclosure. For example, one or more layers may be applied by wrapping strips or mats of material around the mandrel 416 and/or the other layers. Further, some of the layers may be applied by spray or dip coating the mandrel 416 and/or the other layers. It is within the scope of this disclosure to vary the process above to apply to any of the layers, or any additional layers, using any method disclosed herein.

In another example, a stent may be comprised of an inner layer of rotational spun PTFE, a tie layer of FEP, and an outer layer of PTFE. The properties of each of these layers, including percent porosity, mat thickness, fiber diameter, and/or average pore size may be controlled to form a covering layer that inhibits the growth of tissue into or through a particular layer or that permits endothelial growth or attachment on a particular layer.

In some such embodiments, the inner layer of PTFE may be spun on a mandrel, sintered, removed from the mandrel, and replaced on the mandrel then a scaffolding structure applied around the inner layer (analogous to the procedure illustrated in FIGS. 4A-4D). The FEP tie layer may then be applied by dipping, spraying, applying a film layer, electro-spinning, rotational spinning, extrusion, or other processing.

Figure 20:
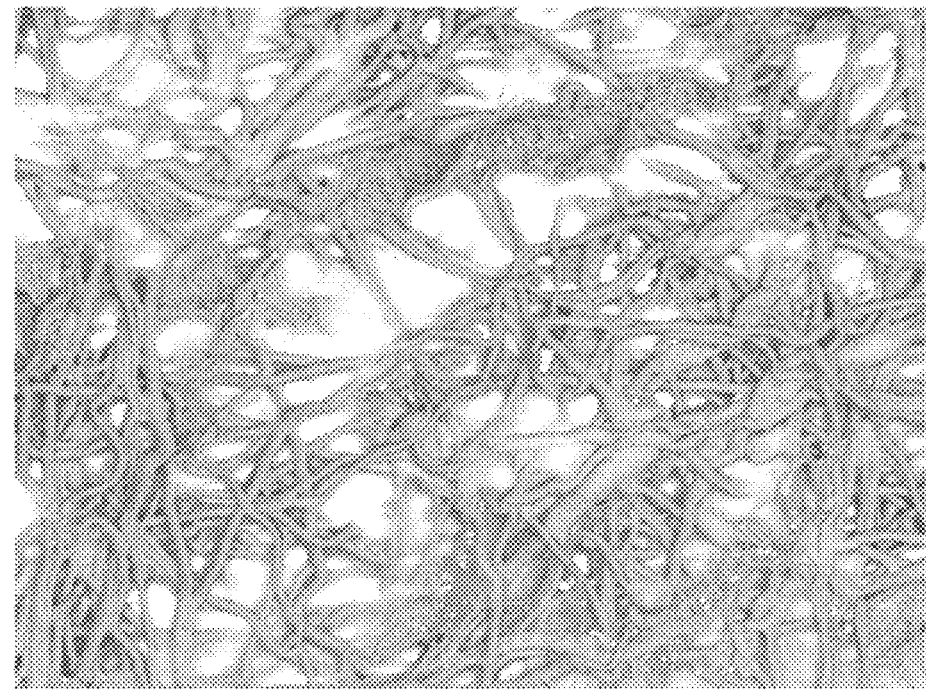
FIG. 20 is an SEM (at 950×) of a construct comprising a rotational spun PTFE material and an FEP layer.

In some embodiments, the FEP layer may be heated such that the FEP becomes soft, in some cases flowing into open spaces in adjacent PTFE layers. This may tie the FEP layer to adjacent PTFE layers. In some instances, heating the construct to about 325 degrees C. may allow the FEP to partially flow into openings in adjacent PTFE layers, without the FEP completely flowing through the PTFE mat. FIG. 20 and Example 10, included below, provide one example of an FEP layer partially melting into a rotational spun PTFE mat.

In another particular example, an inner layer of PTFE may be rotational spun on a mandrel, sintered, removed, and replaced, then a scaffolding structure applied around the inner layer. An FEP tie layer may then be applied as a film layer. In some instances this tie layer may be "tacked" into place, for example, by a soldering iron. A tube of PTFE (which may be formed separately by rotational spinning onto a mandrel and sintering) may then be disposed over the FEP film layer. The entire construct may then be pressured, for example, by applying a compression wrap. In some embodiments this wrap may comprise any suitable material, including a PTFE-based material. In other embodiments a Kapton film may be wrapped around the construct before the compression wrap, to prevent the construct from adhering to the compression wrap.

The compressed layers may then be heated above the melting temperature of the FEP tie layer, but below the sintering temperature of the PTFE. For example, the melt temperature of the FEP may be from about 264 degrees C. to about 380 degrees C., including about 325 degrees C. PTFE may be sintered at temperatures from about 360 degrees C. to about 400 degrees C. Thus, the entire construct may be heated to an appropriate temperature such as about 325 degrees C. In some embodiments the construct may be held at this temperature for about 15 to about 20 minutes. Heating the FEP layer to about 325 degrees C. may allow the FEP layer to remain substantially impervious to tissue ingrowth and/or attachment, creating a "barrier" layer within the construct, while still adhering the FEP to adjacent layers of PTFE. In other embodiments, heating the construct to higher temperatures, such as about 350 degrees C. or more may be configured to allow the FEP to flow around the PTFE such that the entire construct has a higher degree of porosity and the FEP layer is not as impervious to ingrowth.

The joining of the FEP tie layer to the PTFE outer and inner cover layers may increase the strength of the finished covering. The construct may then be cooled and the compression wrap and the Kapton film discarded. The construct may then be removed from the mandrel.

A stent formed by the exemplary process described above may be configured with desired characteristics of porosity and strength. In some instances the FEP material may coat the PTFE nanofibers but still allow for sufficient porosity to permit tissue ingrowth and/or endothelial attachment or growth. The degree to which the FEP coats the PTFE may be controlled by the temperature and time of processing. The lower the temperature and/or the shorter the time the construct is held at temperature, the less the FEP may flow. In some instances a tie layer of FEP which is impervious to tissue ingrowth into or through the layer may be formed by heating the construction only to about 270 degrees C.

FIG. 5 illustrates a stent 502 which comprises a scaffolding structure 520 and a covering 524. The covering 524 may be comprised of any combination of layers disclosed herein. Additionally, the stent 502 of FIG. 5 includes a cuff 540 at both ends of the stent 502. In other embodiments a cuff 540 may only be located at one end of the stent 502.

The cuff 540 may comprise an additional covering layer on the outside diameter of the stent 502, disposed adjacent to one or both ends of the stent 502. The cuff 540 may be configured to promote tissue ingrowth, attachment, and/or incorporation into the cuff 540; for example the cuff 540 may be more porous than an outer layer of the covering 524 of the stent 502. Factors such as porosity, type of covering or coating, type of material, use of organic material, and/or use or composite materials formed of synthetic material and organic material may be used to create a cuff 540 configured for tissue ingrowth. Again, the cuff 540 may be configured to promote tissue ingrowth and/or the growth or attachment of endothelial cells at one or both ends of the stent 502. When implanted in the body, the cuffs 540 may tend to "anchor" the ends of the stent 502 with respect to the vessel walls, reducing the relative movement of the stent ends with respect to the vessel walls. Such a reduction in movement may lessen irritation of the vessel by the stent ends, minimizing complications such as stenosis. Cuffs 540 may be configured for use in CVO type applications in some instances. Furthermore, a band of porous material analogous to the stent cuff 540 illustrated may be coupled to any medical appliance to anchor a portion of such a device.

In some embodiments, the outer layer of the covering 524 of the stent 502 may be relatively non-porous to inhibit tissue ingrowth into or through the outer layer, but the cuff 540, disposed about the outer layer, may provide a section near each end at which some tissue ingrowth, attachment, or incorporation may occur.

The cuff 540 may be comprised of a rotational spun material, such as PTFE, and may be bonded to the outer covering layer through any method, including methods of multilayer device construction described herein. For example, a layer of FEP may be disposed between the outer covering layer and the cuff 540 and heated to bond the layers. In other embodiments the cuff 540 may comprise a collagen layer which is coupled to the stent. Further, a co-rotational spun collagen and PTFE cuff 540 may be utilized.

The current disclosure relates to medical appliances, including stents, which may comprise a frame structure provided in connection with one or more coverings or coatings. It will be appreciated that, though particular structures, coverings, and coatings are described herein, any feature of the frames or coverings and/or coatings described herein may be combined with any other disclosed feature without departing from the scope of the current disclosure. For example, certain figures reference below show a metal frame without any covering or coating; the features described and illustrated in those figures may be combined with any combination of coverings or coatings disclosed herein. Further, as used herein, the term "frame" refers to a support structure for use in connection with a medical appliance. For instance, a scaffolding structure, such as that described in connection with FIGS. 4A-4E, above, is an example of a frame used in connection with a medical appliance. In some embodiments, a medical appliance—such as a stent—may comprise frame alone, with no covering, coating, or other components.

Moreover, the current disclosure is applicable to a wide variety of medical appliances which may utilize any of the rotational spun mats disclosed herein, including medical appliances which comprise multilayered constructs. For example, a hernia patch may comprise a two layered construction, which one side of the patch configured to allow tissue ingrowth and/or attachment (for bonding and healing) and the other side configured to resist such ingrowth and/or attachment (to make the second side "slippery" with respect to surrounding tissue. Further, a patch as described above may also comprise a tie layer disposed between the two exterior layers. The tie layer may be configured resist tissue ingrowth or attachment into or through the patch and/or to provide mechanical properties such as strength to the construct.

Figures 6, 7A, 7B, 7C:
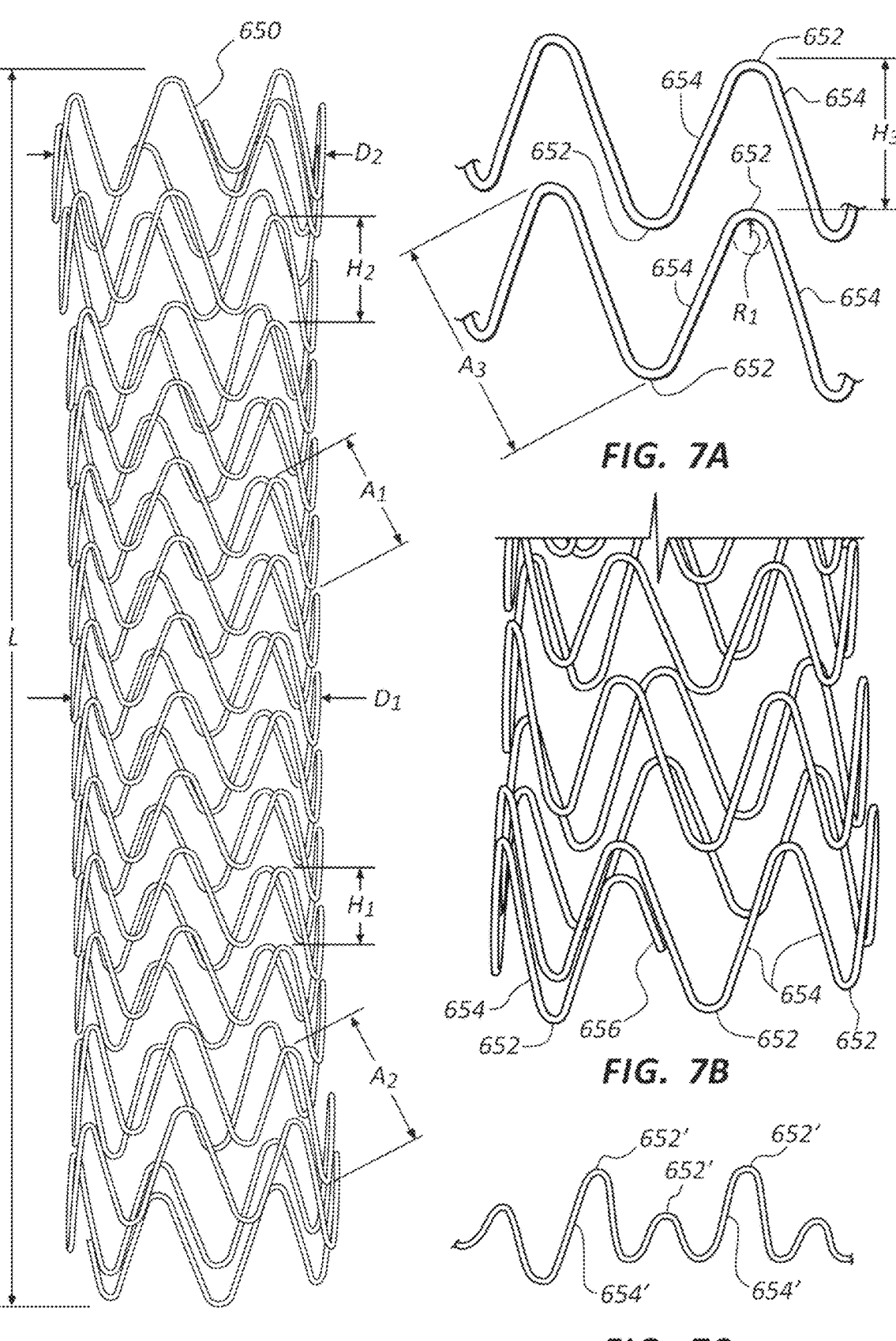
FIG. 6 is a front view of a medical appliance frame structure.
FIG. 7A is a detail view of a portion of the frame of FIG. 6.
FIG. 7B is a detail view of an end of the frame of FIG. 6.
FIG. 7C is an alternate configuration of a portion of the frame of FIG. 6.
Figure 8:
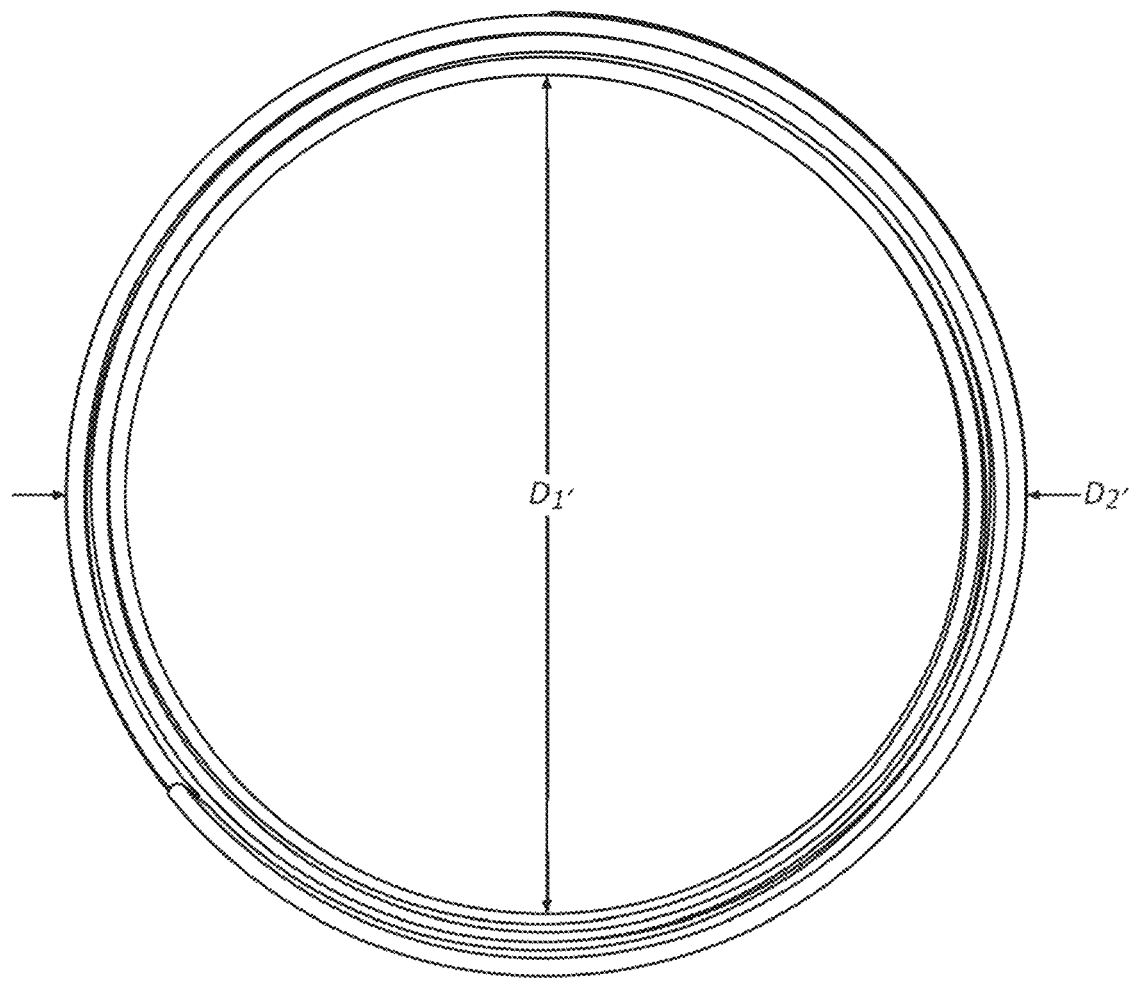
FIG. 8 is an end view of a frame having flared ends.
Figure 9:
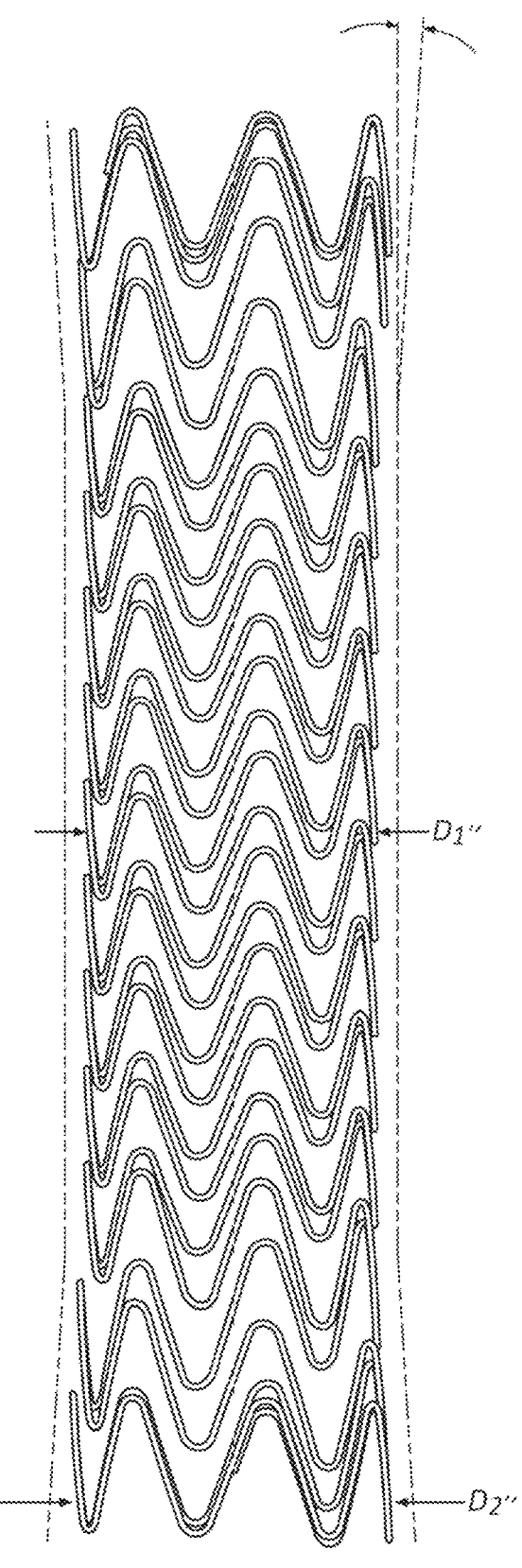
FIG. 9 is front view of a frame having flared ends.
Figure 10:
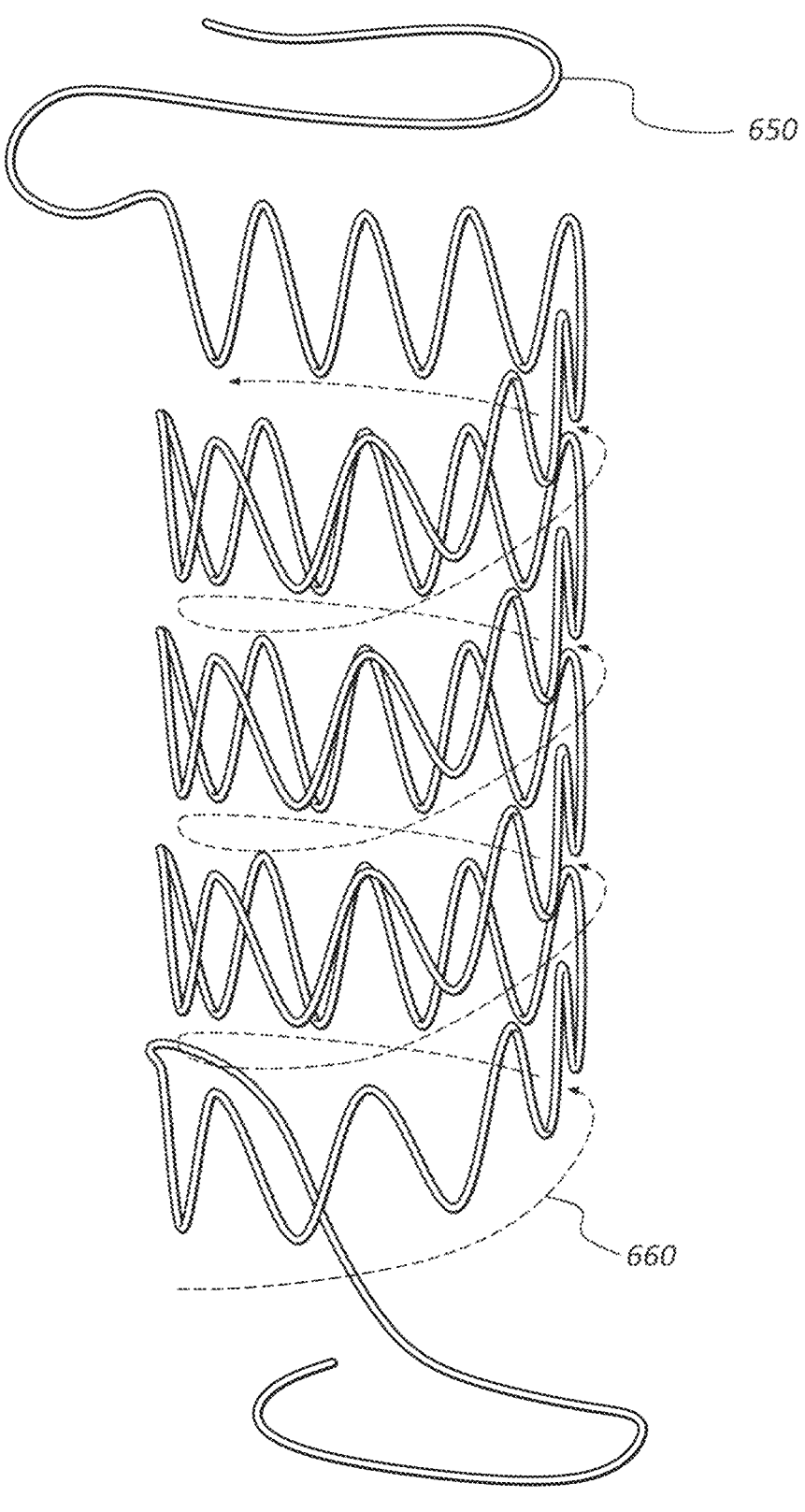
FIG. 10 is a front view of a wire being shaped to form a frame.

FIGS. 6, 7A, and 7B show views of a possible embodiment of a frame for use in connection with a medical appliance such as a stent or graft. FIG. 7C is an alternative configuration of a portion of the frame structure. FIGS. 8 and 9 are views of one embodiment of a frame which includes flared ends. FIG. 10 illustrates one embodiment of how a wire may be shaped to form a frame.

Frames for use in connection with medical appliances may be fabricated or formed into particular geometries through a variety of means. For example, a frame may be cut from a single tube of material, including embodiments wherein the frame is first laser cut, then expanded. In other embodiments, the frame may be molded, including embodiments wherein the frame is molded from a polymeric material. In still other embodiments, powder metallurgical processes, such as powdered compression molding or direct metal laser sintering, may be used.

FIG. 6 illustrates a front elevation view of an embodiment of a frame. The illustrated embodiment depicts one embodiment of a configuration for a metal wire 650 forming a frame. As depicted in FIG. 6, the frame may consist of a single continuous wire.

Referring generally to FIGS. 6, 7A, and 7B, particular features of the illustrated frame structure are indicated. It will be appreciated that the numerals and designations used in any figure apply to analogous features in other illustrated embodiments, whether or not the feature is so identified in each figure. As generally shown in these Figures, the frame structure may consist of a wire 650 shaped to form the frame. The wire 650 may be shaped in a wave-type configuration, the waves defining apexes 652 and arms 654 of the frame structure. The frame may further be coupled to a covering layer (not pictured). Additionally, in some embodiments, any covering as disclosed herein may be applied to any type of frame, for example, laser cut frames, polymeric frames, wire frames, and so forth.

The frame may be designed such that the midsection is "harder" than the ends. The "hardness" of the frame refers to the relative strength of the structure (e.g., its compressibility). A harder portion of the frame will have greater strength (i.e., exert a greater radial outward force) than a softer portion. In one embodiment, the midsection is harder than the proximal and distal end sections which are relatively softer. Further, a frame may be configured to be flexible to facilitate the ability of the device to conform to the native anatomy at which the device is configured for use. Similarly, covered devices may be configured with covers which conform to the native anatomy at a therapy site.

Additionally, the frame may be configured to allow the entire device to be crimped into a relatively low-profile configuration for delivery. For example, devices of a certain diameter or constrained profile are more feasible for delivery at certain vascular or other access points than others. For example, in many instances a device configured for insertion via the radial artery may be relatively smaller than devices configured for insertion via the generally larger femoral artery. A frame may be configured to be crimped into a particular profile to enable potential access at various or desired access points. Similarly, devices having no frame may be configured to be disposed in a particular profile to facilitate access and delivery. Once a device is positioned within the body it may be expanded or deployed in a number of ways, including use of self expanding materials and configurations. Additionally, some configurations may be designed for expansion by a secondary device, such as a balloon.

Four basic design parameters may be manipulated to influence the properties (hardness, strength, crush force, hoop force, flexibility, etc.) of the illustrated frame. These properties are: (1) apex to apex distance, designated as $H_x$ in FIGS. 6 and 7A; (2) arm length, designated as $A_x$ in FIGS. 6 and 7A; (3) apex radius, designated as $R_x$ in FIG. 7A; and (4) the diameter of the wire 650. These values may or may not be constant at different points on a frame. Thus, the subscript "x" is used generically; that is, each distance identified as "H" refers to an apex to apex distance with subscripts 1, 2, 3, etc., signifying the apex to apex distance at a particular point. It will be appreciated that these subscript designations do not necessarily refer to a specific distance, but may be used relatively (i.e., $H_1$ may be designated as smaller than $H_2$ without assigning any precise value to either measurement). Further, as will be apparent to one skilled in the art having the benefit of this disclosure, an analogous pattern of measurements and subscripts is employed for other parameters described herein, for example $A_x$ and $R_x$.

The overall frame design may be configured to optimize desired radial force, crush profile, and strain profile. The frame design parameters may each be configured and tuned to create desired characteristics. For example, the strain profile may be configured to be less than the failure point for the material being used.

A first parameter, the apex to apex distance, is designated as $H_x$. This measurement signifies the distance between a first apex and a second apex where both apexes substantially lie along a line on the outside diameter of the frame which is co-planar with, and parallel to, the longitudinal axis of the frame. In some embodiments, $H_x$ may be constant along the entire length of the frame. In other embodiments the length of the frame may be divided into one or more "zones" where $H_x$ is constant within a zone, but each zone may have a different $H_x$. In still other embodiments $H_x$ may vary along the entire length of the frame. $H_x$ may be configured, in connection with the other design parameters, to determine the properties of the frame. Generally, regions of the frame with a smaller $H_x$ value will be harder than regions with a larger $H_x$ value.

In the embodiment illustrated in FIG. 6, there are two "flare zones" at either end of the frame and a midbody zone along the remaining length of the frame. In the illustrated embodiment, $H_1$ designates the apex to apex distance in the midbody zone of the frame and $H_2$ designates the apex to apex distance in the flare zones of the frame. In the illustrated embodiment, the apex to apex distance, $H_2$, is the same in both the flare zone near the distal end of the frame and the flare zone near the proximal end of the frame. In some embodiments $H_1$ may be smaller than $H_2$, resulting in a frame that is relatively harder in the midbody and relatively softer on the ends. A frame with such properties may be utilized in applications where strength is necessary along the midbody, for example to treat a tumor or other occlusion, but the ends are configured to rest on healthy tissue where softer ends will minimize trauma to the healthy tissue.

In embodiments where soft ends and a hard midbody are desirable, $H_1$ may be between about 2 mm and 30 mm, and $H_2$ between about 2.1 mm and 30.1 mm. For example, in frames configured for use in connection with stents for CV or PV application, $H_1$ may be between about 3 mm and 10 mm, and $H_2$ between about 3.1 mm and 10.1 mm, such as: $3 \text{ mm} < H_1 < 8 \text{ mm}$ and $3.5 \text{ mm} < H_2 < 9 \text{ mm}$; $3 \text{ mm} < H_1 < 6.5 \text{ mm}$ and $4 \text{ mm} < H_2 < 8 \text{ mm}$; or $3 \text{ mm} < H_1 < 5 \text{ mm}$ and $5.5 \text{ mm} < H_2 < 6.5 \text{ mm}$.

In other embodiments where two or more apex to apex lengths are present in one frame, the change in apex to apex length may be correlated to the displacement of the apexes from the midpoint of the frame. In other words, the apex to apex length may increase incrementally as one moves away from the midpoint of the frame toward the ends in a manner that gives the frame the same geometry, and therefore the same properties, on either side of the midpoint of the length of the frame. In other embodiments, different geometries may be utilized at any point along the length of the frame. It will be appreciated that the ranges of values for $H_x$ disclosed above apply analogously to embodiments where the frame has multiple apex to apex lengths. For example, in one embodiment a frame may have an apex to apex length at midbody within one of the ranges disclosed above for $H_1$, and the value of $H_x$ may vary incrementally, in steps, or some other pattern, along the length of the frame reaching an apex to apex length at the ends within the complementary range for $H_2$.

Moreover, in some embodiments, the value of $H_x$ may be small enough that adjacent coils are "nested" within each other. In other words, the apexes of a first helical coil may extend up into the spaces just below the apexes of the next adjacent coil. In other words, apexes of lower coils may extend a sufficient amount so as to be disposed between the arms of higher coils. In other embodiments the value of $H_x$ may be large enough that adjacent coils are completely separated. In embodiments wherein adjacent coils are "nested," the number of wires at any particular cross section of the stent may be higher than a non-nested stent. In other words, cutting the frame along an imaginary plane disposed orthogonally to the longitudinal axis of the frame will intersect more wires if the frame is nested as compared to not nested. The smaller the value of $H_x$, the more the rows may be intersected by such a plane (that is, more than just the next adjacent row may extend into the spaces below the apexes of a particular row). Nested frames may create relatively higher strains in the frame when a stent comprised of the frame is loaded into a delivery catheter. In some instances the delivery catheter for a nested frame may therefore be relatively larger than a delivery catheter configured for a non-nested frame. Further, nested frames may be relatively stiff as compared to non-nested stents with similar parameters.

As will be apparent to those skilled in the art having the benefit of this disclosure, frames with a hard midbody and soft ends may be desirable for a variety of applications. Further, in some instances a basically "symmetric" frame may be desirable; in other words, a frame with certain properties at the midbody section and other properties at the ends, where the properties at both ends are substantially identical. Of course, other embodiments may have varied properties along the entire length of the frame. It will be appreciated that while the effect of changing variables, for instance the difference between $H_1$ and $H_2$, may be described in connection with a substantially symmetric stent (as in FIG. 6) the same principles may be utilized to control the properties of a frame where the geometry varies along the entire length of the frame. As will be appreciated by those skilled in the art having the benefit of this disclosure, this applies to each of the variable parameters described herein, for example $H_x$, $A_x$, and $R_x$.

A second parameter, arm length, is designated as $A_x$ in FIGS. 6 and 7A. As with $H_x$, $A_x$ may be constant along the length of the frame, be constant within zones, or vary along the length of the frame. Variations in the length of $A_x$ may be configured in conjunction with variations in the other parameters to create a frame with a particular set of properties. Generally, regions of the frame where $A_x$ is relatively shorter will be harder than regions where $A_x$ is longer.

In some embodiments, the arm length $A_1$ near the midsection of the frame will be shorter than the arm length $A_2$ near the ends. This configuration may result in the frame being relatively harder in the midsection. In embodiments where soft ends and a hard midbody are desirable, $A_1$ may be between about 2 mm and 30 mm, and $A_2$ between about 2.1 mm and 30.1 mm. For example, in frames for CV or PV application, $A_1$ may be between about 2 mm and 10 mm, and $A_2$ between about 2.1 mm and 10.1 mm, such as: 2.5 mm$<A_1<$8 mm and 3 mm$<A_2<$9 mm; 3 mm$<A_1<$6 mm and 4 mm$<A_2<$7.5 mm; or 4 mm$<A_1<$5 mm and 5 mm$<A_2<$6 mm.

In other embodiments where two or more arm lengths are present in one frame, the change in arm length may be correlated to the displacement of the arm from the midpoint along the frame. In other words, the arm length may increase incrementally as one moves away from the midpoint of the frame toward the ends in a manner that gives the frame the same geometry, and therefore the same properties, on either side of the midpoint of the length of the frame. In other embodiments, different geometries may be utilized at any point along the length of the frame. It will be appreciated that the ranges of values for $A_x$ disclosed above apply analogously to embodiments where the frame has multiple arm lengths. For example, in one embodiment a frame may have an arm length at midbody within one of the ranges disclosed above for $A_1$, and the value of $A_x$ may vary incrementally, in steps, or some other pattern, along the length of the frame reaching an arm length at the ends within the complementary range for $A_2$.

A third parameter, the apex radius, is designated as $R_1$ in FIG. 7A. As with $H_x$, and $A_x$, $R_x$ may be configured in order to create desired properties in a frame. In some embodiments, the inside radius of each apex may form an arc which has a substantially constant radius. As shown by a dashed line in FIG. 7A, this arc can be extended to form a circle within the apex. The measurement $R_x$ refers to the radius of the arc and circle so described. Further, in some embodiments the arms and apexes of the frame are formed by molding a wire around pins protruding from a mandrel. The radius of the pin used gives the apex its shape and therefore has substantially the same radius as the apex. In some embodiments $R_x$ will be constant along the entire length of the frame, be constant within zones along the length of the frame, or vary along the entire length of the frame. Variations in the magnitude of $R_x$ may be configured in conjunction with variations in the other parameters to create a frame with a particular set of properties. Generally, regions of the frame where $R_x$ is relatively smaller will be harder than regions where $R_x$ is larger.

Furthermore, in some instances, smaller values of $R_x$ may result in relatively lower strain in the wire frame when the frame is compressed, for example when the frame is disposed within a delivery catheter. Moreover, wires of relatively larger diameters may result in relatively lower strain at or adjacent to the radius measured by $R_x$ when compressed, as compared to wires of smaller diameters. Thus, in some instances, the strain may be optimized for a particular design by varying the value of $R_x$ and the diameter of the wire forming the frame.

Like the other variables, $R_x$ may take on a range of values depending on the application and the desired properties of the frame. In some embodiments $R_x$ may be between about 0.12 mm and 1.5 mm, including from about 0.12 to about 0.64 mm. For example, in frames configured for use with stents for CV or PV application, $R_x$ may be between about 0.35 mm and 0.70 mm, such as: 0.35 mm$<R_x<$0.65 mm; 0.35 mm$<R_x<$0.6 mm; or 0.4 mm$<R_x<$0.5 mm.

It will be appreciated that the disclosed ranges for $R_x$ apply whether the value of $R_x$ is constant along the length of the frame, whether the frame is divided into zones with different $R_x$ values, or whether $R_x$ varies along the entire length of the frame.

The fourth parameter, wire diameter, is discussed in detail in connection with FIG. 10 below.

FIG. 7A illustrates a cutaway view of the front portions of two adjacent coils of a frame. The portions of the coils depicted are meant to be illustrative, providing a clear view of the three parameters $H_x$, $A_x$, and $R_x$. It will be appreciated that all three of these parameters may be configured in order to create a frame with particular properties. Any combination of the values, ranges, or relative magnitudes of these parameters disclosed herein may be used within the scope of this disclosure. As an example of these values taken together, in one embodiment of a CV or PV frame with a relatively hard midbody and softer ends, $H_1$ may be about 4 mm and $H_2$ about 5.9 mm; $A_1$ may be about 4.5 mm and $A_2$ about 5.6 mm; and $R_1$ about 0.5 mm.

FIG. 7B is a close up view of one end of a frame. In embodiments where the frame is formed by a single continuous wire, FIG. 7B illustrates one way in which the end 656 of the wire may be coupled to the frame. As illustrated, the wire may be disposed such that the final coil approaches and runs substantially parallel to the previous coil. This configuration results in the apex to apex distance between the two coils decreasing near the end 656 of the wire. In some embodiments this transition will occur along the distance of about 4 to 8 apexes along the length of the wire. For example, if a frame is configured with an apex to apex spacing of $H_2'$ along the region of the frame nearest to the ends, the apex to apex distance will decrease from $H_2'$ to a smaller distance which allows the end 656 of the wire to meet the prior coil (as illustrated in FIG. 7B) over the course of about 4 to 8 apexes.

FIG. 7C illustrates an alternative configuration of a portion of a frame. In the embodiment of FIG. 7C, apexes 652' alternate in relative height along the length of the wire. In particular, in the embodiment shown, the apexes form a pattern comprising a higher apex, a shorter apex, a higher apex, a shorter apex, and so on, around the helical coil. In some instances, a frame may be configured with alternating apexes at one or both ends of the frame. For example, a frame as shown in FIG. 6 may be configured with the pattern of apexes 652' and arms 654' shown in FIG. 7C at one or both ends of the frame. Such an alternating pattern of apexes may distribute the force along the vessel wall at the ends of the frame, thus creating relatively a-traumatic ends.

The end 656 may be attached to the frame in a variety of ways known in the art. The end 656 may be laser welded to the frame or mechanically crimped to the frame. In embodiments where the frame is an element of a medical appliance further comprising a polymer cover, the end 656 may be secured by simply being bound to the cover. In other instances, a string may be used to bind or tie the end 656 to adjacent portions of the frame. Similarly, in some instances, a radiopaque marker may be crimped around the end 656 in such a manner as to couple the end 656 to the frame. Additionally other methods known in the art may be utilized.

Furthermore, in some embodiments the frame may be configured with radiopaque markers at one or more points along the frame. Such markers may be crimped to the frame. In other embodiments a radiopaque ribbon, for example a gold ribbon, may be threaded or applied to the frame. In some embodiments these markers may be located at or adjacent to one or both ends of the frame. Any radiopaque material may be used, for example gold or tantalum. Radiopaque elements may be configured to facilitate the delivery and placement of a device and/or to facilitate viewing of the device under fluoroscopy.

Referring again to FIG. 6 as well as to FIGS. 8 and 9, the frame may be configured with flared ends. It will be appreciated that in certain embodiments a frame may have a flare at both the proximal and distal ends, only at the proximal end or only at the distal end, or at neither end. In certain of these embodiments the frame may have a substantially constant diameter in the midbody zone of the frame, with the ends flaring outward to a larger diameter. It will be appreciated that the geometry of the flares at the proximal and distal ends may or may not be the same.

In the embodiment illustrated in FIG. 6, the frame has a diameter, $D_1$, at the midbody of the frame. This diameter may be constant along the entire midbody of the frame. The illustrated embodiment has a second diameter, $D_2$, at the ends. This change in diameter creates a "flare zone" at the end of the frame, or an area in which the diameter is increasing and the frame therefore may be described as including a "flared" portion. In some embodiments the flare zone will be from about 1 mm to 60 mm in length. For example in certain frames configured for use with stents designed for CV or PV application, the flare zone may be from about 3 mm to about 25 mm in length, such as: from about 4 mm to about 15 mm, or from about 5 mm to about 10 mm in length.

The diameter of the stent at the midbody, the diameter at one or both flares, or all of these dimensions, may be configured to be slightly larger than the body lumen for in which the device is configured for use. Thus, the size of the device may cause interference with the lumen and reduce the likelihood the device will migrate within the lumen. Further, active anti-migration or fixation elements such as barbs or anchors may also be used.

FIGS. 8 and 9 also illustrate how a frame may be flared at the ends. Diameters $D_1{}'$ and $D_1{}''$ refer to midbody diameters, analogous to $D_1$, while $D_2{}'$ and $D_2{}''$ refer to end diameters analogous to $D_2$. Further, as illustrated in FIG. 9, the flared end may create an angle, alpha, between the surface of the frame at the midbody and the surface of the flare. In some instances the flare section will uniformly flare out at a constant angle, as illustrated in FIG. 9. In some embodiments angle alpha will be from about 1 degree to about 30 degrees. For example, in some frames configured for use with stents designed for CV or PV application, alpha will be from about 2 degrees to 8 degrees, such as: from about 2.5 degrees to about 7 degrees or from about 3 degrees to about 5 degrees. In one exemplary embodiment, alpha may be about 3.6 degrees.

The frame of FIG. 6 also has a length L. It will be appreciated that this length can vary depending on the desired application of the frame. In embodiments where the frame has flare zones at the ends, longer frames may or may not have proportionally longer flare zones. In some embodiments, this flare zone may be any length described above, regardless of the overall length of the frame.

The disclosed frame may be formed in a variety of sizes. In some embodiments, L may be from about 10 mm to about 200 mm. For example, in CV applications the frame may have a length, L, of from about 40 mm to 100 mm or any value between, for example, at least about 50 mm, 60 mm, 70 mm, 80 mm, or 90 mm. In PV applications the frame may have a length, L, of from about 25 mm to 150 mm or any value between, for example at least about 50 mm, 75 mm, 100 mm, or 125 mm. The frame may also be longer or shorter than these exemplary values in other applications.

Likewise the frame may be formed with a variety of diameters. In some embodiments the midbody diameter of the frame may be from about 1 mm to about 45 mm, including from about 4 mm to about 40 mm. For example, in CV or PV applications the frame may have a midbody inside diameter of about 3 mm to 16 mm, or any distance within this range such as between about 5 mm and about 14 mm or between about 7 mm and about 10 mm. Moreover, in some instances, the diameter, or a diameter-like measurement of the frame may be described as a function of other components. For example, the frame may be configured with a particular number of apexes around a circumference of the frame. For example, some frames may be configured with between about 2 and about 30 apexes around a circumference of the frame.

The frame may or may not be configured with flared ends regardless of the midbody diameter employed. In some CV embodiments the maximum diameter at the flared end will be between about 0.5 mm and about 2.5 mm greater than the midbody diameter. For example, the maximum diameter at the flared end may be between about 1 mm and about 2 mm, or alternatively between about 1.25 mm and about 1.5 mm, such as about 1.25 mm or about 1.5 mm greater than the midbody diameter.

Referring now to FIG. 10, the frame may be formed from a single continuous wire. In some embodiments the wire may be comprised of Nitinol (ASTM F2063), or other suitable materials. In some embodiments the wire will have a diameter between about 0.001 inch and about 0.05 inch, including from about 0.005 inch and about 0.025 inch. For example, in some frames designed for CV or PV application, the wire diameter may be from about 0.008 inch to about 0.012 inch in diameter including certain embodiments where the wire is from about 0.009 inch to about 0.011 inch in diameter or embodiments where the wire is about 0.010 inch in diameter. Furthermore, frames configured for the thoracic aorta may be formed of wires up to 0.020 inch in diameter, including wires between about 0.010 inch and about 0.018 inch in diameter.

FIG. 10 illustrates how, in some embodiments, the wire 650 may be wound in a helical pattern creating coils that incline along the length of the stent. The waves of the wire which form the arms and apexes may be centered around this helix, represented by the dashed line 660.

In some embodiments, a stent, graft, or other tubular device may comprise a tapered segment along the length of the device. A taper may be configured to reduce the velocity of fluid flow within the device as the fluid transitions from a smaller diameter portion of the device to a larger diameter portion of the device. Reducing the fluid velocity may be configured to promote laminar flow, including instances wherein a tubular member is tapered to promote laminar flow at the downstream end of the device.

Figure 23A:
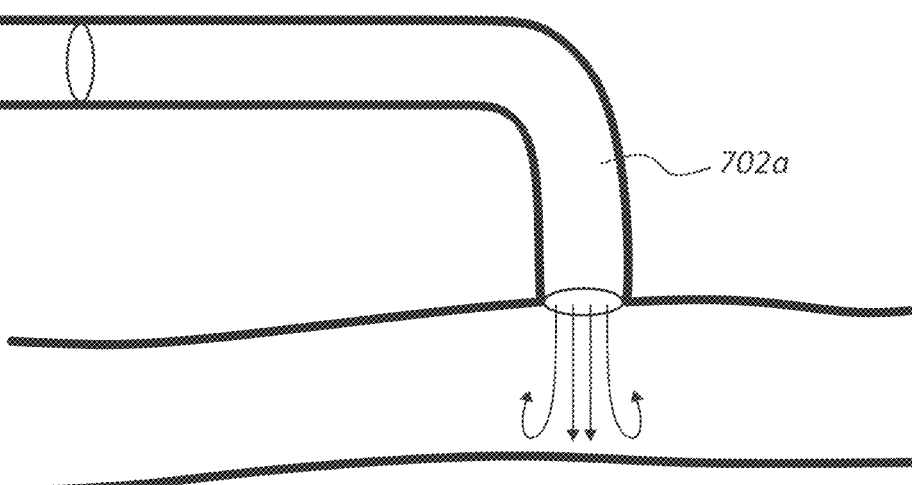
FIG. 23A is a cross-sectional view of two body lumens with a stent disposed therein.

Further, in some embodiments, a stent or other tubular member may be positioned at a junction between two or more body lumens. For example, FIG. 23A illustrates a stent 702a disposed at an intersection between two body lumens. In some embodiments, stent 702a may be configured to promote laminar flow at the intersection of the lumens.

Figure 23B:
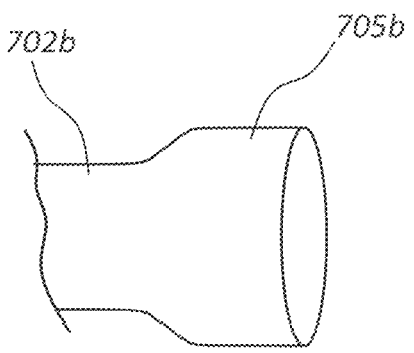
FIG. 23B is a side view of a portion of a stent comprising a tapered segment.
Figure 23C:
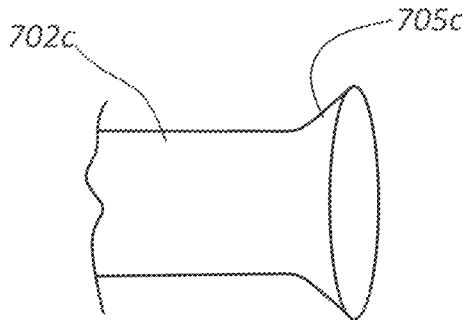
FIG. 23C is a side view of another embodiment of a stent comprising a tapered segment.

FIG. 23B illustrates a portion of a stent 702b having a tapered segment 705b which may be configured to reduce flow velocity within the stent 702b. In some embodiments, such as that of FIG. 23B, the tapered segment 705b may be positioned upstream of the downstream end of the stent 702b. FIG. 23C illustrates another exemplary embodiment of a portion of a stent 702c having a tapered segment 705c adjacent the downstream end of the stent 702c. Either tapered segment (705b, 705c) may be used in connection with any stent, including embodiments wherein the tapered segment is configured to promote laminar flow in and around the stent. For example, the stent 702a of FIG. 23A may be configured with either tapered portion (705b, 705c) to promote laminar flow out of the stent 702a and at the junction between the body lumens of FIG. 23A.

Use of rotational spun coatings may facilitate application of a covering of uniform thickness along a tapered stent. For example, in some embodiments, rotational spun coatings may be configured to evenly coat devices comprised of various geometries. A rotational spun coating may deposit a substantially even coating along various geometries such as tapers, shoulders, and so forth.

EXAMPLES

A number of exemplary PTFE mats were produced according to the disclosure above. FIGS. 11A-20 are SEMs of the PTFE mats produced in each exemplary process. The following examples are intended to further illustrate exemplary embodiments and are not intended to limit the scope of the disclosure.

Example 1

A 60 wt % PTFE water dispersion was mixed with PEO and water as follows. Water was added to PEO to maintain a ratio of 2.86 ml of water per gram of PEO. The water and PEO were mixed until the PEO was fully dissolved and the solution created a thick gel. 25.71 ml of 60 wt % PTFE aqueous dispersion was added to the dissolved PEO to obtain a 0.05 g/ml mixture of PEO to PTFE dispersion. The mixture was strained through a 70 micrometer or finer filter to remove any large particles. The combined solution was then allowed to sit and/or mixed in a non-agitating jar roller until the solution achieved homogeneity; in some instances that process takes 24 to 48 hours.

The combined solution was then rotational spun from a spinneret at about 3000 RPM and collected on a 2 inch by 2 inch sheet of aluminum foil. The collection sheet was positioned about 10 inches from the spinneret. The orifices on the spinneret were about 30 gauge openings. The mat was then sintered at about 385 degrees C. for about 10 minutes.

Small beads were observed on the fibers produced in this example. The resultant mat was about 50 micrometers thick. It was further observed that the mat was generally very open. Similarly, the fiber diameters observed were generally small to medium in diameter.

Figure 11A:
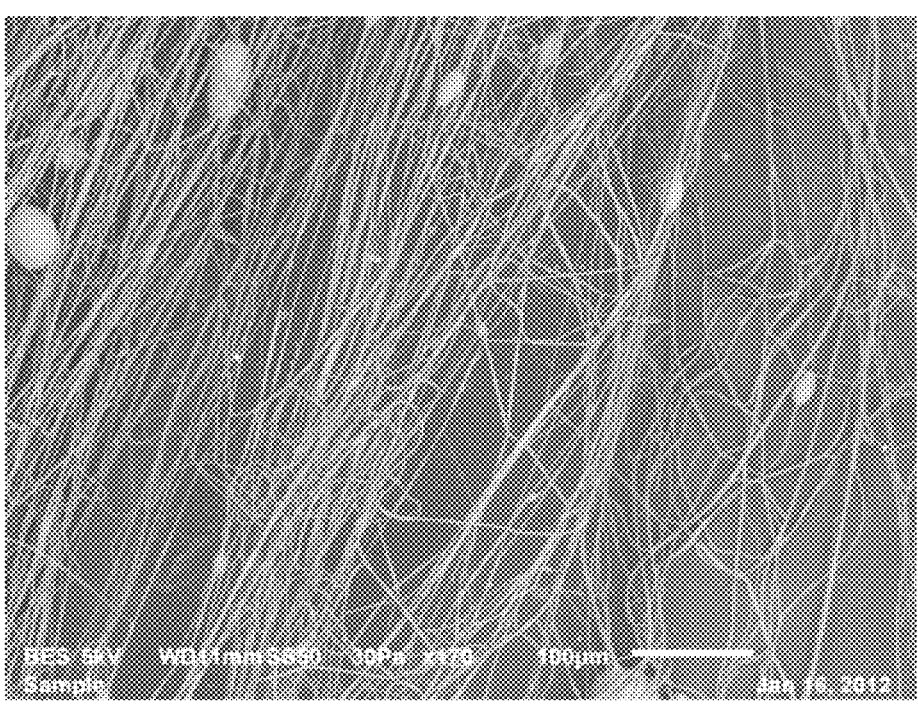
FIG. 11A is a scanning electron micrograph (SEM at 170×) of a rotational spun material created from a PTFE dispersion combined with polyethylene oxide (PEO) and water.
Figure 11B:
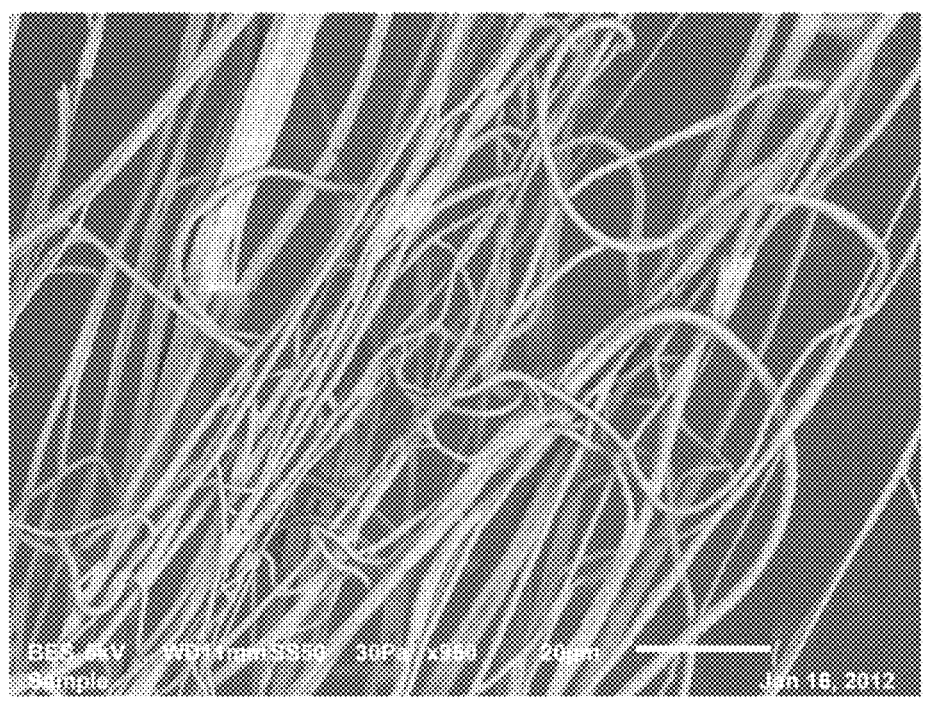
FIG. 11B is an SEM (at 950×) of the material of FIG. 11A.

FIG. 11A is an SEM of the rotational spun PTFE mat created in the procedure of Example 1. FIG. 11A reflects a magnification of 170×. FIG. 11B is an SEM of the rotational spun PTFE of FIG. 11A at a magnification of 950×.

Example 2

A 60 wt % PTFE water dispersion was mixed with PEO and water as follows. Water was added to PEO to maintain a ratio of 2.86 ml of water per gram of PEO. The water and PEO were mixed until the PEO was fully dissolved and the solution created a thick gel. 24.00 ml of 60 wt % PTFE aqueous dispersion was added to the dissolved PEO to obtain a 0.07 g/ml mixture of PEO to PTFE dispersion. The mixture was strained through a 70 micrometer or finer filter to remove any large particles. The combined solution was then allowed to sit and/or mixed in a non-agitating jar roller until the solution achieved homogeneity; in some instances that process takes 24 to 48 hours.

The combined solution was then rotational spun from a spinneret at about 4500 RPM and collected on a 2 inch by 2 inch sheet of aluminum foil. The collection sheet was positioned about 9.5 inches from the spinneret. The orifices on the spinneret were about 30 gauge openings. The mat was then sintered at about 385 degrees C. for about 10 minutes.

The generally random deposition of the fibers as well as the intersecting or crossing nature of fibers may be seen in this example. The resultant mat was about 50 micrometers thick. It was further observed that the mat was generally open. Similarly, the fiber diameters observed were generally of medium diameter.

Figure 12A:
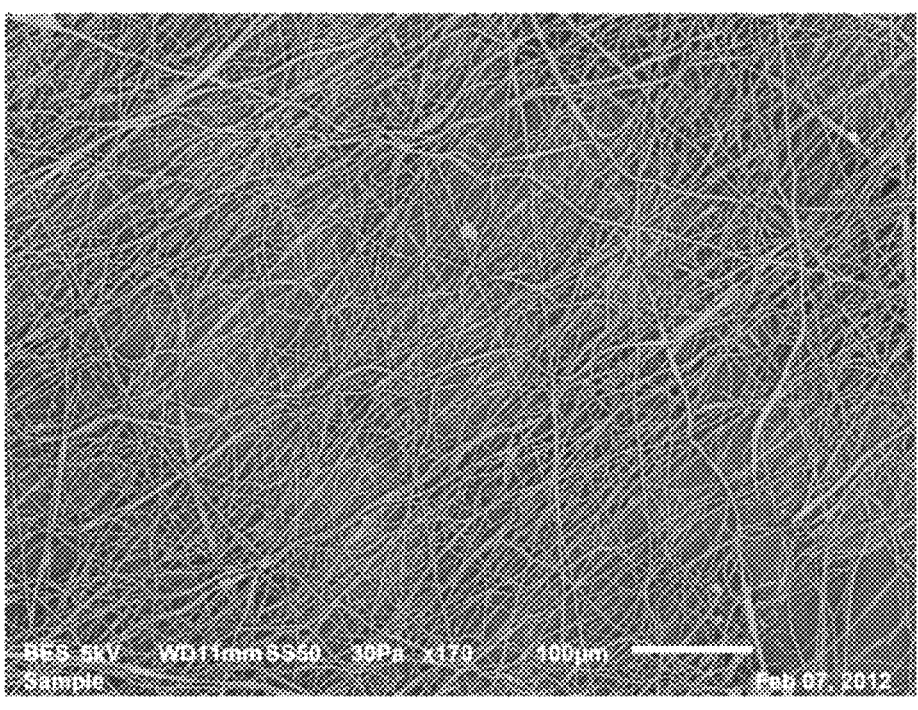
FIG. 12A is an SEM (at 170×) of a rotational spun material having medium fiber diameters which were collected on a sheet.
Figure 12B:
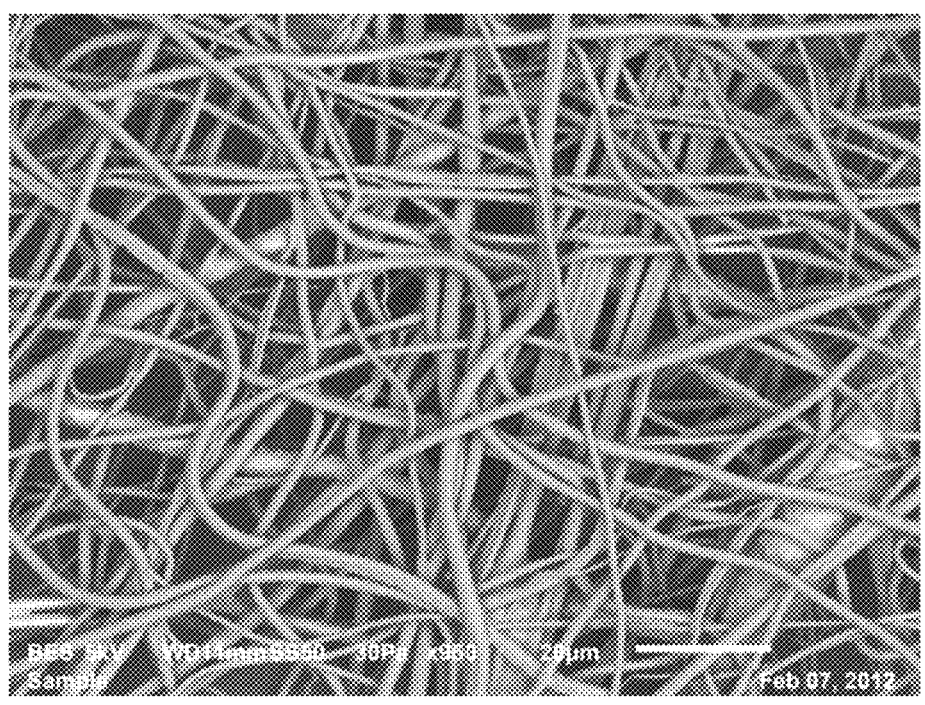
FIG. 12B is an SEM (at 950×) of the material of FIG. 12A.

FIG. 12A is an SEM of the rotational spun PTFE mat created in the procedure of Example 2. FIG. 12A reflects a magnification of 170×. FIG. 12B is an SEM of the rotational spun PTFE of FIG. 12A at a magnification of 950×.

Example 3

A 60 wt % PTFE water dispersion was mixed with PEO and water as follows. Water was added to PEO to maintain a ratio of 2.86 ml of water per gram of PEO. The water and PEO were mixed until the PEO was fully dissolved and the solution created a thick gel. 24.00 ml of 60 wt % PTFE aqueous dispersion was added to the dissolved PEO to obtain a 0.07 g/ml mixture of PEO to PTFE dispersion. The mixture was strained through a 70 micrometer or finer filter to remove any large particles. The combined solution was then allowed to sit and/or mixed in a non-agitating jar roller until the solution achieved homogeneity; in some instances that process takes 24 to 48 hours.

The combined solution was then rotational spun from a spinneret at about 4500 RPM and collected on a 0.5 inch diameter rotating mandrel. The mandrel was rotated at about 200 RPM during this example. The mandrel was positioned about 9.5 inches from the spinneret. The orifices on the spinneret were about 30 gauge openings. The mat was then sintered at about 385 degrees C. for about 10 minutes.

It was observed that the fibers of the mat obtained in this example were generally aligned. The resultant mat was about 50 micrometers thick. It was further observed that the mat was generally less open. Similarly, the fiber diameters observed were generally of medium diameter.

Figure 13A:
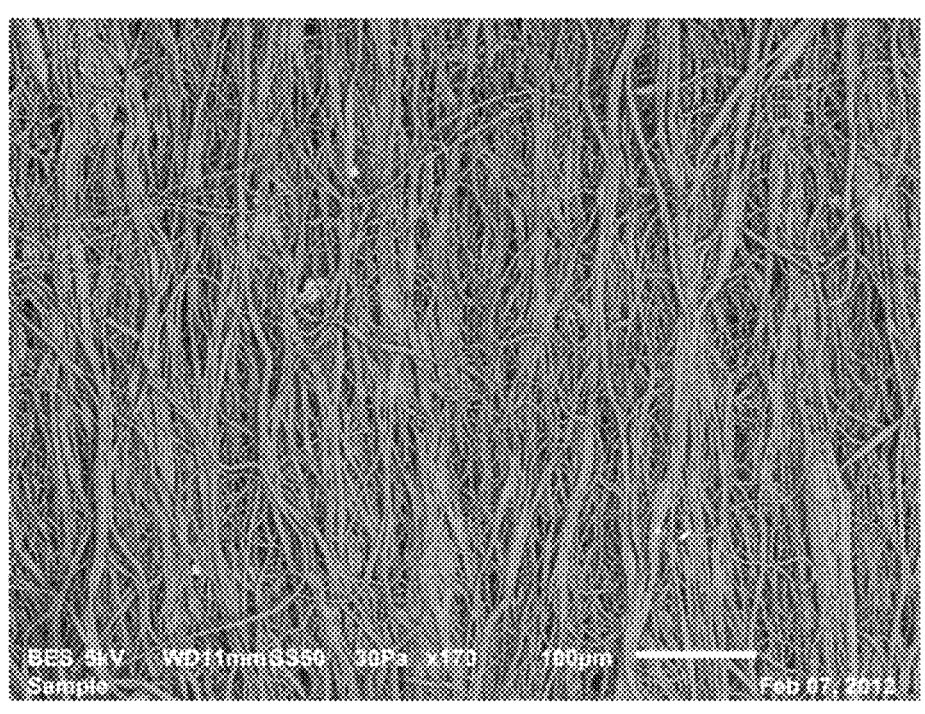
FIG. 13A is an SEM (at 170×) of a rotational spun material having medium fiber diameters which were collected on a rotating mandrel.
Figure 13B:
FIG. 13B is an SEM (at 950×) of the material of FIG. 13A.

FIG. 13A is an SEM of the rotational spun PTFE mat created in the procedure of Example 3. As with FIG. 12A, FIG. 13A reflects a magnification of 170×. FIG. 13A illustrates the generally more aligned dispositions of fibers collected on a rotating mandrel. In particular, comparison of FIGS. 12A and 13A illustrates the effect of the use of a rotating mandrel as opposed to a sheet collector, with respect to fiber alignment. FIG. 13B is an SEM of the rotational spun PTFE of FIG. 13A at a magnification of 950×.

Example 4

A 60 wt % PTFE water dispersion was mixed with PEO and water as follows. Water was added to PEO to maintain a ratio of 2.86 ml of water per gram of PEO. The water and PEO were mixed until the PEO was fully dissolved and the solution created a thick gel. 21.43 ml of 60 wt % PTFE aqueous dispersion was added to the dissolved PEO to obtain a 0.10 g/ml mixture of PEO to PTFE dispersion. The mixture was strained through a 70 micrometer or finer filter to remove any large particles. The combined solution was then allowed to sit and/or mixed in a non-agitating jar roller until the solution achieved homogeneity; in some instances that process takes 24 to 48 hours.

The combined solution was then rotational spun from a spinneret at about 6000 RPM and collected on a 0.5 inch diameter rotating mandrel. The mandrel was rotated at about 200 RPM during this example. The mandrel was positioned about 9.5 inches from the spinneret. The orifices on the spinneret were about 30 gauge openings. The mat was then sintered at about 385 degrees C. for about 10 minutes.

It was observed that the fibers of the mat obtained in this example were generally aligned. The resultant mat was about 50 micrometers thick. It was further observed that the mat was generally open. Similarly, the fiber diameters observed were generally of large diameter.

Figure 14A:
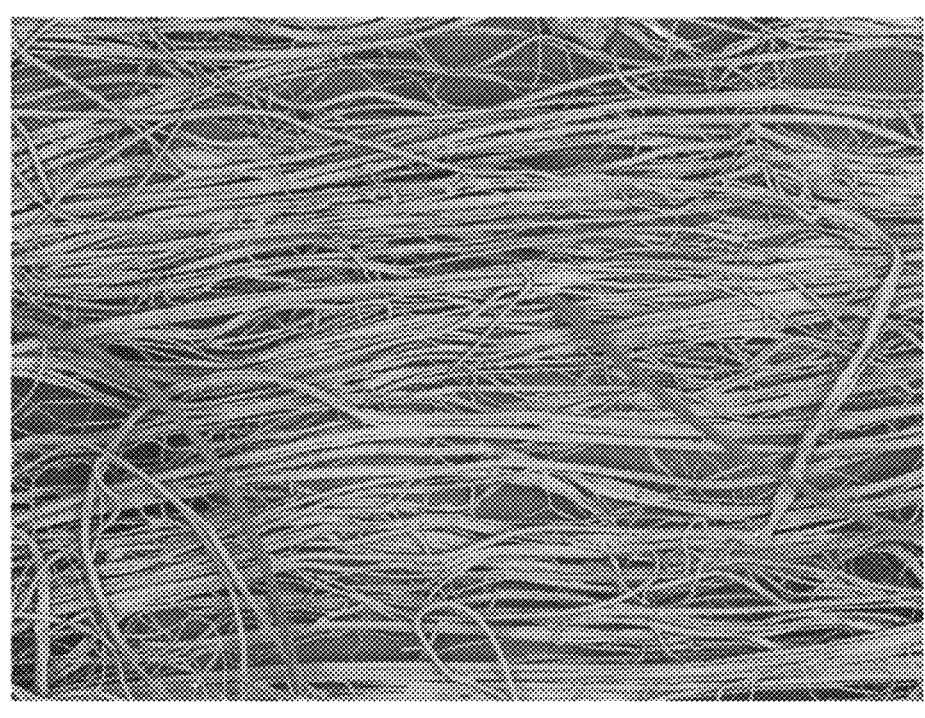
FIG. 14A is an SEM (at 170×) of a rotational spun material having larger fibers which were collected on a rotating mandrel.
Figure 14B:
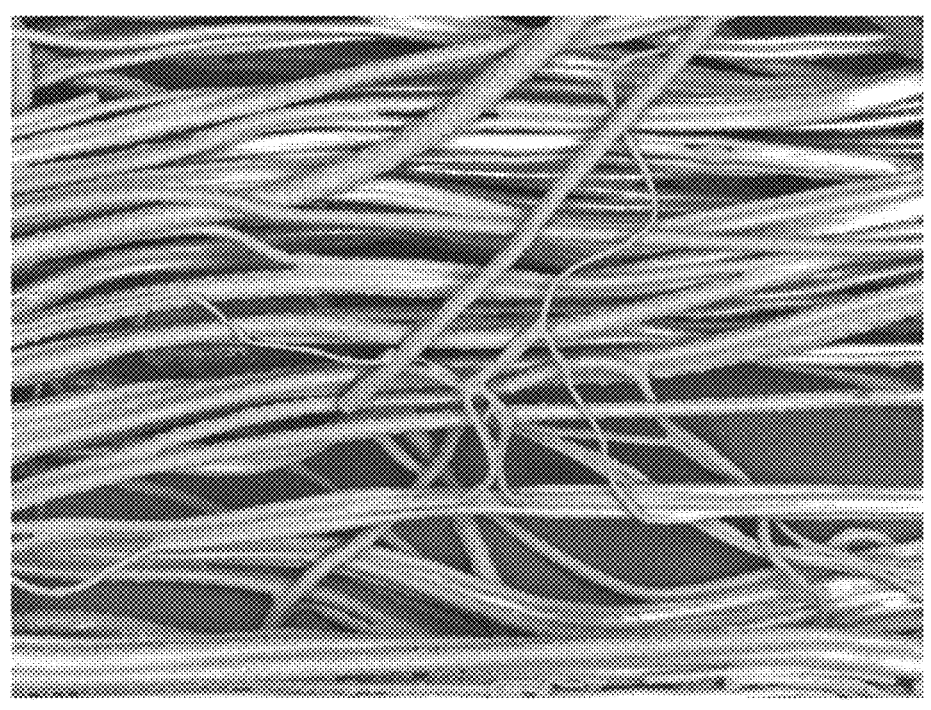
FIG. 14B is an SEM (at 950×) of the material of FIG. 14A.

FIG. 14A is an SEM of the rotational spun PTFE mat created in the procedure of Example 4. FIG. 14A reflects a magnification of 170×. FIG. 14B is an SEM of the rotational spun PTFE of FIG. 14A at a magnification of 950×.

Example 5

A 60 wt % PTFE water dispersion was mixed with PEO and water as follows. Water was added to PEO to maintain a ratio of 2.86 ml of water per gram of PEO. The water and PEO were mixed until the PEO was fully dissolved and the solution created a thick gel. 20.56 ml of 60 wt % PTFE aqueous dispersion was added to the dissolved PEO to obtain a 0.11 g/ml mixture of PEO to PTFE dispersion. The mixture was strained through a 70 micrometer or finer filter to remove any large particles. The combined solution was then allowed to sit and/or mixed in a non-agitating jar roller until the solution achieved homogeneity; in some instances that process takes 24 to 48 hours.

The combined solution was then rotational spun from a spinneret at about 8000 RPM and collected on a 2 inch by 2 inch sheet of aluminum foil. The collection sheet was positioned about 9.5 inches from the spinneret. The orifices on the spinneret were about 30 gauge openings. The mat was then sintered at about 385 degrees C. for about 10 minutes.

It was observed that the mat created in this example had a large distribution of fiber diameters, including some very large fibers. The resultant mat was about 50 micrometers thick. It was further observed that the mat was generally open. Similarly, the fiber diameters observed were generally of large diameter.

Figure 15:
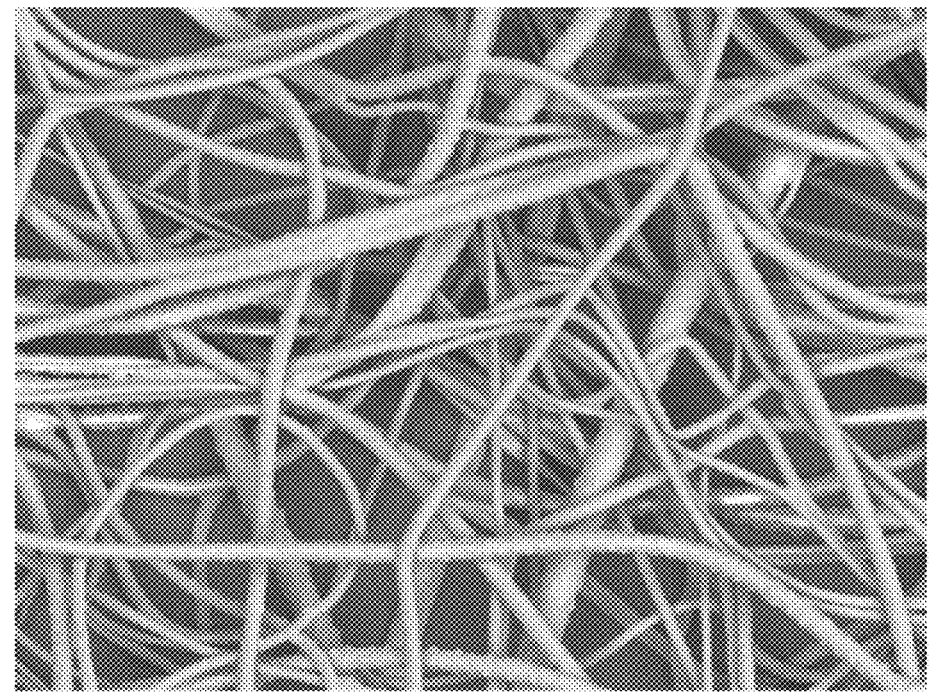
FIG. 15 is an SEM (at 950×) of a rotational spun material having larger fibers which were collected on a sheet.

FIG. 15 is an SEM of the rotational spun PTFE mat created in the procedure of Example 5. FIG. 15 reflects a magnification of 950×.

Example 6

A 60 wt % PTFE water dispersion was mixed with PEO and water as follows. Water was added to PEO to maintain a ratio of 2.86 ml of water per gram of PEO. The water and PEO were mixed until the PEO was fully dissolved and the solution created a thick gel. 21.43 ml of 60 wt % PTFE aqueous dispersion was added to the dissolved PEO to obtain a 0.10 g/ml mixture of PEO to PTFE dispersion. The mixture was strained through a 70 micrometer or finer filter to remove any large particles. The combined solution was then allowed to sit and/or mixed in a non-agitating jar roller until the solution achieved homogeneity; in some instances that process takes 24 to 48 hours.

The combined solution was then rotational spun from a spinneret at about 6000 RPM and collected on a 2 inch by 2 inch sheet of aluminum foil. The collection sheet was positioned about 9.5 inches from the spinneret. The orifices on the spinneret were about 30 gauge openings. The mat was then sintered at about 385 degrees C. for about 10 minutes.

No beading was observed on the fibers of this mat. The resultant mat was about 50 micrometers thick. It was further observed that the mat was generally less open. Similarly, the fiber diameters observed were generally of medium diameter.

Figure 16A:
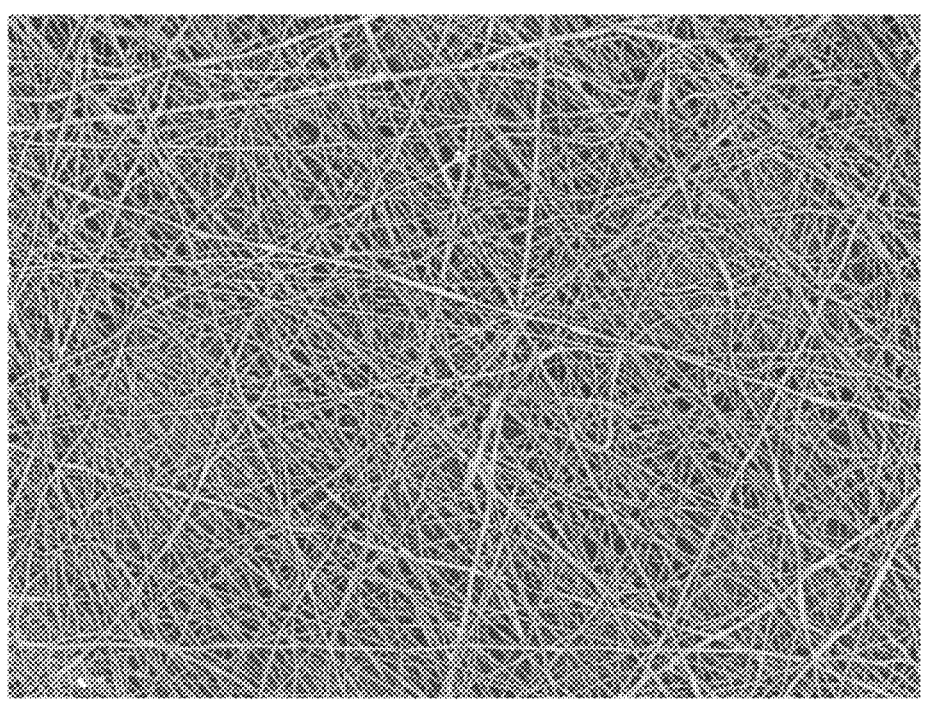
FIG. 16A is an SEM (at 170×) of a rotational spun material having medium fibers which were collected on a sheet.
Figure 16B:
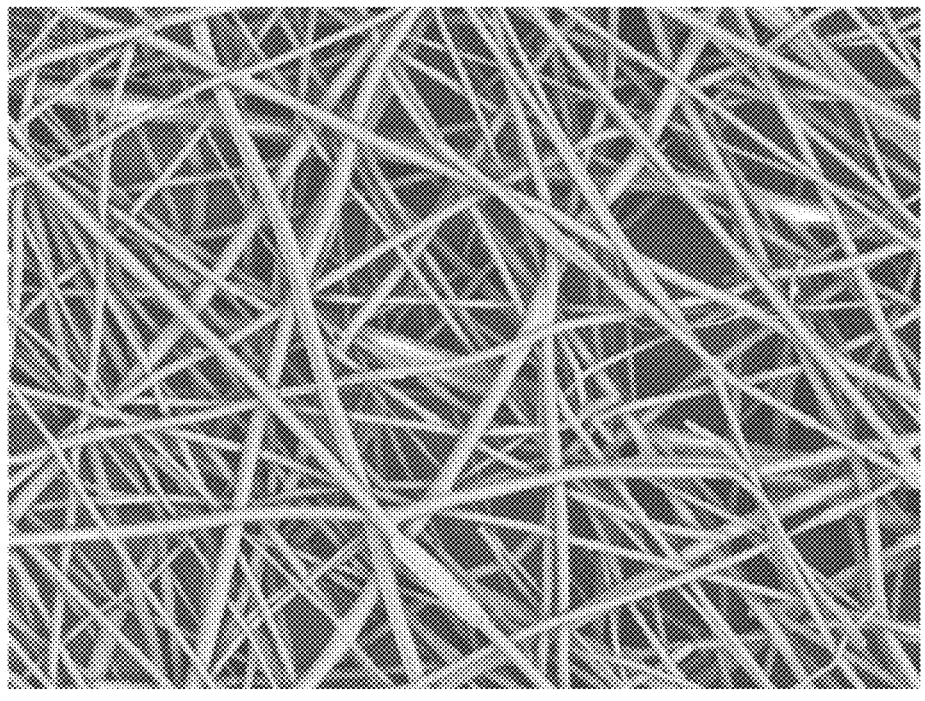
FIG. 16B is an SEM (at 950×) of the material of FIG. 16A.

FIG. 16A is an SEM of the rotational spun PTFE mat created in the procedure of Example 6. FIG. 16A reflects a magnification of 170×. FIG. 16B is an SEM of the rotational spun PTFE of FIG. 16A at a magnification of 950×.

Example 7

A 60 wt % PTFE water dispersion was mixed with PEO and water as follows. Water was added to PEO to maintain a ratio of 2.86 ml of water per gram of PEO. The water and PEO were mixed until the PEO was fully dissolved and the solution created a thick gel. 25.71 ml of 60 wt % PTFE aqueous dispersion was added to the dissolved PEO to obtain a 0.05 g/ml mixture of PEO to PTFE dispersion. The mixture was strained through a 70 micrometer or finer filter to remove any large particles. The combined solution was then allowed to sit and/or mixed in a non-agitating jar roller until the solution achieved homogeneity; in some instances that process takes 24 to 48 hours.

The combined solution was then rotational spun from a spinneret at about 3000 RPM and collected on a 2 inch by 2 inch sheet of aluminum foil. The collection sheet was positioned about 10 inches from the spinneret. The orifices on the spinneret were about 30 gauge openings. The mat was then sintered at about 385 degrees C. for about 10 minutes.

This example produced the smallest diameter fibers of the examples herein disclosed. The resultant mat was about 50 micrometers thick. It was further observed that the mat was generally closed. Again, the fiber diameters observed were generally of small diameter.

Figure 17A:
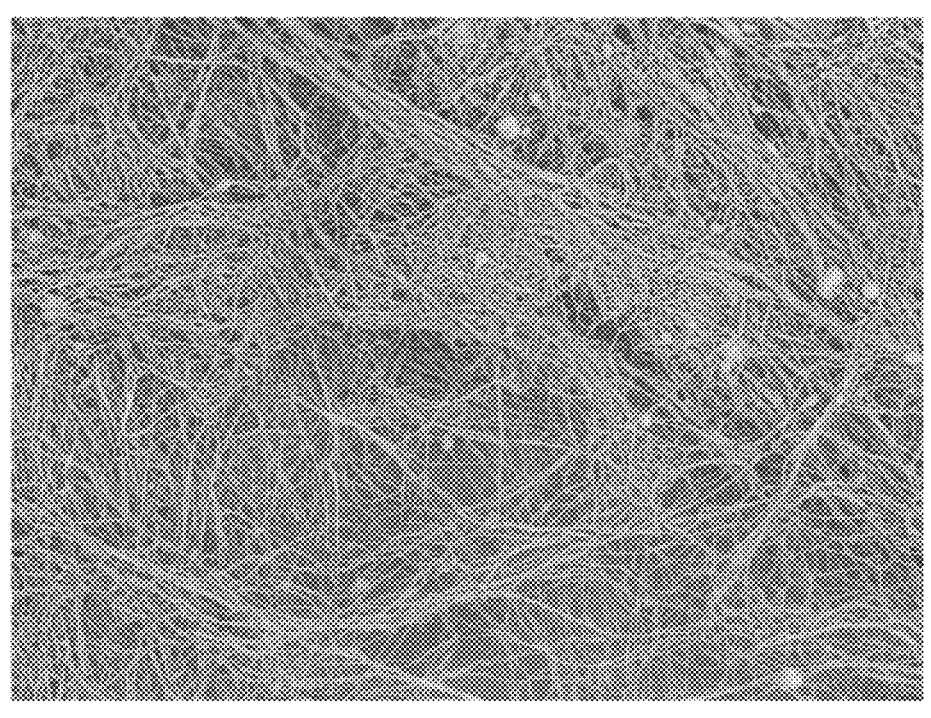
FIG. 17A is an SEM (at 170×) of a rotational spun material having smaller fibers which were collected on a sheet.
Figure 17B:
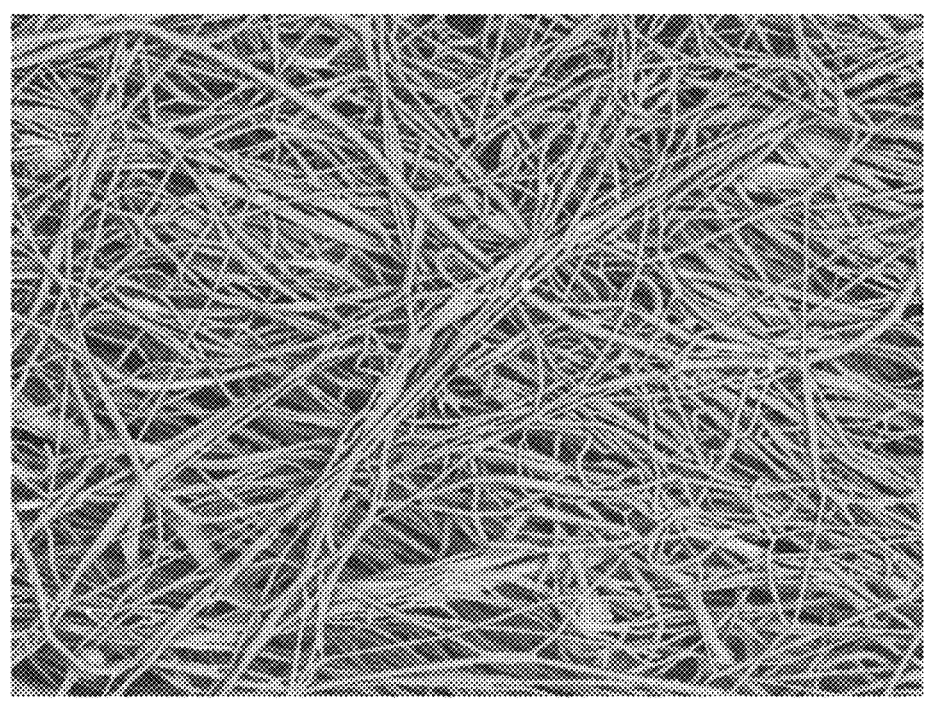
FIG. 17B is an SEM (at 950×) of the material of FIG. 17A.

FIG. 17A is an SEM of the rotational spun PTFE mat created in the procedure of Example 7. FIG. 17A reflects a magnification of 170×. FIG. 17B is an SEM of the rotational spun PTFE of FIG. 17A at a magnification of 950×.

Example 8

A 60 wt % PTFE water dispersion was mixed with PEO and water as follows. Water was added to PEO to maintain a ratio of 2.86 ml of water per gram of PEO. The water and PEO were mixed until the PEO was fully dissolved and the solution created a thick gel. 24.00 ml of 60 wt % PTFE aqueous dispersion was added to the dissolved PEO to obtain a 0.07 g/ml mixture of PEO to PTFE dispersion. The mixture was strained through a 70 micrometer or finer filter to remove any large particles. The combined solution was then allowed to sit and/or mixed in a non-agitating jar roller until the solution achieved homogeneity; in some instances that process takes 24 to 48 hours.

The combined solution was then rotational spun from a spinneret at about 3500 RPM and collected on a 0.5 inch diameter rotating mandrel. The mandrel was rotated at about 200 RPM during this example. The mandrel was positioned horizontally in this example. The mandrel was positioned between about 4 inches and about 6 inches away from the spinneret, along the length of the mandrel. The orifices on the spinneret were about 30 gauge openings. The mat was then sintered at about 385 degrees C. for about 10 minutes.

The resultant mat was about 45 micrometers thick. It was further observed that the mat was generally closed. Similarly, the fiber diameters observed were generally of medium diameter.

Figure 18A:
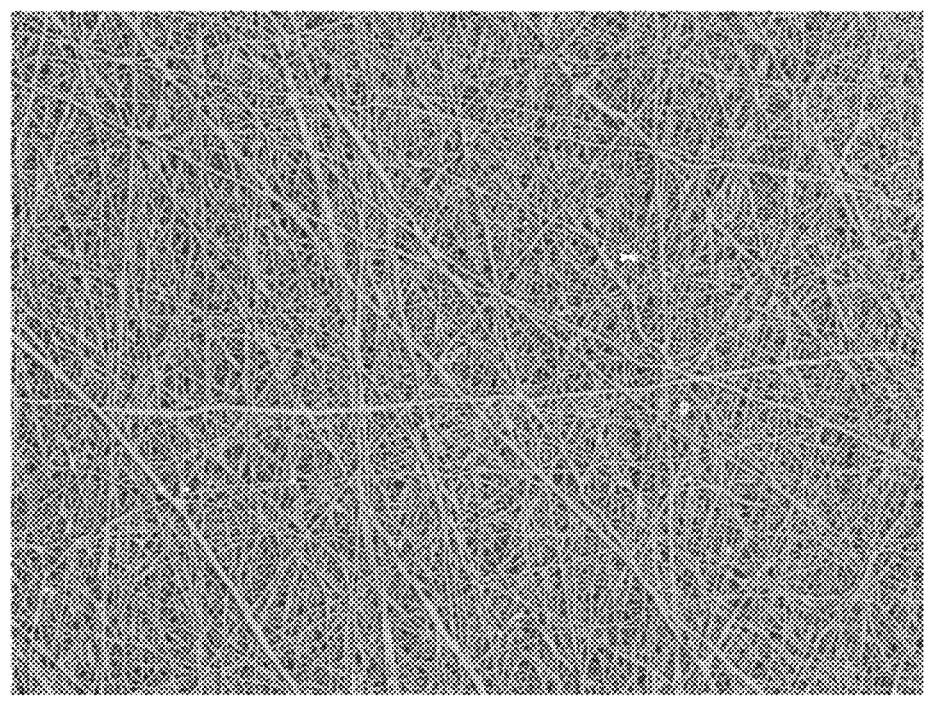
FIG. 18A is an SEM (at 170×) of a rotational spun material collected on a horizontally mounted mandrel.
Figure 18B:
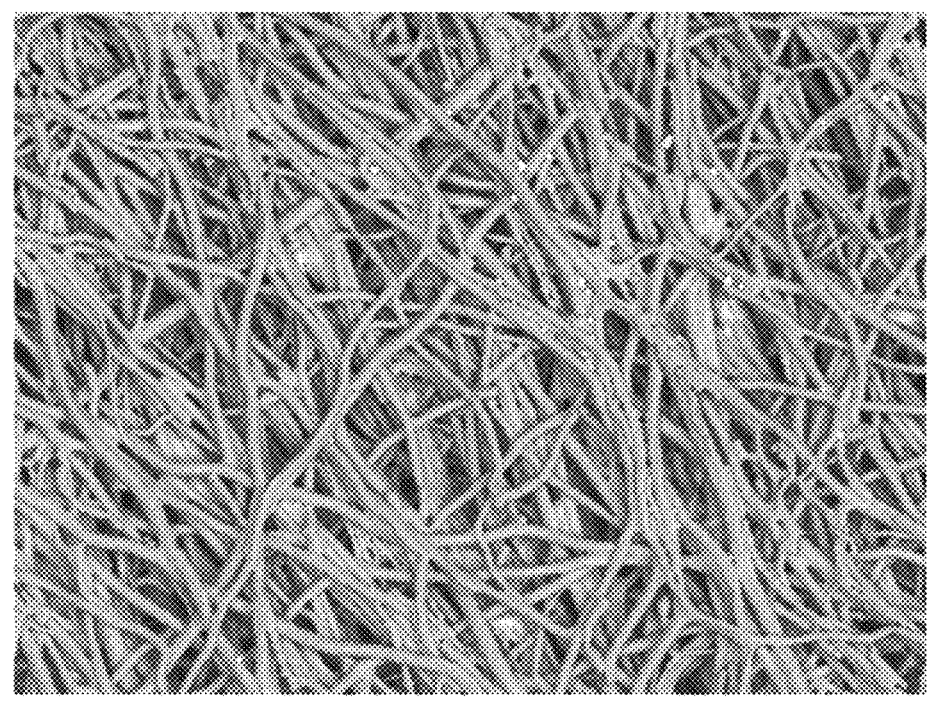
FIG. 18B is an SEM (at 950×) of the material of FIG. 18A.

FIG. 18A is an SEM of the rotational spun PTFE mat created in the procedure of Example 8. FIG. 18A reflects a magnification of 170×. FIG. 18B is an SEM of the rotational spun PTFE of FIG. 18A at a magnification of 950×.

Example 9

Two separate nanofiber tubes were produced on a horizontal rotating mandrel and each tube removed from the mandrel. Each tube was produced according to the same procedure recited in Example 8. The first of the two tubes was then placed on a 0.5 inch diameter mandrel and a solid, 0.001 inch thick FEP film was wrapped one time around the first tube and mandrel. The FEP film was tacked in place with a soldering iron at about 320 degrees C.

The second nanofiber tube was then pulled over the FEP film layer and the entire construct placed in an oven for about 21 minutes at about 330 degrees C. The construct was removed from the oven and allowed to cool, and the construct removed from the mandrel.

Figure 19:
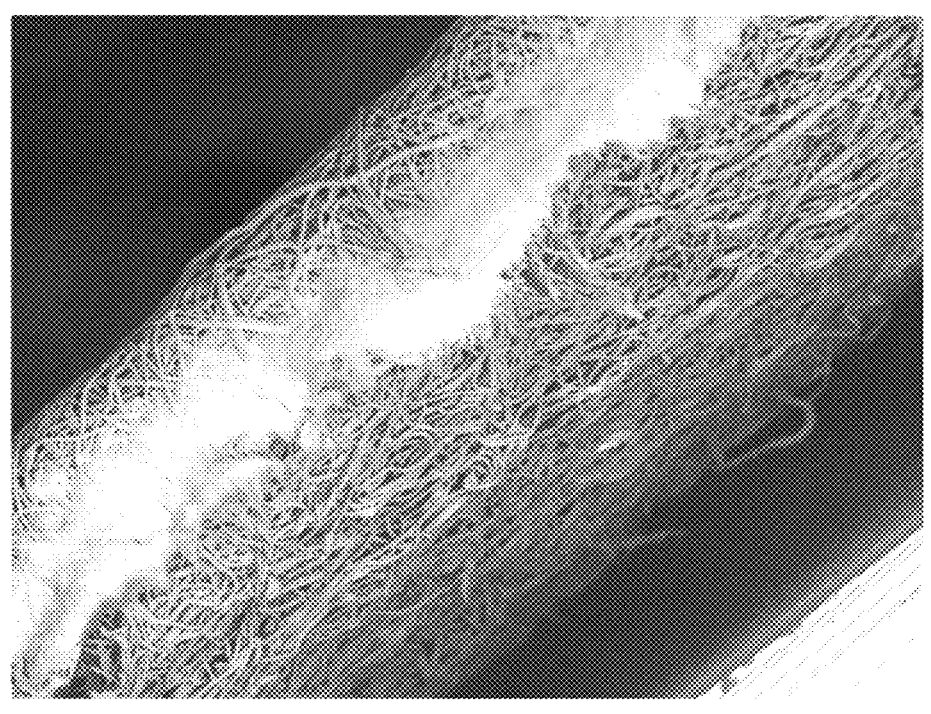
FIG. 19 is a cross sectional view (at 370×) of an exemplary construct of multiple layers of rotational spun materials.

FIG. 19 is a cross sectional view of this layered construct at a magnification of 370×. As shown in this figure, the top and bottom layers comprise nanofiber mats, while the middle FEP layer may be configured to be more impervious to tissue ingrowth and/or attachment.

Example 10

A 0.07 g/ml mixture of PEO to PTFE dispersion was rotational spun from a spinneret at about 3500 RPM and collected on a rotating mandrel. The mandrel was rotated at about 200 RPM and was positioned horizontally in this example. The mandrel was positioned between about 4 inches and about 6 inches away from the spinneret, along the length of the mandrel. The orifices on the spinneret were about 30 gauge openings. The mat was then sintered at about 385 degrees C. for about 10 minutes.

An FEP film was then placed around the mat and mandrel and an overwrap material applied to compress the construct. The construct was then heated to about 330 degrees C. for about 21 minutes. The FEP partially melted and flowed into the gaps or open spaces in the initially formed mat. The compression wrap was then removed.

FIG. 20 is an SEM of the PTFE/FEP construct at a magnification of 950×. The disposition and interaction of the FEP with respect to the PTFE can be seen.

Example 11: Endothelial Cell Attachment Assay

In some embodiments, the degree of endothelial cell attachment to a material may be determined according to the following assay. As used herein, values for "in vitro endothelial cell attachment" are determined by following the procedure disclosed below.

In this assay, rotational spun PTFE sample materials were tested to determine their ability to support the growth and/or attachment of porcine aortic endothelial cells. One set of sample materials was obtained from one of the rotational spun PTFE nanofiber mats described in the preceding Examples. Further, materials A-I, described in Example 14, infra, were also analyzed.

First, a standard curve with a range of endothelial cell seeding densities was generated to correlate with the PTFE material samples. To generate this curve, a 96 well plate was prepared with duplicate sets of 0, 2.5K, 5K, 10K, 20K, 40K, 60K, and 80K endothelial cells per well in complete media. The endothelial cells were allowed to attach to the well for 90 minutes at 37° C. in 5% $CO_2$. At 90 minutes, 50 μl of a working stock of 1 mg/ml XTT (2,3-Bis-(2-Methoxy-4-Nitro-5-Sulfophenyl)-2H-Tetrazolium-5-Carboxanilide) and 32 μM PMS (5-Methylphenazinium methyl sulfate) was added to each well and incubated at 37° C. in 5% $CO_2$ for 3 hours. Actively respiring cells convert the water-soluble XTT, in the presence of intermediate electron acceptor PMS, to a water-soluble, orange formazan product. Thus, after the incubation period, formazan is in solution in the media in each well. Following incubation, the media in each well was uniformly mixed by pipetting and 150 μl was transferred to wells in a new 96 well plate. Once media from the standards and unknowns (described later) were transferred to this plate, the optical density (OD) of each well was read at 450 nm and at 650 nm. The background absorbance at 650 nm, was subtracted from the 450 nm absorbance and the results were graphed.

As used herein, "optical density" measures the absorbance of light in the solution. In this example, the greater the number of cells which attach to the material, and are available to react with the XTT/PMS, the darker the color of the supernatant (due to an increased amount of formazan) and, therefore, the higher the optical density (or absorbance of light) of the sample. Assuming that all the cells in the experiment convert XTT to its formazan derivative at the same rate, the optical density measurement is directly proportional to the number of attached cells.

To quantify the measurements obtained for the test materials, a standard curve was generated by measuring the optical density using the wells known to contain 0, 2.5K, 5K, 10K, 20K, 40K, 60K, and 80K endothelial cells per well. The porcine aortic endothelial cells were cultured on the rotational spun PTFE material samples to measure attachment of endothelial cells to the material samples. In addition to the rotational spun samples, a number of expanded PTFE (ePTFE) material samples were also tested to provide a reference or comparison for the rotational spun materials. The ePTFE material used was the commercially available Bard Impra Straight Thinwall Vascular Graft (Cat #80S06TW), which is often used as a control material in relevant literature as it is known to have a favorable biologic response and favorable endothelial cell attachment.

First the PTFE material samples to be tested and a number of Beem capsules were ETO sterilized. The PTFE material samples were placed within the Beem capsules in an aseptic field. The PTFE materials were pre-wet with 200 µl of D-PBS (Dulbecco's phosphate buffered saline) for 50 minutes. The D-PBS was removed from the Beem capsules containing the PTFE material samples and the Beem capsules were then seeded with 50K endothelial cells in 200 µl of complete media, with the exception of a Beem control capsule which contained complete media only. The media-only Beem capsule control for each test material was processed identically as the Beem capsules seeded with endothelial cells. A standard curve of porcine endothelial cells (previously described) was seeded for each unique assay of test materials.

The endothelial cells were allowed to attach 90 minutes at 37° C. in 5% $CO_2$. At 90 minutes, the Beem capsules were rinsed to remove unattached cells. First the media was carefully removed and discarded. The Beem capsules were then carefully rinsed with 200 µl D-PBS, which was removed and discarded. The Beem capsules then received 200 µl fresh media. 50 µl of working stock of 1 mg/ml XTT (2,3-Bis-(2-Methoxy-4-Nitro-5-Sulfophenyl)-2H-Tetrazolium-5-Carboxanilide) and 32 µM PMS (5-Methylphenazinium methyl sulfate) was added to each Beem capsule and incubated at 37° C. in 5% $CO_2$ for 3 hours. As with the standard curve wells outlined above, the XTT formazan was produced in proportion to the number of attached, live cells within each capsule. The media in each Beem capsule was uniformly mixed by pipetting and 150 µl was transferred to an empty well in the clean 96 well plate containing the supernatants of the standard curve series.

The optical density (OD) of the supernatants was read at 450 nm and 650 nm. The background absorbance at 650 nm, was subtracted from the 450 nm absorbance and the results were graphed. The number of cells attached to each sample was interpolated from the standard curve results.

The number of cells attached to the rotational spun materials were compared by normalizing the results to the number of cells attached the ePTFE control material. The endothelial cell attachment for all of the 10 rotational spun material samples (materials A-I from example 14 and one material from the preceding examples) was between 38.9% and 170% (about 40% to about 170%) of the endothelial cell attachment to the ePTFE control material. Nine of the 10 materials had endothelial cell attachments above 50%; eight of the 10 were above 60%; seven of the 10 were above 70%; five of the 10 were above 80%; four of the ten were above 100%; three of the ten were above 125%; and two of the 10 were above 150% of the endothelial cell attachment of the ePTFE control material.

The materials disclosed herein may be configured to achieve various amounts of in vitro endothelial cell attachment as defined by this assay. As described above, changes to the percent porosity of a mat, the thickness of the mat, and/or the diameter of fibers comprising the mat may influence the characteristics of the mat, including the response of the material to this assay. Thus, materials within the scope of this disclosure may have in vitro endothelial cell attachments of more than 30%, more than 40%, more than 50%, more than 75%, more than 100%, more than 125%, more than 150%, and more than 170% of the endothelial cell attachment of an ePTFE control material.

Example 12: Variations in RPM

Figure 21E:
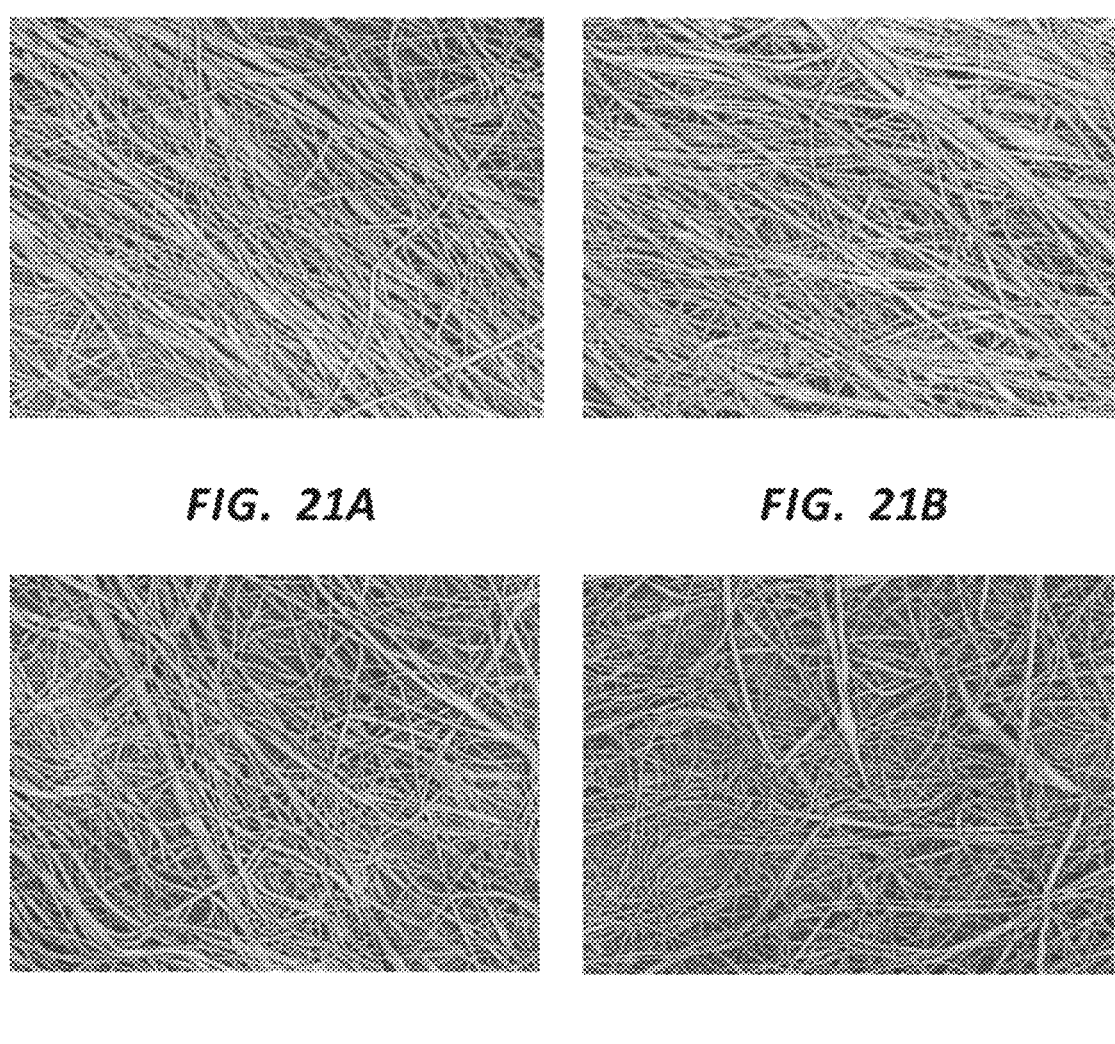
FIG. 21E is an SEM (at 170×) of a rotational spun material spun at 7000 RPM.
Figure 21E:
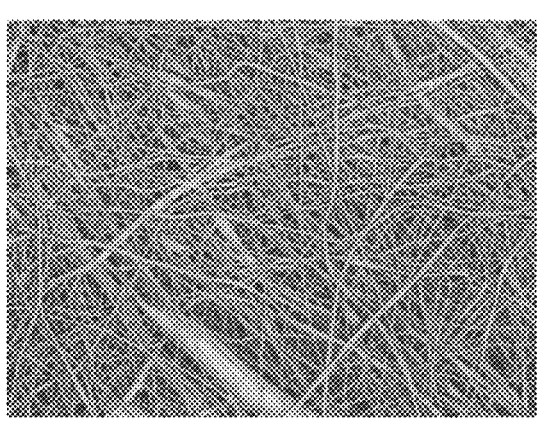

A 0.08 g/ml mixture of PEO to PTFE dispersion was rotational spun from a spinneret at various rotational speeds from about 4500 RPM to about 7000 RPM. The fibers were collected on a flat sheet then sintered at about 385 degrees C. for about 15 minutes. FIGS. 21A-21E are SEMs of five mats produced at different rotational speeds. FIG. 21A (170×) is an SEM of a rotational spun material spun at 4500 RPM. FIG. 21B (170×) is an SEM of a rotational spun material spun at 5000 RPM. FIG. 21C (170×) is an SEM of a rotational spun material spun at 5500 RPM. FIG. 21D (170×) is an SEM of a rotational spun material spun at 6000 RPM. FIG. 21E (170×) is an SEM of a rotational spun material spun at 7000 RPM.

It was observed during this and related experiments that the optimal rotational speed for a dispersion depended at least partially on other parameters, such as the viscosity of the solution. In some embodiments, it was observed that particularly high or particularly low rotational speeds results in mats with particularly large fiber diameters, spray, broken fibers, or cracks. A variety of rotational speeds may be utilized, depending on, for example, the type of material to be spun and the viscosity or other parameters of a particular solution. In some embodiments wherein a PEO/PTFE mixture is spun from a dispersion, rotational speeds may vary between about 1000 RPM and about 10,000 RPM, including rotational speeds from about 3000 RPM to about 5500 RPM.

Example 13: Variations in PEO/PTFE Concentration

Figure 22A:
FIG. 22A is an SEM (at 170×) of a rotational spun material spun from a 0.08 g/ml PEO/PTFE mixture.
Figure 22A:
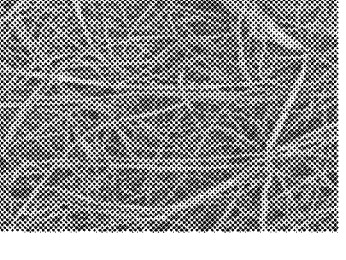
Figure 22A:
Figure 22B:
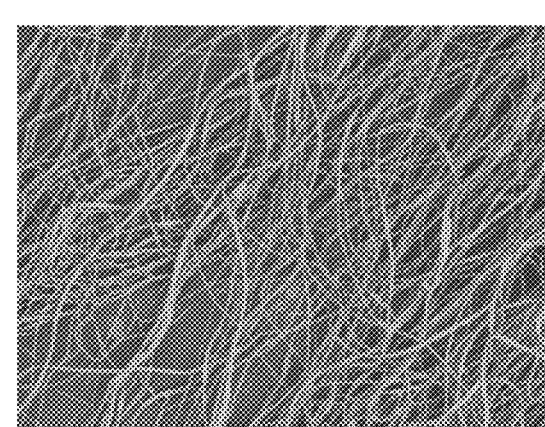
FIG. 22B is an SEM (at 170×) of a rotational spun material spun from a 0.09 g/ml PEO/PTFE mixture.
Figure 22C:
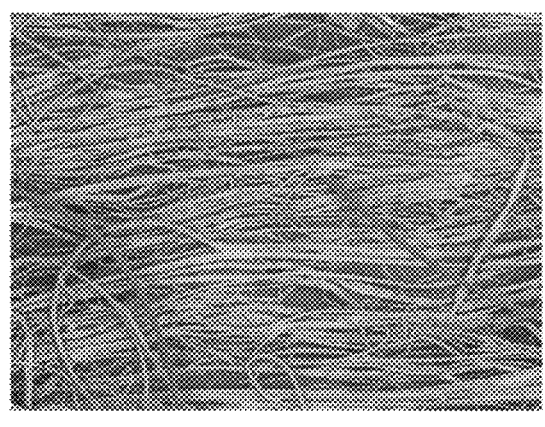
FIG. 22C is an SEM (at 170×) of a rotational spun material spun from a 0.10 g/ml PEO/PTFE mixture.
Figure 22C:
Figure 22D:
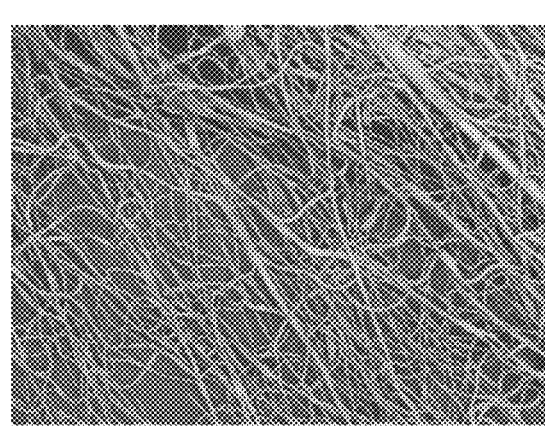
FIG. 22D is an SEM (at 170×) of a rotational spun material spun from a 0.11 g/ml PEO/PTFE mixture.

As discussed in connection with Example 12, the viscosity of a dispersion or mixture to be spun may affect fiber and mat formation. In this example, various concentrations of PEO to PTFE dispersion were rotational spun at 5000 RPM. The fibers were collected on a flat sheet then sintered at about 385 degrees C. for about 15 minutes. FIGS. 22A-22D are SEMs of four mats produced by spinning four different concentrations. FIG. 22A (170×) is an SEM of a rotational spun material spun from a 0.08 g/ml PEO/PTFE mixture. FIG. 22B (170×) is an SEM of a rotational spun material spun from a 0.09 g/ml PEO/PTFE mixture. FIG. 22C (170×) is an SEM of a rotational spun material spun from a 0.10 g/ml PEO/PTFE mixture. FIG. 22D (170×) is an SEM of a rotational spun material spun from a 0.11 g/ml PEO/PTFE mixture.

The mixtures having higher concentrations of PEO to PTFE dispersion tended to be more viscous than lower concentrations. Again, it was observed that the viscosity of the mixture and the concentration of PEO affected the formation and deposition of fibers on the collector. A variety of mixtures and viscosities may be utilized, depending on, for example, the type of material to be spun and other parameters of the particular solution. In some embodiments wherein a PEO/PTFE mixture is spun from a dispersion, concentrations of PEO to PTFE dispersion may range from about 0.08 g/ml to about 0.11 g/ml.

Example 14: In Vivo Biologic Response

Nine rotational spun PTFE mats, labeled materials A-I below, and three multilayered constructs, labeled materials J, K, and L below, were prepared to evaluate the relative biocompatibility of the materials in vivo. Materials A-I were prepared by rotationally spinning a 0.06 g/ml PEO/PTFE mixture, collecting the fibers, and sintering the mats at 385 degrees C. Various needle gauge sizes and rotational speeds were used to create the materials, as shown in Table 1 below. Each of materials A-I was measured to have a percent porosity between about 45% and about 50%.

TABLE 1

| Material | Needle Size (gauge) | RPM |
|---|---|---|
| A | 32 | 7500 |
| B | 32 | 7500 |
| C | 32 | 7500 |
| D | 30 | 4500 |
| E | 30 | 4500 |
| F | 27 | 3500 |
| G | 27 | 3500 |
| H | 27 | 3500 |
| I | 27 | 5500 |

The three multilayered constructs were prepared by rotationally spinning a 0.06 g/ml PEO/PTFE mixture using 30 gauge needles at 3500 RPM. The fibers were collected and sintered at 385 degrees C. The PTFE mats were then combined with additional film or dip layers as indicated in Table 2 below. "RS Mat" in Table 2 indicates a rotational spun PTFE mat prepared as described in this paragraph.

TABLE 2

| Material | Layer 1 | Layer 2 | Layer 3 |
|---|---|---|---|
| J | RS Mat | FEP Film | RS Mat |
| K | RS Mat | FEP Dip | RS Mat |
| L | RS Mat | FEP/PTFE Dip | RS Mat |

In addition to materials A-L, two commercially available expanded PTFE stent graft materials, labeled ePTFE 1 and ePTFE 2 below, were also evaluated for comparison. Expanded PTFE (ePTFE) is a material produced by stretching a sheet or membrane of PTFE. Materials ePTFE 1 and ePTFE 2 are used for implantation within the human body and are generally understood to have favorable biocompatibility. Additionally, a portion of an expanded PTFE vascular graft material, labeled ePTFE Control below, was also evaluated. This material is a commercially available ePTFE material produced by Bard which is often used as a positive control material in relevant literature, as it generally exhibits a favorable biologic response. Finally, a polypropylene material, labeled PP Control, was evaluated as a negative control. PP Control was utilized as a negative control as it is generally understood to elicit a moderate to high inflammatory biologic response.

Pledgets of materials A-L, ePTFE 1, ePTFE 2, ePTFE Control, and PP Control were cut or punched for subcutaneous implantation in murine models. Multiple samples of each material were prepared. The samples were ETO sterilized. The subjects were prepared for sterile surgical procedures. Each subject was ear tagged for unique study identification and the ability to evaluate subjects based on subject number to maintain an investigator-blinded analysis of the data, prior to decoding the data.

Each animal used in the study was randomly enrolled and received between 4 and 5 subcutaneous implants; all implants in a single subject were of the same type of material facing the same direction. Documentation of each animal and the type of materials implanted were recorded on individual animal surgery forms.

Following two weeks of implantation, all subjects were euthanized and then implanted materials and surrounding tissue were explanted. Explants were immediately placed into 2% paraformaldehyde fixative for up to 48 hours and then changed into a 70% ethanol solution for subsequent processing for paraffin embedding. Prior to paraffin embedding, each sample was cut in half and mounted into paraffin with the fresh cut side down. Samples processed for histology and immunohistochemistry were stained with hematoxlyin and eosin or trichrome, or reacted with antibodies for CD-68 (a marker for activated macrophages).

A. Inflammatory Score

The inflammatory response to the various implanted materials was compared. To quantify the inflammatory response, an established equation was used to provide weight to staining intensities and provide a quantitative value to the macrophage and foreign body gain cell (FBGC) counts. The equation was based on equations currently used by pathologists in cancer research called the H-score (Nakopoulou et al., Human Pathology vol. 30, no. 4, April 1999). The H-score was obtained by the formula:

$$(3\times\text{percentage of strongly staining nuclei})+(2\times\text{percentage of moderately staining nuclei})+(\text{percentage of weakly staining nuclei})=\text{a range of 0 to 300}$$

The inflammatory score obtained by this formula can be further indexed using a qualitative approach considering the following criteria (Nakoploulou et al., 1999):

0=negative [0 to 50], 1=mild reactivity [51 to 100], 2=moderate [101 to 200], 3=strong reactivity [201 to 300]

Figure 24:
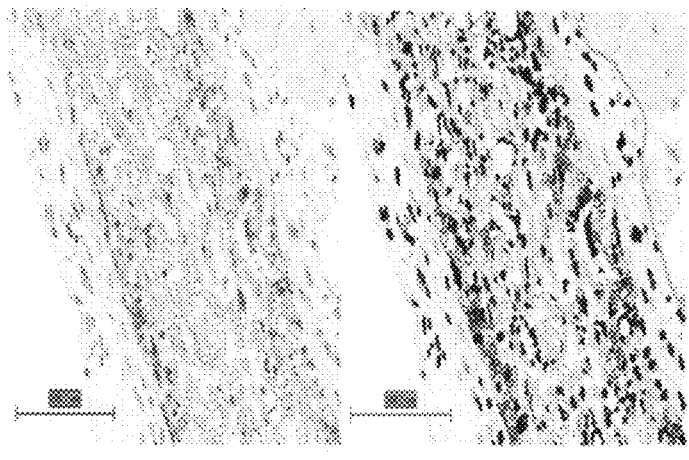
FIG. 24 is an immunonistochemistry light microscopy color image of a portion of an explanted material sample and a digitally marked up copy of the same image.

Strongly staining nuclei were represented by red in a false color mark-up in a digital algorithm, moderately stained nuclei were represented by orange in the false color mark-up, and weakly stained nuclei were represented by yellow. FIG. 24 is a color image of a stained slide for one sample, within the original stained slide on the left, and the digitally enhanced mark-up of the same image on the right. In the marked-up slide, red, orange, and yellow represent the staining level described above, while blue is negative. The black bar on the image is a 100 μm scale bar. Similar slides for each sample were analyzed. By inserting the counts from the marked up slides into the formula above, a quantitative inflammatory response was obtained for each sample. The inflammatory score for each material was calculated as the average of the scores of each sample of the same material. A one-way ANOVA analysis with a Tukey post-hoc test ($p<0.05$) was used to assess statistical differences.

All of the 12 materials, A-L described above, were measured to have an inflammatory H-score under 100, meaning all 12 materials were either mildly reactive or not reactive at all. 10 of the 12 materials were measured to have an inflammatory H-score under 90, seven to have an inflammatory H-score under 70, five to have an inflammatory H-score under 55, three to have an inflammatory H-score under 50, and two to have an inflammatory H-score under 40.

By comparison, materials ePTFE 1 and ePTFE had average inflammatory H-scores of about 67 and about 85, respectively. The ePTFE Control material had an average inflammatory H-score of about 52 and the PP Control had an average inflammatory H-score of about 153. Thus, by comparison, materials A-L exhibited inflammatory H-scores which were comparable to, or more favorable than, the comparative materials generally understood to have favorable biologic responses. Further, each of the materials A-L exhibited a lower inflammatory H-score than the more reactive PP Control.

B. Fibrous Capsule Evaluation

Figure 25:
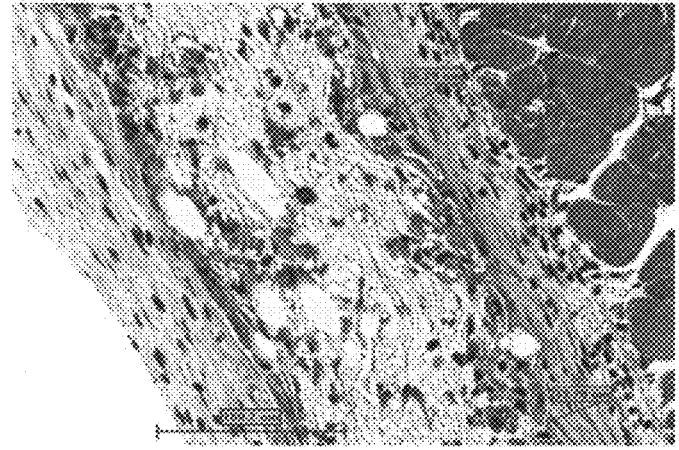
FIG. 25 is a color image of a trichrome-stained histology light microscopy image for a portion of one explanted material sample.

The presence of a fibrous capsule on each sample was evaluated from measurements performed approximately 100 μm from the ends of each sample and then every 100 μm across the superficial surface of each sample. The average fibrous capsule for each type of material was determined by averaging the measurements obtained from each sample of each type of material. FIG. 25 is an exemplary color image of a trichrome-stained histology light microscopy image for one sample. The width of the fibrous capsule, measured at two points in the image, is shown marked up on the image. Further a 100 μm scale bar is shown on the image. Similar images were analyzed for each sample. A one-way ANOVA analysis with a Tukey post-hoc test (p<0.05) was used to assess statistical differences.

All of the 12 materials, A-L described above, were measured to have an average fibrous capsule thickness of less than 35 μm, with 10 of 12 having an average thickness of less than 30 μm, nine having an average thickness of less than 25 μm, five having an average thickness of less than 20 μm, and three having an average thickness of less than 15 μm.

By comparison, materials ePTFE 1 and ePTFE had average fibrous capsule thicknesses of about 31 μm and about 20 μm, respectively. The ePTFE Control material had an average fibrous capsule thickness of about 22 μm and the PP Control had an average fibrous capsule thickness of about 20 μm. As with the inflammatory H-score, it was noted that materials A-L exhibited average fibrous capsule thicknesses which were similar to, or more favorable than, the comparative materials generally known to have good biocompatibility.

C. Cellular Penetration

Figure 26:
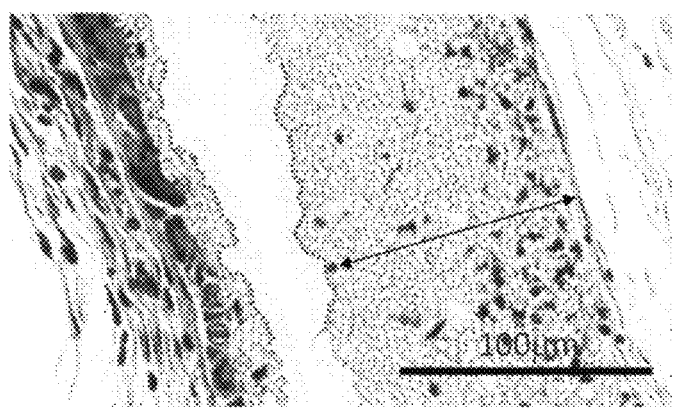
FIG. 26 is color image of a trichrome-stained histology light microscopy image for a portion of an explanted material sample having multiple layers.

Cellular penetration as a percentage of material thickness was determined by performing measurements of the material thickness at 100 μm intervals across each sample, as well as measuring the depth of cellular penetration from the superficial surface toward the midline. The percent of cellular penetration was only measured on the superficial side of the samples. FIG. 26 is color image of a trichrome-stained histology light microscopy image for one sample of material J, a three layered construct comprising a film FEP layer between two layers of rotational spun PTFE. The dotted red lines marked up on the image indicate the boundaries of the FEP layer, with the rotational spun PTFE layers on either side. The double black arrow indicates the relative distance of cellular penetration and the positive stain indicates the presence of cells within the material. Similar slides were analyzed for each sample, and the results averaged for each material. A one-way ANOVA analysis with a Tukey post-hoc test (p<0.05) was used to assess statistical differences.

Of the nine single layer materials, A-I, described above, eight were measured to have an average cellular penetration of above 98%, with six averaging 99.99% or above. One of the nine materials, A-I, had an average cellular penetration of about 64%. By comparison, materials ePTFE 1 and ePTFE had an average cellular penetration of about 23% and about 33%, respectively. The ePTFE Control material had an average cellular penetration of about 23% and the PP Control had an average cellular penetration of zero, meaning the material was substantially impervious to cellular ingrowth. Thus, all nine of the single layer materials, A-I, were found to exhibit greater cellular penetration than the comparative materials generally known to have good biocompatibility. Furthermore, the difference in cellular penetration between each of materials A-I and any of ePTFE 1, ePTFE 2, the ePTFE Control, and the PP Control were shown to be statistically significant.

Materials J-L were multilayered constructs, meaning the total cellular penetration may be impacted by the presence of multiple layers. In some instances it may be desirable to construct a stent having certain layers configured to permit cellular penetration and certain layers configured to resist cellular penetration. For example, a stent may comprise inner and outer layers configured to permit cellular ingrowth with a mid-layer configured to resist such ingrowth. The outer and inner layers may be configured to increase the biocompatability of the construct while the mid-layer resists growth completely through the construct (which may lead to restenosis). The slide of FIG. 26 illustrates one such embodiment, having permeable outer layers and a mid-layer configured to resist ingrowth. As shown in FIG. 26, the slide indicates essentially 100 percent cellular penetration in the rotational spun outer layers, as shown by the presence of stained cells in this material. On the other hand, the FEP layer, indicated by the dashed red lines, shows substantially no cellular penetration. The dipped constructions exhibited a similar response, with the dipped layers showing substantially no cellular penetration.

Exemplary Embodiments

The following embodiments are illustrative and exemplary and not meant as a limitation of the scope of the present disclosure in any way.

I. Medical Appliance

In one embodiment a medical appliance comprises a first layer of rotational spun polytetrafluoroethylene (PTFE).

The rotational spun PTFE may comprise a mat of PTFE nanofibers.

The rotational spun PTFE may comprise a mat of PTFE microfibers.

The rotational spun PTFE may be rotational spun through an orifice.

The medical appliance may further comprise a second layer of rotational spun PTFE fibers, wherein the first layer of rotational spun PTFE is disposed such that it defines a first surface of the medical appliance and the second layer of rotational spun PTFE is disposed such that it defines a second surface of the medical appliance.

The first layer of rotational spun PTFE may have an average percent porosity between about 30% and about 80%.

The first layer of rotational spun PTFE may have an average percent porosity of between about 40% and about 60%.

The first layer of rotational spun PTFE may have an average pore size configured to permit tissue ingrowth on the first surface of the medical appliance.

The first layer of rotational spun PTFE may permit tissue ingrowth.

The second layer of rotational spun PTFE may have an average percent porosity of about 50% or less.

The second layer of rotational spun PTFE may have an average pore size configured to resist tissue ingrowth into or through the second surface of the medical appliance.

The medical appliance may further comprise a cuff adjacent to an end of the medical appliance, the cuff configured to permit tissue ingrowth into or tissue attachment to the cuff.

A tie layer may be disposed between the first layer of rotational spun PTFE and the second layer of rotational spun PTFE.

The tie layer may be configured to inhibit tissue ingrowth into or through the tie layer.

The tie layer may be configured to inhibit fluid migration through the tie layer.

The first and second layers of rotational spun PTFE and the tie layer may be configured to inhibit an unfavorable inflammatory response.

The first and second layers of rotational spun PTFE and the tie layer may be configured to inhibit hyperplastic tissue growth including neointimal or psuedointimal hyperplasia.

The tie layer may comprise PTFE.

The tie layer may be a thermoplastic polymer.

The tie layer may be a fluorinated ethylene propylene (FEP).

The FEP may partially bond to the fibers of the first and second layers of rotational spun PTFE.

The FEP may flow into and coat the fibers of the first and second layers of rotational spun PTFE.

The FEP may coat the fibers of the first and second layers while maintaining the porosity of the layers.

The rotational spun PTFE may be formed from a mixture comprising PTFE, polyethylene oxide (PEO), and water.

The mixture may be formed by combining a PTFE dispersion with PEO dissolved in water.

The PTFE may be rotational spun in the absence of an electric field.

The medical appliance may further comprise a main lumen extending to a bifurcation and two branch lumens extending from the bifurcation.

The medical appliance may further comprise a main lumen and one or more branch lumens extending from a wall of the main lumen.

The medical appliance may further comprising a reinforcing layer.

The reinforcing layer may comprise a tie layer.

The reinforcing layer may be comprised of expanded PTFE (ePTFE).

The ePTFE may be oriented to impart a particular property in a particular direction.

The ePTFE may be oriented to resist creep in at least one direction.

The medical appliance may comprise multiple reinforcing layers configured to impart one or more properties in one or more directions.

II. Stent

In one embodiment, a stent comprises a frame configured to resist radial compression when disposed in a lumen of a patient, and a covering disposed on at least a portion of the scaffolding structure, the covering comprising a first layer of rotational spun polytetrafluoroethylene (PTFE).

The rotational spun PTFE may comprise a mat of PTFE nanofibers.

The rotational spun PTFE may comprise a mat of PTFE microfibers.

The rotational spun PTFE may be rotational spun through an orifice.

The stent may further comprise a second layer of rotational spun PTFE fibers, wherein the stent is generally tubular in shape and the first layer of rotational spun PTFE is disposed such that it defines an inside surface of the stent and the second layer of rotational spun PTFE is disposed such that it defines an outside surface of the stent.

The first layer of rotational spun PTFE may have an average percent porosity between about 30% and about 80%.

The first layer of rotational spun PTFE may have an average percent porosity of between about 40% and about 60%.

The first layer of rotational spun PTFE may have an average pore size configured to permit the tissue ingrowth on the inside surface of the stent.

The first layer of rotational spun PTFE may permit tissue ingrowth.

The second layer of rotational spun PTFE may have an average percent porosity of about 50% or less.

The second layer of rotational spun PTFE may have an average pore size configured to resist tissue ingrowth into or through the second layer of rotational spun PTFE.

The stent may further comprise a cuff adjacent to an end of the stent, the cuff configured to permit tissue ingrowth into the cuff.

A tie layer may be disposed between the first layer of rotational spun PTFE and the second layer of rotational spun PTFE.

The tie layer may be configured to inhibit tissue ingrowth into the tie layer.

The tie layer may be configured to inhibit fluid migration through the tie layer.

The tie layer may comprise PTFE.

The tie layer may be a thermoplastic polymer.

The tie layer may be fluorinated ethylene propylene (FEP).

The FEP may partially bond to the fibers of the first and second layers of rotational spun PTFE.

The second layer of rotational spun PTFE material may be configured to permit tissue ingrowth into the second layer to reduce device migration.

The first and second layers of rotational spun PTFE and the tie layer may be configured to inhibit hyperplastic tissue growth such as neointimal or psuedointimal hyperplasia.

The first and second layers of rotational spun PTFE and the tie layer may be configured to inhibit an unfavorable inflammatory response.

The FEP may flow into and coat the fibers of the first and second layers of rotational spun PTFE.

The FEP may coat the fibers of the first and second layers while maintaining the porosity of the layers.

The rotational spun PTFE may be formed from a mixture comprising PTFE, polyethylene oxide (PEO), and water.

The mixture may be formed by combining a PTFE dispersion with PEO dissolved in water.

The rotational spun PTFE may be rotational spun onto a rotating mandrel.

The PTFE may be rotational spun in the absence of an electric field.

The frame may be comprised of a single wire.

The wire may be helically wound around a central axis of the stent.

The wire may have a wave-like pattern defining apexes and arms.

Alternating apexes adjacent an end of the stent may have different relative heights.

Each apex may have a radius of between about 0.12 mm and 0.64 mm.

The stent may have a first portion disposed near the midbody of the stent and second and third portions disposed near the ends of the stent, and the arms disposed within the second and third portions may be relatively longer than the arms disposed within the first portion.

A distance, apex to apex length, may be defined as the distance between a first apex and a second apex wherein the first apex lies on a first coil of wire and the second apex lies on a second coil of wire adjacent to the first coil, and wherein the first apex and the second apex lie substantially on a line on the outer surface of the stent, the line being co-planar with and parallel to a central axis of the stent, wherein the apex to apex distance may be smaller at the midbody of the stent, relative to the apex to apex distance near the ends of the stent.

The stent may be structured such that a midbody portion of the stent is relatively less compressible than a first and a second end of the stent.

The stent may further comprise a main lumen extending to a bifurcation and two branch lumens extending from the bifurcation.

The stent may further comprise a main lumen and one or more branch lumens extending from a wall of the main lumen.

The stent may further comprise a reinforcing layer.

The reinforcing layer may comprise a tie layer.

The reinforcing layer may be comprised of expanded PTFE (ePTFE).

The ePTFE may be oriented to impart a particular property in a particular direction.

The ePTFE may be oriented to resist creep in at least one direction.

The stent may comprise multiple reinforcing layers configured to impart one or more properties in one or more directions.

III. Method of Constructing a Medical Appliance

In one embodiment, a method of constructing a medical appliance comprises rotationally spinning a first tube of polytetrafluoroethylene (PTFE) onto a mandrel and sintering the first tube.

The first tube of PTFE may be rotational spun onto a rotating mandrel.

The mandrel may be positioned substantially orthogonal to an axis of rotation of a rotational spinning spinneret.

A second tube of rotational spun PTFE may be applied around the first layer.

A scaffolding structure may be applied around the first tube and a fluorinated ethylene propylene (FEP) layer may be applied around the first tube and the scaffolding structure, prior to applying the second tube of rotational spun PTFE.

The FEP layer may be configured to inhibit tissue ingrowth into or through the FEP layer.

The medical appliance may be heated such that the FEP layer bonds to the first and second tubes.

The FEP may partially bond to the fibers of the first and second tubes.

The FEP may flow into and coat the fibers of the first and second tubes.

The FEP may coat the fiber of the first and second tubes while maintaining the porosity of the tubes.

The second tube of rotational spun PTFE may be formed by rotational spinning the second tube of PTFE onto a rotating mandrel and sintering the second tube.

A compressive wrap may be applied around the second tube before the medical appliance is heat treated.

Rotational spinning the first tube of PTFE may comprise mixing a PTFE dispersion with polyethylene oxide (PEO), wherein the PEO is dissolved in water to form a mixture, and discharging the mixture from an orifice onto a rotating mandrel.

The mixture may be discharged by centrifugal force.

A cuff may be coupled to an end of the medical appliance, the cuff configured to permit tissue ingrowth into the cuff.

The PTFE may be rotational spun in the absence of an electric field.

The mandrel may comprise a main portion and two leg portions, the main portion configured to coincide with a main lumen of a bifurcated medical appliance and the two leg portions configured to coincide with leg portions of bifurcated medical appliance.

The two leg portions of the mandrel may be removable from the main portion of the mandrel.

The first tube may be rotational spun by rotating the mandrel about an axis of the leg portions of the mandrel while rotationally spinning fibers and rotating the mandrel about an axis of the main portion of the mandrel while rotationally spinning fibers.

IV. Method for Promoting Endothelial Cell Growth

In one embodiment, a method for promoting endothelial cell growth on a implantable medical appliance comprises implanting the medical appliance into a patient, the medical appliance coated with at least one spun fibrous polymer layer having a percent porosity of between about 30% and about 80%, such that endothelial cells grow on or attach to the surface of the at least one polymer layer.

The implantable medical appliance may comprise a covered stent or a stent graft.

The implantable medical appliance may comprise a graft.

The at least one fibrous polymer layer may comprise a fibrous PTFE layer.

The medical appliance may be coated with a second polymer layer that inhibits ingrowth of tissue.

The second polymer layer may comprise an FEP layer.

The fibrous PTFE may comprise a fiber mat of rotationally-spun randomized PTFE microfibers or nanofibers.

The at least one polymer layer of the implanted medical appliance may be configured to permit at least 50% in vitro endothelial cell attachment, compared to an ePTFE control material.

The at least one polymer layer of the implanted medical appliance may be configured to permit at least 75% in vitro endothelial cell attachment, compared to an ePTFE control material.

The at least one polymer layer of the implanted medical appliance may be configured to permit at least 100% in vitro endothelial cell attachment, compared to an ePTFE control material.

The at least one polymer layer of the implanted medical appliance may be configured to permit at least 125% in vitro endothelial cell attachment, compared to an ePTFE control material.

The at least one polymer layer of the implanted medical appliance may be configured to permit at least 150% in vitro endothelial cell attachment, compared to an ePTFE control material.

The percent porosity of the at least one polymer layer may be between about 40% and about 60%.

In any of the above methods for promoting endothelial cell growth, the spun fibrous polymer layer may be configured to permit at least 50%, 75%, 90%, 95%, or 100% cellular penetration, in vivo two weeks after murine implantation.

In any of the above methods for promoting endothelial cell growth, the spun fibrous polymer layer may be configured to inhibit a neointimal hyperplasia response.

In any of the above methods for promoting endothelial cell growth, the spun fibrous polymer layer, when placed in vivo, may have an H-score of less than 100, 90, 70, or 50 two weeks after murine implantation.

In any of the above methods for promoting endothelial cell growth, the spun fibrous polymer layer, when placed in vivo, may be configured to resist fibrous capsule formation, such that the spun fibrous polymer layer has an average fibrous capsule thickness of less than 35 μm, 30 μm, 25 μm, 20 μm, or 15 μm two weeks after murine implantation.

V. Method for Promoting Cellular Growth into an Implantable Medical Appliance

In one embodiment, a method for promoting cellular growth into an implantable medical appliance comprises obtaining a medical appliance coated with at least one spun fibrous polymer layer and at least one layer that is substantially impervious to cellular growth, and implanting the medical appliance into a patient such that the fibrous polymer layer of the medical appliance is in direct contact with body fluid or body tissue.

The at least one fibrous polymer layer may be configured to permit at least 50% cellular penetration, in vivo two weeks after murine implantation.

The at least one fibrous polymer layer may be configured to permit at least 75% cellular penetration, in vivo two weeks after murine implantation.

The at least one fibrous polymer layer may be configured to permit at least 90% cellular penetration, in vivo two weeks after murine implantation.

The at least one fibrous polymer layer may be configured to permit at least 95% cellular penetration, in vivo two weeks after murine implantation.

The at least one fibrous polymer layer may be configured to permit substantially 100% cellular penetration, in vivo two weeks after murine implantation.

The at least one substantially impervious layer may be configured to permit less than 20% cellular penetration, in vivo two weeks after murine implantation.

The at least one substantially impervious layer may be configured to permit less than 10% cellular penetration, in vivo two weeks after murine implantation.

The at least one substantially impervious layer may be configured to permit substantially no cellular penetration, in vivo two weeks after murine implantation.

The at least one substantially impervious layer may be configured to inhibit fluid migration through the layer.

In any of the above methods for promoting endothelial cell growth on an implantable medical appliance, the at least one fibrous polymer layer may be configured to permit at least 50%, 75%, 100%, 125%, or 150% in vitro endothelial cell attachment, compared to an ePTFE control material.

In any of the above methods for promoting endothelial cell growth on an implantable medical appliance, the at least one fibrous polymer layer may be configured to inhibit a neointimal hyperplasia response.

In any of the above methods for promoting endothelial cell growth on an implantable medical appliance, the at least one fibrous polymer layer, when placed in vivo, may have an H-score of less than 100, 90, 70, or 50 two weeks after murine implantation.

In any of the above methods for promoting endothelial cell growth on an implantable medical appliance, the at least one fibrous polymer layer, when placed in vivo, may be configured to resist fibrous capsule formation, such that the spun fibrous polymer layer has an average fibrous capsule thickness of less than 35 μm, 30 μm, 25 μm, 20 μm, or 15 μm two weeks after murine implantation.

VI. Method for Inhibiting a Neointimal Hyperplasia Response to an Implantable Medical Appliance In one embodiment, a method for inhibiting a neointimal hyperplasia response to an implantable medical appliance comprises implanting the medical appliance into a patient, the medical appliance coated with a spun fibrous polymer layer comprising a porous mat and a second polymer layer that inhibits tissue ingrowth into or through the second polymer layer.

The fibrous polymer layer may permit endothelial cell growth or attachment on the surface of the fibrous polymer layer.

The fibrous polymer layer may comprise a fibrous PTFE layer and the second polymer layer may comprise an FEP layer.

The medical appliance may be coated with a third polymer layer comprising a fibrous PTFE layer, such that the FEP layer is disposed between the fibrous polymer layer and the third polymer layer.

The fibrous polymer layer and the third polymer layer may each comprise a rotational spun micro or nano-fiber PTFE mat.

The second polymer layer may comprise a rotational spun FEP mat.

In any of the above methods for inhibiting a neointimal hyperplasia response to an implantable medical appliance, the fibrous polymer layer may be configured to permit at least 50%, 75%, 100%, 125%, or 150% in vitro endothelial cell attachment, compared to an ePTFE control material.

In any of the above methods for inhibiting a neointimal hyperplasia response to an implantable medical appliance, the fibrous polymer layer may be configured to permit at least 50%, 75%, 90%, or 100% cellular penetration, in vivo two weeks after murine implantation.

In any of the above methods for inhibiting a neointimal hyperplasia response to an implantable medical appliance, the fibrous polymer layer, when placed in vivo, may have an H-score of less than 100, 90, 70, or 50 two weeks after murine implantation.

In any of the above methods for inhibiting a neointimal hyperplasia response to an implantable medical appliance, the fibrous polymer layer, when placed in vivo, may be configured to resist fibrous capsule formation, such that the fibrous polymer layer has an average fibrous capsule thickness of less than 35 μm, 30 μm, 25 μm, 20 μm, or 15 μm two weeks after murine implantation.

VII. Method for Inhibiting an Inflammatory Response to an Implantable Medical Appliance In one embodiment, a method for inhibiting an inflammatory response to an implantable medical appliance, comprises implanting the medical appliance into a patient, the medical appliance coated with a spun fibrous polymer layer wherein the spun fibrous polymer layer, when placed in vivo, has an H-score of less than 100 two weeks after murine implantation.

The spun fibrous polymer layer, when placed in vivo, may have an H-score of less than 90 two weeks after murine implantation.

The spun fibrous polymer layer, when placed in vivo, may have an H-score of less than 70 two weeks after murine implantation.

The spun fibrous polymer layer, when placed in vivo, may have an H-score of less than 50 two weeks after murine implantation.

The fibrous polymer layer may comprise a porous, rotational spun PTFE mat.

In any of the above methods for inhibiting an inflammatory response to an implantable medical appliance, the fibrous polymer layer may be configured to permit at least 50%, 75%, 100%, 125%, or 150% in vitro endothelial cell attachment, compared to an ePTFE control material.

In any of the above methods for inhibiting an inflammatory response to an implantable medical appliance, the fibrous polymer layer may be configured to permit at least 50%, 75%, 90%, 95%, or 100% cellular penetration, in vivo two weeks after murine implantation.

In any of the above methods for inhibiting an inflammatory response to an implantable medical appliance, the fibrous polymer layer may be configured to inhibit a neointimal hyperplasia response.

In any of the above methods for inhibiting an inflammatory response to an implantable medical appliance, the fibrous polymer layer, when placed in vivo, may be configured to resist fibrous capsule formation, such that the fibrous polymer layer has an average fibrous capsule thickness of less than 35 μm, 30 μm, 25 μm, 20 μm, or 15 μm two weeks after murine implantation.

VIII. Method for Inhibiting Growth of a Fibrous Capsule on a Medical Appliance

In one embodiment, a method for inhibiting growth of a fibrous capsule on a medical appliance comprises implanting the medical appliance into a patient, the medical appliance coated with a spun fibrous polymer layer, wherein the fibrous polymer layer, when placed in vivo, is configured to resist fibrous capsule formation, such that the fibrous polymer layer has an average fibrous capsule thickness of less than 35 μm two weeks after murine implantation.

The fibrous polymer layer may have an average fibrous capsule thickness of less than 30 μm two weeks after murine implantation.

The fibrous polymer layer may have an average fibrous capsule thickness of less than 25 μm two weeks after murine implantation.

The fibrous polymer layer may have an average fibrous capsule thickness of less than 20 μm two weeks after murine implantation.

The fibrous polymer layer may have an average fibrous capsule thickness of less than 15 μm two weeks after murine implantation.

The fibrous polymer layer may comprise a porous, rotational spun PTFE mat.

In any of the above methods for method for inhibiting growth of a fibrous capsule on a medical appliance, the fibrous polymer layer may be configured to permit at least 50%, 75%, 100%, 125%, or 150% in vitro endothelial cell attachment, compared to an ePTFE control material.

In any of the above methods for method for inhibiting growth of a fibrous capsule on a medical appliance, the fibrous polymer layer may be configured to permit at least 50%, 75%, 90%, 95%, or 100% cellular penetration, in vivo two weeks after murine implantation.

In any of the above methods for method for inhibiting growth of a fibrous capsule on a medical appliance, the fibrous polymer layer may be configured to inhibit a neointimal hyperplasia response.

In any of the above methods for method for inhibiting growth of a fibrous capsule on a medical appliance, the fibrous polymer layer, when placed in vivo, may have an H-score of less than 100, 90, 70, or 50 two weeks after murine implantation.

While specific embodiments of stents and other medical appliances have been illustrated and described, it is to be understood that the disclosure provided is not limited to the precise configuration and components disclosed. Various modifications, changes, and variations apparent to those of skill in the art having the benefit of this disclosure may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not as a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A medical appliance, comprising:
   a first layer of rotational spun and serially deposited polytetrafluoroethylene (PTFE) fibers deposited in the absence of an electric field;
   a tie layer coupled to the first layer and impervious to cell migration into the tie layer; and
   a second layer of PTFE.

2. The medical appliance of claim 1, wherein the first layer is permeable to cell migration into the first layer.

3. The medical appliance of claim 1, wherein the first layer defines a luminal surface of the medical appliance.

4. The medical appliance of claim 1, wherein the tie layer comprises fluorinated ethylene propylene (FEP).

5. The medical appliance of claim 1, wherein the tie layer is non-porous and non-fibrous.

6. The medical appliance of claim 1, wherein the second layer is permeable to cell migration into the second layer.

7. The medical appliance of claim 1, wherein the second layer comprises expanded polytetrafluoroethylene (ePTFE).

8. A medical appliance, comprising:
   a first layer of rotational spun polymeric fibers;
   a tie layer coupled to the first layer, wherein the tie layer is impervious to cellular migration into the tie layer; and
   a second layer of PTFE.

9. The medical appliance of claim 8, wherein the first layer defines a luminal surface of the medical appliance.

10. The medical appliance of claim 8, wherein the rotational spun polymeric fibers are serially deposited in the absence of an electric field.

11. The medical appliance of claim 8, wherein the first layer is permeable to cell migration into the first layer.

12. The medical appliance of claim 8, wherein the first layer of rotational spun polymeric fibers comprise PTFE fibers.

13. The medical appliance of claim 8, wherein the tie layer is non-porous and non-fibrous.

14. The medical appliance of claim 8, wherein the second layer comprises ePTFE.

15. A medical appliance, comprising:
   a first layer of rotational spun PTFE fibers deposited in the absence of an electric field;
   a tie layer of FEP coupled to the first layer and impervious to cell migration into the tie layer; and
   a second layer of ePTFE.

16. The medical appliance of claim 15, wherein the first layer defines a luminal surface of the medical appliance.

17. The medical appliance of claim 15, wherein the first layer is permeable to cell migration into the first layer.

18. The medical appliance of claim 15, wherein the tie layer is non-porous and non-fibrous.

19. The medical appliance of claim 15, wherein the second layer is permeable to cell migration into the second layer.

20. A medical appliance, comprising:

a first layer of serially deposited polytetrafluoroethylene (PTFE) fibers deposited in the absence of an electric field;

a tie layer comprising FEP, the tie layer coupled to the first layer and impervious to cell migration into the tie layer; and a second layer of PTFE.

21. The medical appliance of claim 1, wherein the serially deposited PTFE fibers are rotational spun.

22. The medical appliance of claim 1, wherein the first layer is permeable to cell migration into the first layer.

23. The medical appliance of claim 1, wherein the first layer defines a luminal surface of the medical appliance.

24. The medical appliance of claim 1, wherein the tie layer is non-porous and non-fibrous.

25. The medical appliance of claim 1, wherein the second layer is permeable to cell migration into the second layer.

26. The medical appliance of claim 1, wherein the second layer comprises expanded polytetrafluoroethylene (ePTFE).

* * * * *